US012781208B2

(12) United States Patent
Kim et al.

(10) Patent No.: US 12,781,208 B2
(45) Date of Patent: Nov. 3, 2026

(54) ***STREPTOCOCCUS PYOGENES*-DERIVED CAS9 VARIANT**

(71) Applicant: TOOLGEN INCORPORATED, Seoul (KR)

(72) Inventors: Younghoon Kim, Seoul (KR); Keunwoo Choi, Seoul (KR); Jeongjoon Lee, Gyeonggi-do (KR)

(73) Assignee: TOOLGEN INCORPORATED, Seoul (KR)

( * ) Notice: Subject to any disclaimer, the term of this patent is extended or adjusted under 35 U.S.C. 154(b) by 214 days.

(21) Appl. No.: 18/832,216

(22) PCT Filed: Jan. 20, 2023

(86) PCT No.: PCT/KR2023/001033
§ 371 (c)(1),
(2) Date: Jul. 23, 2024

(87) PCT Pub. No.: WO2023/140694
PCT Pub. Date: Jul. 27, 2023

(65) Prior Publication Data

US 2025/0154479 A1 May 15, 2025

(30) Foreign Application Priority Data

Jan. 24, 2022 (KR) ........................ 10-2022-0010253

(51) Int. Cl.
*C12N 9/22* (2006.01)
*C12N 15/11* (2006.01)

(52) U.S. Cl.
CPC .............. *C12N 9/22* (2013.01); *C12N 15/111* (2013.01); *C07K 2319/09* (2013.01); *C12N 2310/20* (2017.05)

(58) Field of Classification Search
None
See application file for complete search history.

(56) References Cited

FOREIGN PATENT DOCUMENTS

| | | | |
|---|---|---|---|
| EP | 3640335 | A2 | 4/2020 |
| KR | 10-2018-0136914 | A | 12/2018 |
| KR | 10-2021-0023833 | A | 3/2021 |
| WO | 2018-057946 | A2 | 3/2018 |
| WO | WO-2019/217943 | A1 | 11/2019 |
| WO | WO-2020-236936 | A1 | 11/2020 |
| WO | WO-2021-151073 | A2 | 7/2021 |

OTHER PUBLICATIONS

Accession BIC16305. Oct. 1, 2020 (Year: 2020).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Guo, M., et al.; 'Structural insights into a high fidelity variant of SpCas9', Cell Research, 2019, 29 vol., 183-192 pg.
International Search Report from corresponding PCT Application No. PCT/KR2023/001033, dated Apr. 26, 2023.
Written Opinion of the International Searching Authority from corresponding PCT Application No. PCT/KR2023/001033, dated Apr. 26, 2023.
Office Action for KR Application No. 10-2024-7024833, issued on Aug. 10, 2026.
Walton et al., "Unconstrained genome targeting with near-PAMless engineered CRISPR-Cas9 variants", Science 368, p. 290-296(Apr. 17, 2020.).

* cited by examiner

*Primary Examiner* — Christian L Fronda
(74) *Attorney, Agent, or Firm* — Harness, Dickey & Pierce, P.L.C.

(57) ABSTRACT

The present disclosure discloses a SpCas9 variant. The SpCas9 variant is characterized by the ability to recognize a PAM sequence different from that of a wild-type SpCas9 protein.

14 Claims, 25 Drawing Sheets

Specification includes a Sequence Listing.

pblc vector

Self 3/19
Completion 16/19 piggybac vector

Self 1/19
Partial sequencing 1/19
Completion 17/19

FIG. 14

| TT top30 | | | CC top 30 | |
|---|---|---|---|---|
| FI | GHC | | RF | MQP |
| YV | RSR | | EA | VEK |
| HM | SMR | | MY | PWV |
| KF | RVR | | KW | QWQ |
| ER | HSV | | WV | RRT |
| SM | RRT | | YM | NCA |
| MN | RGR | | HV | TCA |
| IM | TAM | | NM | PCI |
| RF | QLE | | GE | SWN |
| GE | QRR | | RY | GET |
| QC | PYR | | YW | YYD |
| CC | TPL | | TY | PSK |
| IH | CTR | | DY | PEG |
| RL | CPD | | NW | QTW |
| NT | GVV | | LN | IAH |
| NM | KGR | | DW | DSR |
| HI | SCR | | PR | CTH |
| CL | RLR | | YF | CVK |
| SL | HCT | | RH | GHS |
| QV | SAR | | RT | TQP |
| YK | VSR | | KF | VQH |
| IL | SAA | | CF | SWH |
| KS | ALC | | IR | PYA |
| NL | KTR | | HP | RYH |
| DP | FNT | | VY | STH |
| WY | PWR | | MW | NPF |
| RC | NAP | | CY | DEE |
| IR | VSV | | FY | NHP |
| LQ | RFT | | KY | CDV |
| TT | NTS | | QY | CCS |

FIG. 16

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 13.86495 | 15.47149 | 13.66335 | 12.50827 | 17.32406 | 14.66386 | 9.512295 | 15.78417 | 20.7153 | 21.38201 | 19.56014 | 26.37125 | 17.39845 | 19.9854 | 20.11691 | 18.66757 |
| CA | 17.4782 | 19.35697 | 16.46214 | 17.91807 | 22.20088 | 21.0466 | 11.70481 | 20.82017 | 22.09127 | 22.52689 | 17.75659 | 26.48186 | 19.5395 | 22.23144 | 22.75455 | 24.82183 |
| GA | 24.34985 | 25.73913 | 21.56865 | 24.37993 | 24.52901 | 24.67728 | 16.6744 | 24.77652 | 25.4922 | 26.42868 | 22.20114 | 28.30367 | 23.32695 | 26.51422 | 25.44338 | 26.65512 |
| TA | 11.62241 | 13.50372 | 10.88514 | 12.52406 | 15.52831 | 14.92507 | 7.325422 | 14.34275 | 17.84103 | 18.80783 | 18.09445 | 27.83716 | 13.24656 | 15.76055 | 15.14013 | 16.68416 |
| AC | 4.926334 | 8.67377 | 4.124287 | 7.521863 | 3.631588 | 3.329248 | 1.337704 | 5.294552 | 15.17508 | 13.21299 | 13.46848 | 25.34226 | 10.16137 | 9.904914 | 8.017685 | 8.845736 |
| CC | 1.992158 | 4.82262 | 1.695975 | 3.90925 | 2.033572 | 3.999539 | 1.214547 | 3.877649 | 10.16311 | 10.48625 | 9.078048 | 20.68097 | 5.30665 | 5.900013 | 4.010357 | 7.144645 |
| GC | 7.818413 | 9.522266 | 4.563516 | 8.550645 | 4.557895 | 4.807729 | 2.92612 | 8.445419 | 9.722132 | 10.25629 | 7.32814 | 18.4269 | 13.04752 | 14.14794 | 8.016272 | 13.99207 |
| TC | 2.30078 | 5.807724 | 3.94529 | 3.348426 | 2.300445 | 1.617844 | 1.906988 | 2.926074 | 11.49666 | 8.890912 | 9.285306 | 20.3022 | 4.58987 | 3.063417 | 3.404083 | 4.607525 |
| AG | 36.6576 | 35.00354 | 32.74136 | 35.93262 | 32.8311 | 32.84411 | 29.17796 | 32.53199 | 37.05405 | 35.68764 | 35.59698 | 38.45679 | 40.91882 | 38.86567 | 41.77987 | 41.28744 |
| CG | 33.6123 | 34.17915 | 31.62579 | 37.023 | 36.01624 | 31.05759 | 29.07078 | 33.59482 | 35.47451 | 33.57376 | 34.20767 | 36.39573 | 40.18201 | 37.88929 | 37.76644 | 41.3989 |
| GG | 37.13515 | 34.18375 | 36.11594 | 39.44722 | 34.53431 | 32.71749 | 30.11686 | 33.56365 | 38.03406 | 40.04299 | 36.28164 | 37.41864 | 42.96359 | 41.30319 | 40.7862 | 42.80954 |
| TG | 35.50976 | 36.4199 | 34.78968 | 38.71073 | 35.30074 | 32.80794 | 29.10545 | 33.44545 | 36.62335 | 35.89904 | 34.68722 | 35.86979 | 38.02084 | 41.27143 | 40.81488 | 43.05795 |
| AT | 6.178391 | 8.405767 | 6.553539 | 7.728632 | 5.45144 | 5.917268 | 3.123386 | 7.873174 | 16.7842 | 16.08884 | 14.81816 | 28.26605 | 5.842906 | 5.372436 | 5.266355 | 5.782414 |
| CT | 4.899334 | 6.789331 | 4.848423 | 6.06575 | 3.707556 | 6.066055 | 2.606929 | 7.191508 | 12.3061 | 11.90944 | 11.54241 | 25.07651 | 5.019209 | 4.76366 | 4.324397 | 6.168987 |
| GT | 10.67653 | 14.41409 | 10.39202 | 13.30202 | 8.607934 | 10.48488 | 4.800652 | 11.53772 | 13.86925 | 14.58729 | 12.6982 | 23.00437 | 9.546774 | 10.63082 | 6.292894 | 10.3547 |
| TT | 4.107005 | 3.799931 | 2.793148 | 3.0235 | 3.096303 | 1.521556 | 1.902566 | 3.423974 | 12.41956 | 10.76281 | 9.783736 | 21.36492 | 3.025629 | 2.457213 | 3.026531 | 2.645747 |

FIG. 17

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 16.2359 | 24.23875 | 19.16168 | 16.00258 | 10.39339 | 9.963734 | 6.704333 | 7.731851 | 41.87379 | 49.10976 | 34.53221 | 40.19434 | 18.4096 | 22.27733 | 12.87963 | 6.597242 |
| CA | 18.95086 | 25.88007 | 20.01267 | 17.64812 | 11.0683 | 10.35464 | 5.465531 | 6.425768 | 42.07421 | 46.47752 | 34.42818 | 42.40758 | 17.35943 | 26.1375 | 13.1549 | 7.465787 |
| GA | 29.40225 | 31.86096 | 25.83696 | 27.36908 | 15.48423 | 14.50023 | 6.56353 | 10.42714 | 43.3123 | 48.16235 | 38.65714 | 45.49055 | 21.92815 | 27.8013 | 14.70992 | 9.492429 |
| TA | 11.15037 | 16.85184 | 15.13608 | 15.73247 | 5.380292 | 5.883619 | 4.957573 | 3.764279 | 30.49705 | 40.45758 | 24.23802 | 31.78989 | 11.07902 | 16.00125 | 8.534891 | 3.040006 |
| AC | 18.78195 | 19.0625 | 19.2908 | 17.36738 | 6.07038 | 4.239708 | 3.076469 | 4.618342 | 28.47734 | 38.62413 | 19.49523 | 29.08669 | 11.20239 | 11.00236 | 7.365733 | 2.644369 |
| CC | 7.865844 | 8.076929 | 8.781009 | 7.501036 | 1.90641 | 3.295119 | 1.984545 | 2.672017 | 14.8643 | 31.4523 | 10.04998 | 21.12266 | 4.551855 | 4.087251 | 3.990253 | 2.187655 |
| GC | 23.12511 | 17.64018 | 17.2692 | 24.96329 | 4.953789 | 4.238124 | 2.843615 | 5.436013 | 28.74356 | 38.5679 | 18.21748 | 31.58296 | 10.73016 | 10.49672 | 4.917126 | 3.930815 |
| TC | 5.351818 | 7.004082 | 11.03985 | 4.276338 | 1.605201 | 2.27037 | 2.588245 | 2.4725 | 10.40675 | 23.76157 | 8.220733 | 12.103 | 4.863456 | 3.042438 | 4.531435 | 2.36629 |
| AG | 26.69611 | 31.57458 | 24.22834 | 26.91875 | 13.48391 | 15.50802 | 10.49013 | 13.05558 | 44.99874 | 45.58552 | 36.5068 | 44.29326 | 26.42564 | 31.60825 | 18.61039 | 12.6814 |
| CG | 18.53276 | 27.68513 | 16.55855 | 22.26883 | 10.49865 | 10.76262 | 6.001522 | 7.73757 | 40.87068 | 42.24106 | 30.62526 | 39.01726 | 22.26102 | 28.14172 | 11.51237 | 8.808089 |
| GG | 24.39392 | 31.33372 | 23.48821 | 30.12415 | 14.36378 | 15.06724 | 7.448602 | 13.1075 | 40.41677 | 45.87637 | 37.97777 | 42.33469 | 29.69886 | 28.98814 | 15.04645 | 13.77944 |
| TG | 18.40552 | 22.57853 | 17.48455 | 19.96858 | 6.982269 | 7.346674 | 5.836978 | 4.961618 | 32.7082 | 40.32877 | 24.70243 | 33.05085 | 16.84713 | 22.88864 | 11.53626 | 8.089089 |
| AT | 18.87282 | 21.97191 | 18.10879 | 18.72037 | 7.524359 | 6.699802 | 4.917549 | 8.738583 | 25.44988 | 35.11142 | 19.52993 | 27.79559 | 6.087057 | 5.973578 | 4.849304 | 3.258633 |
| CT | 16.8326 | 14.08516 | 11.05332 | 11.86093 | 5.212467 | 4.497487 | 4.173236 | 5.320435 | 21.39756 | 33.84187 | 14.11023 | 25.75871 | 4.298967 | 5.467575 | 3.60071 | 2.237751 |
| GT | 24.07831 | 22.52764 | 19.23988 | 25.08191 | 10.51745 | 8.244004 | 6.301631 | 10.66788 | 33.24086 | 39.85719 | 24.823 | 32.86381 | 7.321232 | 8.137638 | 3.672209 | 5.448885 |
| TT | 7.839031 | 6.041767 | 5.818503 | 5.364098 | 2.947796 | 2.423426 | 2.334392 | 2.671224 | 10.38308 | 20.64329 | 7.381501 | 11.22167 | 2.854782 | 2.527944 | 2.022473 | 2.049775 |

FIG. 18

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 14.22912 | 12.67064 | 19.13787 | 13.9796 | 18.91818 | 12.95912 | 19.54435 | 21.43079 | 15.49587 | 12.0937 | 18.46937 | 18.25309 | 20.77521 | 17.07723 | 20.64414 | 20.65042 |
| CA | 20.10259 | 12.66876 | 23.13274 | 17.49999 | 22.25335 | 14.94681 | 22.78629 | 24.7347 | 18.82713 | 12.41581 | 19.63613 | 22.40058 | 21.75275 | 18.67162 | 24.10171 | 23.61221 |
| GA | 27.13643 | 21.26252 | 25.32537 | 26.0563 | 26.01197 | 19.48545 | 23.99542 | 30.72365 | 22.27288 | 16.58765 | 24.68711 | 28.1479 | 24.36827 | 20.74148 | 22.67566 | 27.71338 |
| TA | 10.26065 | 7.903645 | 12.5146 | 12.36 | 13.56396 | 8.950085 | 12.82067 | 13.76435 | 10.15256 | 6.802485 | 10.55801 | 11.6163 | 12.93967 | 11.05153 | 14.11499 | 11.38764 |
| AC | 12.18297 | 9.553901 | 15.28518 | 12.03013 | 12.46783 | 7.042209 | 13.50783 | 14.05408 | 9.248238 | 5.389722 | 11.46029 | 7.726892 | 15.28428 | 11.04601 | 15.16371 | 11.50714 |
| CC | 4.261319 | 3.237411 | 6.255576 | 5.690871 | 7.273384 | 4.746456 | 8.937585 | 7.956121 | 4.280935 | 2.945645 | 3.835087 | 4.411804 | 8.551621 | 6.705485 | 7.792553 | 9.348089 |
| GC | 14.87033 | 7.18039 | 14.10783 | 17.62069 | 15.26774 | 8.425391 | 17.16213 | 16.846 | 8.13693 | 4.40131 | 9.047533 | 9.183173 | 18.29915 | 15.15045 | 13.9173 | 17.97789 |
| TC | 4.440841 | 4.546182 | 8.137363 | 4.397022 | 5.293816 | 2.991333 | 7.133228 | 4.834077 | 3.099394 | 1.710487 | 4.443515 | 3.867724 | 7.246803 | 5.358503 | 7.009094 | 7.709546 |
| AG | 23.01945 | 18.7284 | 20.67171 | 22.94743 | 19.74156 | 14.07928 | 24.8206 | 21.22301 | 23.25704 | 14.73587 | 21.28288 | 22.7817 | 24.81958 | 24.03978 | 23.88709 | 26.17416 |
| CG | 17.5268 | 11.40647 | 16.29357 | 18.8816 | 18.17409 | 9.547985 | 23.78172 | 19.1718 | 15.15898 | 7.933916 | 13.95012 | 17.71418 | 21.94563 | 17.89778 | 19.68109 | 27.6712 |
| GG | 22.00767 | 14.92153 | 23.68049 | 25.93811 | 22.73862 | 15.95922 | 26.4685 | 22.72548 | 23.49786 | 13.80264 | 20.75868 | 24.39997 | 27.8866 | 22.35995 | 24.29764 | 27.34908 |
| TG | 13.90651 | 7.898817 | 15.04684 | 13.91594 | 11.75065 | 7.319434 | 15.66066 | 13.96804 | 10.87853 | 6.111062 | 11.50573 | 13.15144 | 17.97783 | 15.06355 | 16.2246 | 20.64371 |
| AT | 16.50196 | 12.7769 | 22.51992 | 21.58088 | 13.75969 | 10.65039 | 20.49667 | 17.9301 | 15.97126 | 10.88227 | 20.78408 | 19.38398 | 11.96949 | 9.251562 | 12.99457 | 8.900128 |
| CT | 17.0505 | 9.595796 | 19.30547 | 14.70174 | 15.56477 | 10.88025 | 20.62415 | 17.28956 | 12.54302 | 7.639469 | 16.8803 | 17.83207 | 13.14538 | 10.02825 | 11.57298 | 10.63963 |
| GT | 23.07288 | 16.20444 | 24.88785 | 21.94018 | 20.03859 | 17.55549 | 23.74668 | 22.69041 | 19.76725 | 14.89015 | 23.97076 | 22.14373 | 15.41262 | 14.83612 | 15.21514 | 15.6232 |
| TT | 6.552499 | 4.757317 | 9.627639 | 5.9586 | 5.821216 | 4.062388 | 7.805415 | 6.81815 | 6.425295 | 3.946741 | 8.817332 | 7.861436 | 5.366896 | 3.704927 | 4.948778 | 4.252326 |

FIG. 19

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 6.161778 | 6.409186 | 8.330725 | 5.059477 | 7.573342 | 7.636146 | 4.465785 | 6.270504 | 6.486243 | 7.232372 | 5.706107 | 6.684463 | 14.23461 | 9.636734 | 12.0275 | 8.285204 |
| CA | 8.609716 | 7.881648 | 8.000456 | 5.340751 | 8.140288 | 6.980435 | 4.283078 | 7.310774 | 6.848751 | 5.536813 | 5.716997 | 6.943904 | 18.85287 | 13.49744 | 15.67382 | 14.91483 |
| GA | 12.3118 | 10.49854 | 10.95913 | 10.29874 | 10.47 | 10.0226 | 5.545303 | 10.35891 | 9.204492 | 7.00871 | 7.5159 | 8.93357 | 20.22389 | 14.60529 | 17.18368 | 17.18649 |
| TA | 5.915454 | 4.300716 | 4.100172 | 7.303979 | 4.850369 | 4.917124 | 4.582013 | 4.884606 | 2.597051 | 4.184078 | 3.779409 | 3.811554 | 11.49649 | 7.098575 | 9.341793 | 7.223165 |
| AC | 8.099149 | 8.408915 | 6.09232 | 7.365978 | 6.595789 | 5.248129 | 3.352089 | 7.315371 | 5.767312 | 3.908214 | 4.331662 | 5.02484 | 14.62106 | 11.14187 | 9.042574 | 7.77158 |
| CC | 4.623899 | 3.964905 | 2.578338 | 3.622252 | 4.682377 | 4.426684 | 1.631975 | 2.971505 | 1.954109 | 2.786897 | 1.524696 | 3.610864 | 8.758633 | 6.09363 | 5.283492 | 6.820141 |
| GC | 7.704467 | 6.79565 | 4.48437 | 8.933803 | 5.187239 | 4.58872 | 3.198745 | 6.365423 | 5.514064 | 3.284255 | 3.066693 | 3.459426 | 12.27267 | 9.760951 | 8.233218 | 10.84668 |
| TC | 4.226164 | 4.391825 | 4.135451 | 4.157447 | 2.555185 | 3.242506 | 2.64976 | 3.834896 | 2.818215 | 1.137259 | 2.011406 | 2.343333 | 8.313694 | 4.576983 | 5.766581 | 7.131891 |
| AG | 7.881454 | 9.097717 | 6.690058 | 7.164903 | 6.377237 | 6.525135 | 4.428946 | 6.873531 | 6.906442 | 7.189194 | 6.278715 | 6.958959 | 13.45767 | 11.6485 | 12.22171 | 14.15105 |
| CG | 4.198087 | 4.633656 | 3.383598 | 5.299042 | 4.920859 | 3.278855 | 2.74722 | 4.172318 | 2.992945 | 3.348477 | 3.070495 | 4.226762 | 13.19988 | 8.264699 | 9.268112 | 11.63257 |
| GG | 7.799134 | 7.355888 | 5.660301 | 7.646066 | 5.584976 | 6.897706 | 3.23779 | 6.460158 | 7.508585 | 5.82559 | 4.461188 | 6.945704 | 15.15104 | 9.655779 | 12.1709 | 15.50961 |
| TG | 3.562457 | 4.128897 | 3.832525 | 5.351542 | 3.068367 | 2.719771 | 2.569843 | 3.627469 | 2.888078 | 2.343027 | 2.411347 | 3.604741 | 9.176905 | 7.97664 | 7.336283 | 8.264501 |
| AT | 8.705089 | 9.310015 | 9.322714 | 8.654674 | 7.396753 | 6.493735 | 5.683697 | 6.760448 | 8.658334 | 7.121848 | 7.772273 | 9.555083 | 11.92775 | 9.379892 | 9.068239 | 7.385579 |
| CT | 7.907018 | 7.062048 | 8.242446 | 6.706896 | 7.184253 | 6.440584 | 5.06912 | 7.161674 | 6.008841 | 4.747545 | 5.478261 | 7.491807 | 13.45243 | 11.59552 | 10.79703 | 9.031337 |
| GT | 13.61066 | 11.19176 | 10.18952 | 12.22914 | 8.460311 | 9.00843 | 5.836077 | 8.911787 | 9.388326 | 10.185 | 8.134398 | 10.39413 | 16.39084 | 11.19744 | 8.602719 | 12.54925 |
| TT | 4.897834 | 3.826069 | 4.775191 | 4.53014 | 5.19583 | 2.610353 | 2.883266 | 5.055022 | 3.412505 | 4.033233 | 3.84902 | 3.664042 | 5.839806 | 5.195336 | 4.887559 | 4.447384 |

FIG. 20

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 8.4995807 | 6.3720254 | 8.781105 | 11.303524 | 4.9293744 | 6.2973424 | 5.2004284 | 5.2290479 | 47.281925 | 50.299951 | 54.562681 | 50.236188 | 7.8321544 | 7.7608282 | 5.9504488 | 6.9299089 |
| CA | 7.2441316 | 6.6327533 | 8.2372867 | 6.6373568 | 4.4431137 | 4.6095519 | 4.924021 | 7.3930505 | 43.184513 | 48.850939 | 46.892124 | 46.335904 | 6.0936573 | 5.412142 | 4.8834236 | 6.910108 |
| GA | 11.780037 | 7.490311 | 7.7812989 | 9.5224949 | 5.9321606 | 5.4849915 | 3.5445132 | 5.0322667 | 51.878096 | 51.180595 | 48.48501 | 49.934984 | 9.3169204 | 6.0849571 | 5.2103551 | 8.701656 |
| TA | 8.528713 | 7.1133532 | 11.057641 | 14.488263 | 5.9131385 | 7.1340574 | 5.6208949 | 6.3307174 | 39.011544 | 45.574583 | 45.273378 | 38.737779 | 14.074725 | 8.0425312 | 5.567154 | 8.9449323 |
| AC | 3.2933562 | 5.4477891 | 7.4282184 | 6.1762215 | 4.7730727 | 4.1917108 | 2.6605902 | 3.857502 | 9.7521342 | 10.484654 | 52.281053 | 10.00991 | 4.8762101 | 7.0646953 | 4.0649385 | 6.7770209 |
| CC | 4.3491236 | 3.8522263 | 4.7426242 | 4.3178975 | 8.4438472 | 5.6692328 | 1.9946165 | 3.9355165 | 5.3823467 | 7.3128701 | 36.174032 | 5.2518306 | 6.0472998 | 3.245238 | 3.803993 | 5.8179367 |
| GC | 4.5549175 | 5.389097 | 4.0576957 | 4.8969456 | 2.9360125 | 3.5051682 | 2.7435958 | 5.739054 | 11.318102 | 16.671307 | 30.496083 | 15.867542 | 5.9540214 | 4.4259661 | 3.9563918 | 7.5846396 |
| TC | 5.2287559 | 5.0750202 | 6.4822899 | 5.6076844 | 4.8148454 | 4.0541967 | 3.9475997 | 5.1338909 | 4.63593 | 4.7616043 | 40.540131 | 4.4588532 | 11.683177 | 5.2134028 | 6.9190198 | 10.167298 |
| AG | 37.502196 | 36.255372 | 44.706006 | 35.604595 | 14.826723 | 18.368004 | 17.168762 | 15.310753 | 63.737829 | 64.705406 | 67.22907 | 66.841794 | 9.2994794 | 11.716098 | 7.5025183 | 8.8707405 |
| CG | 34.166888 | 36.276259 | 37.064354 | 36.847317 | 18.191654 | 21.921852 | 16.579017 | 16.515257 | 65.506412 | 63.658161 | 65.505599 | 65.783731 | 7.467091 | 11.709556 | 5.3663065 | 5.9084003 |
| GG | 39.933925 | [illegible] | 41.199873 | 41.876141 | 17.174867 | 21.605159 | 19.459312 | 19.657708 | 63.40352 | 66.697379 | 67.284799 | 65.794378 | 16.446723 | 15.071049 | 12.071315 | 13.789627 |
| TG | 41.229186 | 35.276715 | 42.598767 | 39.099078 | 15.350812 | 19.350539 | 15.805895 | 17.035526 | 61.90805 | 65.975637 | 66.853065 | 62.299116 | 8.5327867 | 11.960767 | 7.1369172 | 6.341925 |
| AT | 7.3553419 | 7.3115588 | 12.523274 | 8.3271138 | 6.0025241 | 4.4096788 | 3.9163077 | 6.8556569 | 15.766007 | 21.287756 | 50.635437 | 17.791887 | 11.00391 | 9.104086 | 5.8289504 | 9.5152422 |
| CT | 4.6473775 | 7.8518567 | 8.2677247 | 6.4479407 | 3.6855903 | 5.1091521 | 4.7002182 | 4.6075335 | 14.449233 | 24.032271 | 36.992752 | 17.067752 | 6.2849708 | 4.0558117 | 4.2338742 | 8.9202054 |
| GT | 6.3252901 | 6.4024639 | 4.5593362 | 8.6286768 | 5.8302768 | 2.9055096 | 2.5598933 | 6.0727767 | 22.765046 | 33.642221 | 35.280833 | 27.866348 | 6.8975964 | 7.1188738 | 4.0418464 | 7.7957169 |
| TT | 13.736872 | 5.8545119 | 6.0827314 | 9.7494733 | 8.21148 | 5.1005502 | 5.7735109 | 6.0805134 | 11.368085 | 8.3384329 | 37.784224 | 8.6966734 | 8.2341633 | 7.3959877 | 6.9077167 | 13.369076 |

FIG. 21

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 22.072648 | 17.722543 | 47.447382 | 25.16457 | 23.12288 | 14.198454 | 39.264065 | [illegible] | 41.972341 | 37.386341 | 53.841737 | 47.131896 | 33.027616 | 23.732209 | 56.629515 | 26.140724 |
| CA | 27.649767 | 21.592475 | 51.680994 | 29.696166 | 29.634989 | 18.732799 | 41.496877 | [illegible] | 39.991723 | 34.992395 | 53.630332 | 47.559023 | 31.91598 | 28.222833 | 54.707372 | 29.848634 |
| GA | 40.502823 | 31.914194 | 52.570014 | 38.674108 | 34.591484 | 23.608904 | 40.406183 | [illegible] | 50.670147 | 42.85196 | 58.445697 | 52.021591 | 37.926301 | 32.165741 | 60.74273 | 40.134262 |
| TA | 21.183864 | 17.437699 | 44.845316 | 25.542909 | 17.927315 | 11.818031 | 31.584497 | [illegible] | 35.326391 | 23.585792 | 47.304036 | 40.969412 | 24.957225 | 19.150367 | 48.913602 | 19.33372 |
| AC | 7.9727057 | 7.7457522 | 20.234102 | 8.9063907 | 5.8538928 | 4.6529656 | 9.9731979 | 6.2193335 | 15.023439 | 10.273606 | 24.651419 | 18.783096 | 11.203451 | 7.3074412 | 28.332612 | 8.215311 |
| CC | 5.1536892 | 5.2895865 | 8.759021 | 7.1549948 | 7.9540856 | 6.4026363 | 6.0332462 | 5.7919893 | 9.0552433 | 7.6827427 | 14.041313 | 13.192916 | 7.5724309 | 5.0392604 | 15.326358 | 8.2484804 |
| GC | 8.9398758 | 7.5455161 | 24.149195 | 10.392273 | 5.3779339 | 4.6450935 | 16.146344 | 9.0711656 | 12.232693 | 8.784741 | 23.774739 | 18.250245 | 11.32467 | 7.3594176 | 34.492799 | 11.447295 |
| TC | 6.2426846 | 5.2526583 | 9.566299 | 6.6593677 | 6.2904827 | 5.3854374 | 7.2613837 | 6.2139779 | 9.6148694 | 5.9885102 | 16.856782 | 11.485961 | 7.8413725 | 5.5997898 | 15.159991 | 9.7425146 |
| AG | 51.753974 | [illegible] | 61.688343 | 52.150398 | 45.223259 | 38.143672 | 58.059435 | [illegible] | 59.342867 | 54.333146 | 59.731131 | 59.412398 | 54.574518 | 53.900605 | 63.497629 | 60.086077 |
| CG | 50.297148 | [illegible] | 58.479072 | 53.148437 | 46.661342 | 36.561238 | 58.805022 | [illegible] | 56.801239 | 46.244807 | 59.767137 | 58.340829 | 54.714426 | 49.867626 | 60.792745 | 55.865458 |
| GG | 52.813731 | [illegible] | 59.14511 | 60.580006 | 45.532269 | 38.869034 | 54.497428 | [illegible] | 54.052943 | 53.661489 | 61.08511 | 59.436636 | 56.919989 | 50.028155 | 63.238627 | 57.258204 |
| TG | 52.521093 | [illegible] | 61.808805 | 54.642546 | 46.439138 | 38.508445 | 53.570283 | [illegible] | 54.609126 | 50.558545 | 61.619817 | 58.991426 | 52.756898 | 50.244736 | 62.667833 | 59.913512 |
| AT | 14.588427 | 11.770696 | 40.793096 | 16.203988 | 8.3503054 | 6.5155083 | 19.499919 | 11.459201 | 28.724165 | 20.11855 | 46.410131 | 31.419486 | 17.324933 | 8.8569794 | 41.047624 | 11.407643 |
| CT | 9.8114688 | 9.8527954 | 31.957373 | 15.708008 | 7.4257579 | 7.7064761 | 17.825969 | 9.9318569 | 19.89552 | 14.639774 | 45.020663 | 25.327327 | 8.3425605 | 7.6719855 | 32.581233 | 11.65938 |
| GT | 18.529753 | 17.578092 | 40.178954 | 23.467767 | 12.407971 | 9.0126837 | 28.247879 | 15.211442 | 31.898013 | 25.247377 | 51.663768 | 36.782187 | 15.860355 | 15.070078 | 44.011284 | 12.76829 |
| TT | 12.759394 | 6.852785 | 17.236537 | 10.292152 | 6.9318363 | 5.8760985 | 9.0873022 | 9.3161156 | 17.49059 | 9.831685 | 31.396736 | 18.000826 | 9.6836442 | 8.6872559 | 16.541904 | 11.642388 |

FIG. 22

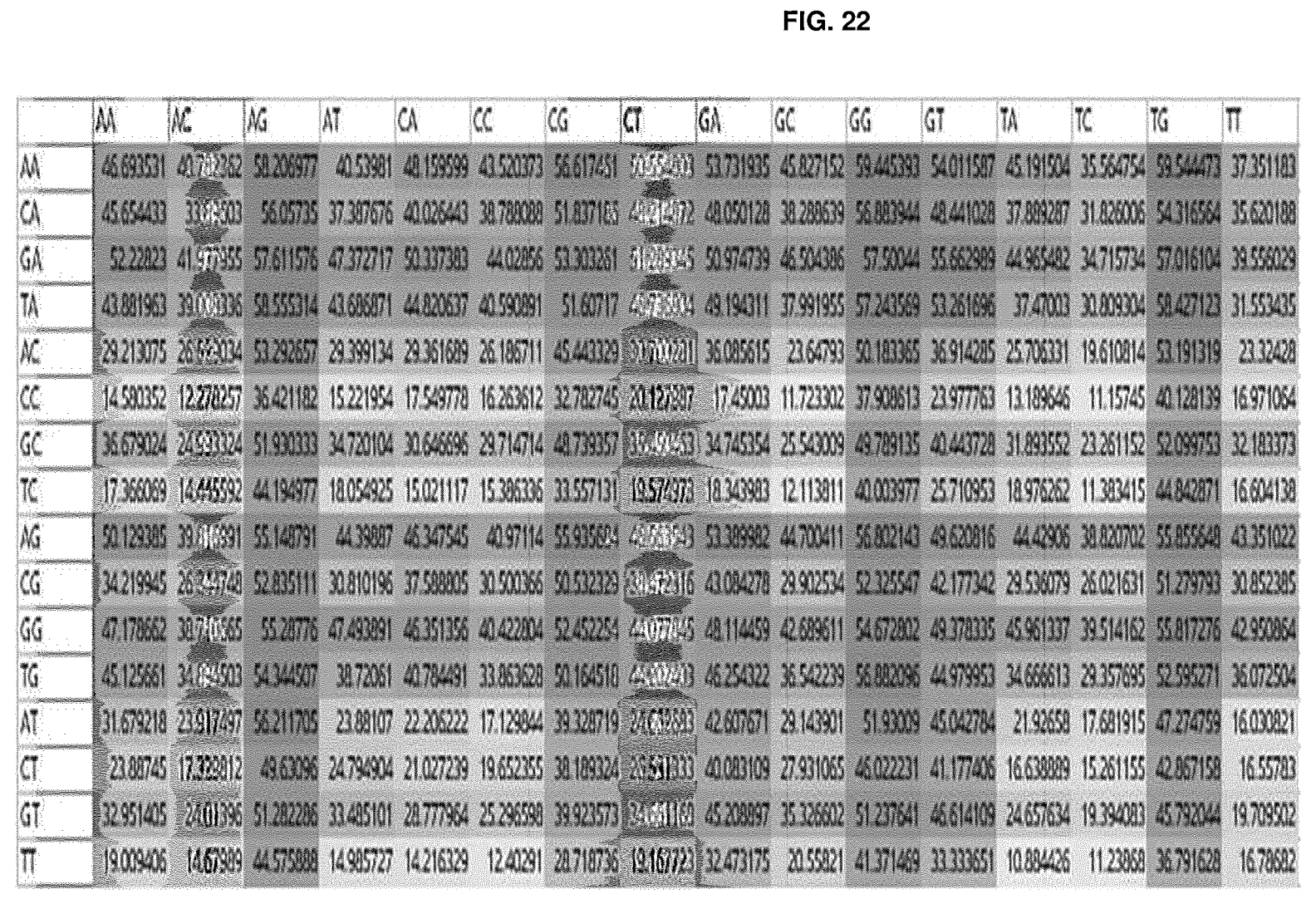

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 46.693531 | [illegible] | 58.206977 | 40.53981 | 48.159599 | 43.520373 | 56.617451 | [illegible] | 53.731935 | 45.827152 | 59.445393 | 54.011587 | 45.191504 | 35.564754 | 59.544473 | 37.351183 |
| CA | 45.654433 | [illegible] | 56.05735 | 37.387676 | 40.026443 | 38.788088 | 51.837165 | [illegible] | 48.050128 | 38.288639 | 56.883944 | 48.441028 | 37.889287 | 31.826006 | 54.316564 | 35.620188 |
| GA | 52.22823 | [illegible] | 57.611576 | 47.372717 | 50.337383 | 44.02856 | 53.303261 | [illegible] | 50.974739 | 46.504386 | 57.50044 | 55.662989 | 44.965482 | 34.715734 | 57.016104 | 39.556029 |
| TA | 43.881963 | [illegible] | 58.555314 | 43.686871 | 44.820637 | 40.590891 | 51.60717 | [illegible] | 49.194311 | 37.991955 | 57.243569 | 53.261696 | 37.47003 | 30.809304 | 58.427123 | 31.553435 |
| AC | 29.213075 | [illegible] | 53.292657 | 29.399134 | 29.361689 | 26.186711 | 45.443329 | [illegible] | 36.085615 | 23.64793 | 50.183365 | 36.914285 | 25.706331 | 19.610814 | 53.191319 | 23.32428 |
| CC | 14.580352 | 12.270257 | 36.421182 | 15.221954 | 17.549778 | 16.263612 | 32.782745 | 20.127287 | 17.45003 | 11.723302 | 37.908613 | 23.977763 | 13.189646 | 11.15745 | 40.128139 | 16.971064 |
| GC | 36.679024 | [illegible] | 51.930333 | 34.720104 | 30.646696 | 29.714714 | 40.739357 | [illegible] | 34.745354 | 25.543009 | 49.789135 | 40.443728 | 31.893552 | 23.261152 | 52.099753 | 32.183373 |
| TC | 17.366069 | 14.445592 | 44.194977 | 18.054925 | 15.021117 | 15.386336 | 33.557131 | 19.574978 | 18.343983 | 12.113811 | 40.003977 | 25.710953 | 18.976262 | 11.383415 | 44.842871 | 16.604138 |
| AG | 50.129385 | [illegible] | 55.148791 | 44.39887 | 46.347545 | 40.97114 | 55.935684 | [illegible] | 53.389982 | 44.700411 | 56.802143 | 49.620816 | 44.42906 | 38.820702 | 55.855648 | 43.351022 |
| CG | 34.219945 | [illegible] | 52.835111 | 30.810196 | 37.588805 | 30.500366 | 50.532329 | [illegible] | 43.084278 | 29.902534 | 52.325547 | 42.177342 | 29.536079 | 26.021631 | 51.279793 | 30.852385 |
| GG | 47.178662 | [illegible] | 55.28776 | 47.493891 | 46.351356 | 40.422804 | 52.452254 | [illegible] | 48.114459 | 42.689611 | 54.672802 | 49.378335 | 45.961337 | 39.514162 | 55.817276 | 42.950864 |
| TG | 45.125661 | [illegible] | 54.344507 | 38.72061 | 40.784491 | 33.863628 | 50.164518 | [illegible] | 46.254322 | 36.542239 | 56.882096 | 44.979953 | 34.666613 | 29.357695 | 52.595271 | 36.072504 |
| AT | 31.679218 | 23.917497 | 56.211705 | 23.88107 | 22.206222 | 17.129844 | 39.328719 | [illegible] | 42.607671 | 29.143901 | 51.93009 | 45.042784 | 21.92658 | 17.681915 | 47.274759 | 16.030821 |
| CT | 23.88745 | [illegible] | 49.63096 | 24.794904 | 21.027239 | 19.652355 | 38.189324 | [illegible] | 40.083109 | 27.931065 | 46.022231 | 41.177406 | 16.638889 | 15.261155 | 42.867158 | 16.55783 |
| GT | 32.951405 | [illegible] | 51.282286 | 33.485101 | 28.777964 | 25.296598 | 39.923573 | [illegible] | 45.208897 | 35.326602 | 51.237641 | 46.614109 | 24.657634 | 19.394083 | 45.792044 | 19.709502 |
| TT | 19.009406 | 14.67989 | 44.575888 | 14.985727 | 14.216329 | 12.40291 | 28.718736 | 19.167723 | 32.473175 | 20.55821 | 41.371469 | 33.333651 | 10.884426 | 11.23868 | 36.791628 | 16.78682 |

FIG. 23

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 22.697967 | [illegible] | 23.346659 | 22.633871 | 27.792786 | 25.441539 | 17.395775 | [illegible] | 28.479958 | 33.584071 | 29.296691 | 40.879214 | 29.199043 | 32.232108 | 29.289982 | 30.167043 |
| CA | 29.333891 | [illegible] | 24.760916 | 29.603145 | 29.234186 | 29.053018 | 21.888346 | [illegible] | 30.663508 | 31.311331 | 27.469623 | 35.993923 | 30.63427 | 34.202595 | 32.358037 | 36.741249 |
| GA | 38.706383 | [illegible] | 31.912988 | 35.464109 | 34.813752 | 33.245447 | 25.161493 | [illegible] | 33.830327 | 35.457899 | 31.60505 | 38.261288 | 35.848348 | 33.656733 | 36.307395 | 38.547236 |
| TA | 22.680551 | [illegible] | 16.689247 | 25.314893 | 23.702776 | 23.017148 | 13.290306 | [illegible] | 27.961969 | 26.895525 | 24.961486 | 36.60042 | 27.763931 | 28.337751 | 25.564872 | 29.72152 |
| AC | 9.3833298 | [illegible] | 10.205248 | 13.211198 | 8.6230033 | 7.0374013 | 4.4619715 | 10.107657 | 21.84213 | 19.53045 | 19.41734 | 34.280047 | 18.83898 | 16.760525 | 15.015735 | 15.878104 |
| CC | 6.2699121 | 8.9426514 | 5.6001469 | 9.6792747 | 8.238082 | 7.173623 | 4.8469103 | 6.9552176 | 17.097341 | 15.85804 | 14.194051 | 28.585956 | 11.15098 | 10.510047 | 8.1545498 | 13.787505 |
| GC | 12.284523 | [illegible] | 9.0318869 | 16.212117 | 8.2370453 | 9.2793245 | 5.7151371 | [illegible] | 15.298543 | 15.803737 | 12.474962 | 26.41342 | 20.721374 | 22.075076 | 12.704156 | 25.414509 |
| TC | 8.999046 | [illegible] | 7.1285233 | 9.2451887 | 6.0527518 | 4.4610506 | 5.0527222 | 7.1055108 | 16.263984 | 14.334758 | 16.267551 | 27.894522 | 11.104589 | 7.9079856 | 8.7047622 | 10.278325 |
| AG | 46.710969 | [illegible] | 44.228978 | 49.272023 | 40.278878 | 41.852367 | 38.415153 | [illegible] | 45.208488 | 46.039128 | 44.378955 | 46.035534 | 47.878757 | 50.615453 | 47.740577 | 52.827108 |
| CG | 44.916497 | [illegible] | 40.123476 | 46.113892 | 41.933232 | 39.974088 | 38.047707 | [illegible] | 43.198579 | 40.907427 | 42.606299 | 45.966712 | 46.725033 | 47.286785 | 44.304591 | 46.888343 |
| GG | 44.875728 | [illegible] | 42.208018 | 49.822401 | 41.744384 | 41.44335 | 36.038003 | [illegible] | 42.43404 | 45.033562 | 43.804927 | 46.597996 | 50.29242 | 47.070232 | 47.20437 | 50.942069 |
| TG | 46.667663 | [illegible] | 43.247938 | 47.061763 | 41.602698 | 41.567726 | 39.460858 | [illegible] | 42.192089 | 42.473608 | 41.984917 | 45.28434 | 48.173496 | 48.232222 | 47.955089 | 51.940639 |
| AT | 12.656351 | 16.037897 | 16.46725 | 17.283178 | 10.889771 | 11.818674 | 7.3434315 | [illegible] | 23.093443 | 23.273215 | 22.852852 | 38.544564 | 14.606423 | 14.1286 | 11.378777 | 11.65268 |
| CT | 8.5506911 | 13.771791 | 9.6126257 | 12.196467 | 8.8162189 | 11.648991 | 6.3301207 | [illegible] | 22.082365 | 18.87004 | 18.652178 | 32.267493 | 10.872996 | 11.152213 | 8.6847214 | 10.426125 |
| GT | 18.707169 | 21.651352 | 15.236746 | 20.218684 | 16.116306 | 17.889096 | 9.5480784 | [illegible] | 21.631132 | 20.863213 | 18.433859 | 30.768335 | 18.480905 | 18.667488 | 11.489312 | 18.228299 |
| TT | 10.746671 | 10.104572 | 8.9747294 | 9.8792931 | 7.3635974 | 6.7559135 | 5.7917222 | 8.1831932 | 19.558333 | 15.832459 | 17.814771 | 30.058471 | 8.3040289 | 8.4079921 | 8.0322549 | 11.647334 |

FIG. 24

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 30.490956 | 37.511239 | 31.32425 | 28.887385 | 18.788806 | 18.37363 | 11.27449 | 12.265978 | 55.708335 | 60.195959 | 48.268293 | 56.610965 | 30.913908 | 36.269488 | 20.357891 | 15.440329 |
| CA | 31.81197 | 38.172742 | 30.363729 | 30.85318 | 17.703419 | 15.683733 | 9.4425988 | 12.820139 | 54.22445 | 57.2895 | 47.162649 | 52.748837 | 29.221848 | 38.551779 | 19.023583 | 14.435991 |
| GA | 45.122989 | 45.003834 | 36.932041 | 45.379677 | 24.330515 | 25.145066 | 11.69539 | 20.705125 | 55.952515 | 61.226181 | 50.31896 | 58.885978 | 36.43882 | 40.543499 | 25.091752 | 19.982471 |
| TA | 25.672366 | 29.726119 | 24.018536 | 26.91327 | 11.951861 | 12.61739 | 9.9996493 | 10.793654 | 44.894257 | 52.350591 | 36.11144 | 46.192236 | 27.11434 | 27.835121 | 14.662765 | 11.92833 |
| AC | 29.186837 | 30.534581 | 30.730163 | 25.187747 | 10.772508 | 8.1210149 | 6.6430698 | 9.0372736 | 37.195632 | 47.680865 | 28.167843 | 36.272572 | 19.140772 | 18.437773 | 13.943481 | 10.153037 |
| CC | 14.207856 | 15.126909 | 14.779865 | 14.898658 | 9.5485174 | 8.3180808 | 5.2975307 | 5.475418 | 24.704991 | 40.356846 | 17.920135 | 29.330159 | 10.450259 | 8.2279952 | 7.9840227 | 9.0740717 |
| GC | 32.62054 | 29.932335 | 26.192069 | 34.08724 | 8.7953587 | 9.0295335 | 6.0580015 | 10.631431 | 37.62764 | 50.138102 | 27.37782 | 43.279065 | 19.838366 | 18.250464 | 10.394298 | 11.893947 |
| TC | 14.88446 | 11.920025 | 18.359915 | 11.423123 | 7.1457274 | 7.0414045 | 5.4587226 | 6.3271563 | 17.469659 | 33.5182 | 15.181097 | 20.448954 | 12.912256 | 8.796455 | 10.667836 | 9.2271668 |
| AG | 39.797387 | 43.035165 | 39.76487 | 39.828066 | 21.756431 | 22.937881 | 16.144913 | 21.714384 | 56.679938 | 61.018702 | 48.486047 | 53.095657 | 38.271006 | 43.288172 | 28.036705 | 23.627751 |
| CG | 28.375275 | 37.265428 | 25.89499 | 33.747138 | 17.329675 | 16.714328 | 10.351514 | 14.410583 | 52.781816 | 54.868548 | 43.627346 | 51.6965 | 31.728037 | 38.580521 | 17.077061 | 16.448454 |
| GG | 40.917187 | 41.616023 | 33.793636 | 45.969317 | 21.702442 | 23.290581 | 13.848355 | 19.574391 | 53.99059 | 57.005899 | 48.879588 | 52.686444 | 42.292914 | 42.030764 | 23.401519 | 22.962736 |
| TG | 31.46122 | 33.850022 | 28.845368 | 30.500415 | 12.689435 | 12.356962 | 9.6733098 | 13.337423 | 46.822331 | 51.63087 | 37.175353 | 45.650672 | 27.748178 | 34.897383 | 16.964913 | 16.093674 |
| AT | 32.194518 | 34.232774 | 32.610577 | 29.01817 | 15.089611 | 13.123117 | 9.6880649 | 14.457095 | 38.932327 | 44.792272 | 28.976772 | 39.843463 | 18.167261 | 17.238519 | 9.9547523 | 12.867559 |
| CT | 25.274042 | 23.955364 | 19.085431 | 21.286836 | 10.789662 | 10.164818 | 8.7333983 | 10.625177 | 32.211829 | 45.346428 | 23.204616 | 37.536784 | 8.6487392 | 10.966142 | 7.4111385 | 11.179077 |
| GT | 35.286438 | 35.403511 | 28.565806 | 34.270403 | 20.427413 | 13.929372 | 11.977399 | 17.470121 | 44.724239 | 50.350937 | 33.684598 | 47.014186 | 15.104702 | 15.614729 | 9.4598941 | 10.933461 |
| TT | 16.329093 | 14.425862 | 13.228343 | 13.811861 | 11.118094 | 6.3295756 | 7.0983054 | 9.227272 | 18.878361 | 29.954241 | 14.914959 | 19.76252 | 9.6711367 | 8.926919 | 9.2278382 | 10.375407 |

FIG. 25

| | AA | AC | AG | AT | CA | CC | CG | CT | GA | GC | GG | GT | TA | TC | TG | TT |
|---|---|---|---|---|---|---|---|---|---|---|---|---|---|---|---|---|
| AA | 25.062798 | 19.653198 | 31.600037 | 25.326776 | 28.298339 | 20.480196 | 28.32766 | [illegible] | 25.730344 | 21.049426 | 29.282384 | 29.533844 | 35.459168 | 27.884583 | 32.457738 | 30.373364 |
| CA | 32.010518 | 21.165911 | 33.465799 | 25.998444 | 32.40961 | 22.573576 | 31.415772 | [illegible] | 28.901771 | 18.521212 | 29.091853 | 32.231257 | 30.336696 | 30.442779 | 32.475372 | 34.467466 |
| GA | 41.1069 | 30.763165 | 40.416953 | 37.417541 | 40.24908 | 30.941884 | 36.797512 | [illegible] | 35.636729 | 23.512036 | 36.526863 | 37.68592 | 37.842886 | 34.912478 | 39.1194 | 41.673635 |
| TA | 18.115359 | 16.025301 | 21.293308 | 23.474706 | 21.889203 | 14.997735 | 18.905974 | 22.220591 | 16.832859 | 10.688406 | 16.913918 | 20.155384 | 24.238023 | 20.289596 | 22.654994 | 22.909005 |
| AC | 19.369263 | 15.928759 | 24.199995 | 20.310653 | 19.802534 | 14.840718 | 23.261132 | 21.061481 | 16.84602 | 8.7747956 | 17.656293 | 14.613927 | 28.237348 | 22.12455 | 23.441275 | 22.527788 |
| CC | 10.289824 | 8.3031868 | 10.795815 | 11.558254 | 14.343403 | 9.3699337 | 13.154775 | 13.402581 | 8.4313158 | 6.1239712 | 8.004497 | 8.2063741 | 16.395486 | 11.635664 | 13.300057 | 15.970042 |
| GC | 21.617561 | 12.925435 | 22.599984 | 22.47234 | 21.838427 | 14.385138 | 26.713407 | [illegible] | 14.381228 | 7.8040844 | 15.160317 | 14.401388 | 30.347011 | 23.688736 | 21.438566 | 28.726307 |
| TC | 10.862345 | 8.0553946 | 13.25203 | 10.646378 | 10.051843 | 6.493417 | 12.285298 | 12.333885 | 5.8856801 | 4.4243516 | 9.3332666 | 6.2625975 | 17.708877 | 11.063024 | 13.951223 | 15.233067 |
| AG | 39.00421 | 26.591426 | 34.950159 | 34.002499 | 32.079145 | 21.814039 | 36.435119 | [illegible] | 34.47743 | 22.290193 | 31.868674 | 31.251668 | 39.300407 | 36.742236 | 38.044032 | 42.331785 |
| CG | 26.368627 | 19.035924 | 24.606691 | 28.073506 | 27.636357 | 16.361823 | 30.424938 | [illegible] | 23.953322 | 12.247535 | 20.319689 | 26.500596 | 32.691949 | 29.052503 | 28.142399 | 37.826217 |
| GG | 36.099238 | 26.700022 | 31.236293 | 38.966414 | 33.426669 | 24.73301 | 36.335625 | [illegible] | 32.375452 | 22.103427 | 31.338031 | 32.667291 | 40.14915 | 36.418577 | 34.785311 | 44.089116 |
| TG | 23.155789 | 14.204369 | 22.824295 | 22.97434 | 19.408656 | 11.82166 | 21.72764 | [illegible] | 17.835021 | 10.976472 | 16.970457 | 20.469552 | 27.714991 | 23.523871 | 25.987928 | 32.786814 |
| AT | 27.52561 | 24.724298 | 34.465748 | 28.682444 | 24.665078 | 18.559057 | 26.134383 | [illegible] | 24.197533 | 17.975829 | 33.156442 | 26.357679 | 24.710127 | 20.376602 | 21.270347 | 19.014059 |
| CT | 29.935715 | 16.705483 | 30.104341 | 25.031004 | 24.898247 | 16.974098 | 27.883059 | [illegible] | 20.327671 | 13.66723 | 26.807443 | 23.004976 | 18.958032 | 19.285121 | 18.551225 | 21.787337 |
| GT | 34.701083 | 24.658531 | 33.357657 | 33.287042 | 30.509977 | 23.695151 | 33.640908 | [illegible] | 27.846421 | 19.695 | 35.313274 | 29.946551 | 25.13521 | 26.938896 | 22.995637 | 27.163813 |
| TT | 17.478565 | 11.200423 | 18.408578 | 14.079307 | 13.850233 | 9.1011286 | 15.18225 | 13.420239 | 10.967431 | 7.6742907 | 15.813051 | 13.932027 | 11.716193 | 10.512689 | 13.483778 | 14.863471 |

SEQUENCE LISTING

```
Sequence total quantity: 83
SEQ ID NO: 1           moltype = AA  length = 1368
FEATURE                Location/Qualifiers
source                 1..1368
                       mol_type = protein
                       organism = synthetic construct
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 2           moltype = AA  length = 1368
FEATURE                Location/Qualifiers
source                 1..1368
                       mol_type = protein
                       organism = synthetic construct
SEQUENCE: 2
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFVSPTVA  1140
YSVLVVAKVE KGKSKKLKSV KELLGITIME RSSFEKNPID FLEAKGYKEV KKDLIIKLPK  1200
YSLFELENGR KRMLASARFL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PRAFKYFDTT IDRKVYRSTK EVLDATLIHQ SITGLYETRI DLSQLGGD              1368

SEQ ID NO: 3           moltype = AA  length = 1368
FEATURE                Location/Qualifiers
source                 1..1368
                       mol_type = protein
                       organism = synthetic construct
SEQUENCE: 3
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
```

-continued

```
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFVSPTVA  1140
YSVLVVAKVE KGKSKKLKSV KELLGITIME RSSFEKNPID FLEAKGYKEV KKDLIIKLPK  1200
YSLFELENGR KRMLASAKVL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PRAFKYFDTT IDRKQYTSTK EVLDATLIHQ SITGLYETRI DLSQLGGD              1368

SEQ ID NO: 4           moltype = AA  length = 1368
FEATURE                Location/Qualifiers
source                 1..1368
                       mol_type = protein
                       organism = synthetic construct
SEQUENCE: 4
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFVSPTVA  1140
YSVLVVAKVE KGKSKKLKSV KELLGITIME RSSFEKNPID FLEAKGYKEV KKDLIIKLPK  1200
YSLFELENGR KRMLASAQQL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PRAFKYFDTT IDPKRYLSTK EVLDATLIHQ SITGLYETRI DLSQLGGD              1368

SEQ ID NO: 5           moltype = AA  length = 1368
FEATURE                Location/Qualifiers
source                 1..1368
                       mol_type = protein
                       organism = synthetic construct
SEQUENCE: 5
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFVSPTVA  1140
YSVLVVAKVE KGKSKKLKSV KELLGITIME RSSFEKNPID FLEAKGYKEV KKDLIIKLPK  1200
YSLFELENGR KRMLASARFL QKGNELALPS KYVNFLYLAS HYEKLKGSPE DNEQKQLFVE  1260
```

-continued

```
QHKHYLDEII EQISEFSKRV ILADANLDKV LSAYNKHRDK PIREQAENII HLFTLTNLGA  1320
PRAFKYFDTT IDRKQYTSTK EVLDATLIHQ SITGLYETRI DLSQLGGD               1368

SEQ ID NO: 6            moltype = AA  length = 1368
FEATURE                 Location/Qualifiers
source                  1..1368
                        mol_type = protein
                        organism = synthetic construct
SEQUENCE: 6
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFVSPTVA  1140
YSVLVVAKVE KGKSKKLKSV KELLGITIME RSSFEKNPID FLEAKGYKEV KKDLIIKLPK  1200
YSLFELENGR KRMLASAMTL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PRAFKYFDTT IDPKKYYLSTK EVLDATLIHQ SITGLYETRI DLSQLGGD             1368

SEQ ID NO: 7            moltype = RNA  length = 12
FEATURE                 Location/Qualifiers
source                  1..12
                        mol_type = other RNA
                        organism = synthetic construct
SEQUENCE: 7
gttttagagc ta                                                      12

SEQ ID NO: 8            moltype = RNA  length = 60
FEATURE                 Location/Qualifiers
source                  1..60
                        mol_type = other RNA
                        organism = synthetic construct
SEQUENCE: 8
tagcaagtta aaataaggct agtccgttat caacttgaaa aagtggcacc gagtcggtgc  60

SEQ ID NO: 9            moltype = RNA  length = 82
FEATURE                 Location/Qualifiers
source                  1..82
                        mol_type = other RNA
                        organism = synthetic construct
SEQUENCE: 9
gttttagagc tagaaatagc aagttaaaat aaggctagtc cgttatcaac ttgaaaaagt  60
ggcaccgagt cggtgctttt tt                                           82

SEQ ID NO: 10           moltype = AA  length = 7
FEATURE                 Location/Qualifiers
source                  1..7
                        mol_type = protein
                        organism = synthetic construct
SEQUENCE: 10
PKKKRKV                                                            7

SEQ ID NO: 11           moltype = DNA  length = 655
FEATURE                 Location/Qualifiers
source                  1..655
                        mol_type = other DNA
                        organism = synthetic construct
SEQUENCE: 11
cgatgtacgg gccagatata cgcgttgaca ttgattattg actagttatt aatagtaatc  60
aattacgggg tcattagttc atagcccata tatggagttc cgcgttacat aacttacggt  120
aaatggcccg cctggctgac cgcccaacga cccccgccca ttgacgtcaa taatgacgta  180
tgttcccata gtaacgccaa tagggacttt ccattgacgt caatgggtgg actatttacg  240
gtaaactgcc cacttggcag tacatcaagt gtatcatatg ccaagtacgc cccctattga  300
cgtcaatgac ggtaaatggc ccgcctggca ttatgcccag tacatgacct tatgggactt  360
tcctacttgg cagtacatct acgtattagt catcgctatt accatggtga tgcggttttg  420
```

```
gcagtacatc aatgggcgtg gatagcggtt tgactcacgg ggatttccaa gtctccaccc  480
cattgacgtc aatgggagtt tgttttggca ccaaaatcaa cgggactttc caaaatgtcg  540
taacaactcc gccccattga cgcaaatggg cggtaggcgt gtacggtggg aggtctatat  600
aagcagagct ctctggctaa ctagagaacc cactgcttac tggcttatcg aaatt       655

SEQ ID NO: 12          moltype = AA  length = 1368
FEATURE                Location/Qualifiers
source                 1..1368
                       mol_type = protein
                       organism = synthetic construct
SEQUENCE: 12
MDKKYSIGLD IGTNSVGWAV ITDEYKVPSK KFKVLGNTDR HSIKKNLIGA LLFDSGETAE  60
RTRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI RPKRNSDKLI ARKKDWDPKK YGGFLWPTVA  1140
YSVLVVAKVE KGKSKKLKSV KELLGITIME RSSFEKNPID FLEAKGYKEV KKDLIIKLPK  1200
YSLFELENGR KRMLASAKQL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTRLGA  1320
PRAFKYFDTT IDPKQYRSTK EVLDATLIHQ SITGLYETRI DLSQLGGD                1368

SEQ ID NO: 13          moltype = DNA  length = 19
FEATURE                Location/Qualifiers
source                 1..19
                       mol_type = other DNA
                       organism = synthetic construct
SEQUENCE: 13
gtgatgaagg agatgggag                                                19

SEQ ID NO: 14          moltype = DNA  length = 19
FEATURE                Location/Qualifiers
source                 1..19
                       mol_type = other DNA
                       organism = synthetic construct
SEQUENCE: 14
gtgatgaagg agatgggag                                                19

SEQ ID NO: 15          moltype = DNA  length = 19
FEATURE                Location/Qualifiers
source                 1..19
                       mol_type = other DNA
                       organism = synthetic construct
SEQUENCE: 15
tggattacat caaagcact                                                19

SEQ ID NO: 16          moltype = DNA  length = 19
FEATURE                Location/Qualifiers
source                 1..19
                       mol_type = other DNA
                       organism = synthetic construct
SEQUENCE: 16
tgggaggcca tcacattgt                                                19

SEQ ID NO: 17          moltype = DNA  length = 19
FEATURE                Location/Qualifiers
source                 1..19
                       mol_type = other DNA
                       organism = synthetic construct
SEQUENCE: 17
atcacattgt agccctctg                                                19

SEQ ID NO: 18          moltype = DNA  length = 19
FEATURE                Location/Qualifiers
source                 1..19
                       mol_type = other DNA
```

```
                         organism = synthetic construct
SEQUENCE: 18
ggggctataa attctttgc                                          19

SEQ ID NO: 19            moltype = DNA  length = 19
FEATURE                  Location/Qualifiers
source                   1..19
                         mol_type = other DNA
                         organism = synthetic construct
SEQUENCE: 19
gaaatagtga tagatccat                                          19

SEQ ID NO: 20            moltype = DNA  length = 19
FEATURE                  Location/Qualifiers
source                   1..19
                         mol_type = other DNA
                         organism = synthetic construct
SEQUENCE: 20
tcaagggggg ctataaatt                                          19

SEQ ID NO: 21            moltype = DNA  length = 19
FEATURE                  Location/Qualifiers
source                   1..19
                         mol_type = other DNA
                         organism = synthetic construct
SEQUENCE: 21
gtgtgctcaa gggggcta                                           19

SEQ ID NO: 22            moltype = DNA  length = 19
FEATURE                  Location/Qualifiers
source                   1..19
                         mol_type = other DNA
                         organism = synthetic construct
SEQUENCE: 22
cctctgtgtg ctcaagggg                                          19

SEQ ID NO: 23            moltype = DNA  length = 19
FEATURE                  Location/Qualifiers
source                   1..19
                         mol_type = other DNA
                         organism = synthetic construct
SEQUENCE: 23
caaagcactg aatagaaat                                          19

SEQ ID NO: 24            moltype = DNA  length = 19
FEATURE                  Location/Qualifiers
source                   1..19
                         mol_type = other DNA
                         organism = synthetic construct
SEQUENCE: 24
ttacatcaaa gcactgaat                                          19

SEQ ID NO: 25            moltype = DNA  length = 19
FEATURE                  Location/Qualifiers
source                   1..19
                         mol_type = other DNA
                         organism = synthetic construct
SEQUENCE: 25
ccgccagatc accaagcac                                          19

SEQ ID NO: 26            moltype = DNA  length = 20
FEATURE                  Location/Qualifiers
source                   1..20
                         mol_type = other DNA
                         organism = synthetic construct
SEQUENCE: 26
agggccctct agatgcatgc                                         20

SEQ ID NO: 27            moltype = DNA  length = 20
FEATURE                  Location/Qualifiers
source                   1..20
                         mol_type = other DNA
                         organism = synthetic construct
SEQUENCE: 27
cgatgcgggt ctcgtacaga                                         20

SEQ ID NO: 28            moltype = DNA  length = 91
FEATURE                  Location/Qualifiers
source                   1..91
```

```
                         mol_type = other DNA
                         organism = synthetic construct
SEQUENCE: 28
aatgatacgg cgaccaccga gatctacact atagcctaca ctctttccct acacgacgct  60
cttccgatct atccacctgt tcaccctgac c                                 91

SEQ ID NO: 29            moltype = DNA  length = 91
FEATURE                  Location/Qualifiers
source                   1..91
                         mol_type = other DNA
                         organism = synthetic construct
SEQUENCE: 29
aatgatacgg cgaccaccga gatctacaca tagaggcaca ctctttccct acacgacgct  60
cttccgatct atccacctgt tcaccctgac c                                 91

SEQ ID NO: 30            moltype = DNA  length = 88
FEATURE                  Location/Qualifiers
source                   1..88
                         mol_type = other DNA
                         organism = synthetic construct
SEQUENCE: 30
caagcagaag acggcatacg agatcgagta atgtgactgg agttcagacg tgtgctcttc  60
cgatctaagt tcacgtactt gctgggca                                     88

SEQ ID NO: 31            moltype = DNA  length = 88
FEATURE                  Location/Qualifiers
source                   1..88
                         mol_type = other DNA
                         organism = synthetic construct
SEQUENCE: 31
caagcagaag acggcatacg agattctccg gagtgactgg agttcagacg tgtgctcttc  60
cgatctaagt tcacgtactt gctgggca                                     88

SEQ ID NO: 32            moltype = DNA  length = 88
FEATURE                  Location/Qualifiers
source                   1..88
                         mol_type = other DNA
                         organism = synthetic construct
SEQUENCE: 32
caagcagaag acggcatacg agataatgag cggtgactgg agttcagacg tgtgctcttc  60
cgatctaagt tcacgtactt gctgggca                                     88

SEQ ID NO: 33            moltype = DNA  length = 88
FEATURE                  Location/Qualifiers
source                   1..88
                         mol_type = other DNA
                         organism = synthetic construct
SEQUENCE: 33
caagcagaag acggcatacg agatggaatc tcgtgactgg agttcagacg tgtgctcttc  60
cgatctaagt tcacgtactt gctgggca                                     88

SEQ ID NO: 34            moltype = DNA  length = 88
FEATURE                  Location/Qualifiers
source                   1..88
                         mol_type = other DNA
                         organism = synthetic construct
SEQUENCE: 34
caagcagaag acggcatacg agatttctga atgtgactgg agttcagacg tgtgctcttc  60
cgatctaagt tcacgtactt gctgggca                                     88

SEQ ID NO: 35            moltype = DNA  length = 88
FEATURE                  Location/Qualifiers
source                   1..88
                         mol_type = other DNA
                         organism = synthetic construct
SEQUENCE: 35
caagcagaag acggcatacg agatacgaat tcgtgactgg agttcagacg tgtgctcttc  60
cgatctaagt tcacgtactt gctgggca                                     88

SEQ ID NO: 36            moltype = DNA  length = 88
FEATURE                  Location/Qualifiers
source                   1..88
                         mol_type = other DNA
                         organism = synthetic construct
SEQUENCE: 36
caagcagaag acggcatacg agatagcttc aggtgactgg agttcagacg tgtgctcttc  60
cgatctaagt tcacgtactt gctgggca                                     88

SEQ ID NO: 37            moltype = DNA  length = 88
```

```
FEATURE                Location/Qualifiers
source                 1..88
                       mol_type = other DNA
                       organism = synthetic construct
SEQUENCE: 37
caagcagaag acggcatacg agatgcgcat tagtgactgg agttcagacg tgtgctcttc  60
cgatctaagt tcacgtactt gctgggca                                      88

SEQ ID NO: 38          moltype = DNA  length = 88
FEATURE                Location/Qualifiers
source                 1..88
                       mol_type = other DNA
                       organism = synthetic construct
SEQUENCE: 38
caagcagaag acggcatacg agatcatagc cggtgactgg agttcagacg tgtgctcttc  60
cgatctaagt tcacgtactt gctgggca                                      88

SEQ ID NO: 39          moltype = DNA  length = 88
FEATURE                Location/Qualifiers
source                 1..88
                       mol_type = other DNA
                       organism = synthetic construct
SEQUENCE: 39
caagcagaag acggcatacg agatttcgcg gagtgactgg agttcagacg tgtgctcttc  60
cgatctaagt tcacgtactt gctgggca                                      88

SEQ ID NO: 40          moltype = DNA  length = 88
FEATURE                Location/Qualifiers
source                 1..88
                       mol_type = other DNA
                       organism = synthetic construct
SEQUENCE: 40
caagcagaag acggcatacg agatgcgcga gagtgactgg agttcagacg tgtgctcttc  60
cgatctaagt tcacgtactt gctgggca                                      88

SEQ ID NO: 41          moltype = DNA  length = 88
FEATURE                Location/Qualifiers
source                 1..88
                       mol_type = other DNA
                       organism = synthetic construct
SEQUENCE: 41
caagcagaag acggcatacg agatctatcg ctgtgactgg agttcagacg tgtgctcttc  60
cgatctaagt tcacgtactt gctgggca                                      88

SEQ ID NO: 42          moltype = DNA  length = 66
FEATURE                Location/Qualifiers
source                 1..66
                       mol_type = other DNA
                       organism = synthetic construct
SEQUENCE: 42
atcagggtgg cgtccagcac ctctttggtg ctcaggtagt acttggggtc gatggtggtg  60
tcaaag                                                              66

SEQ ID NO: 43          moltype = DNA  length = 66
FEATURE                Location/Qualifiers
source                 1..66
                       mol_type = other DNA
                       organism = synthetic construct
SEQUENCE: 43
atcagggtgg cgtccagcac ctctttggtg ctggtgtact gcttccggtc gatggtggtg  60
tcaaag                                                              66

SEQ ID NO: 44          moltype = DNA  length = 66
FEATURE                Location/Qualifiers
source                 1..66
                       mol_type = other DNA
                       organism = synthetic construct
SEQUENCE: 44
atcagggtgg cgtccagcac ctctttggtg ctcaggtacc gcttggggtc gatggtggtg  60
tcaaag                                                              66

SEQ ID NO: 45          moltype = DNA  length = 53
FEATURE                Location/Qualifiers
source                 1..53
                       mol_type = other DNA
                       organism = synthetic construct
SEQUENCE: 45
cggccggaag agaatgctgg cctctgccat gaccctgcag aagggaaacg aac          53
```

```
SEQ ID NO: 46          moltype = DNA  length = 53
FEATURE                Location/Qualifiers
source                 1..53
                       mol_type = other DNA
                       organism = synthetic construct
SEQUENCE: 46
cggccggaag agaatgctgg cctctgccca gcagctgcag aagggaaacg aac         53

SEQ ID NO: 47          moltype = DNA  length = 53
FEATURE                Location/Qualifiers
source                 1..53
                       mol_type = other DNA
                       organism = synthetic construct
SEQUENCE: 47
cggccggaag agaatgctgg cctctgcccg gttcctgcag aagggaaacg aac         53

SEQ ID NO: 48          moltype = DNA  length = 53
FEATURE                Location/Qualifiers
source                 1..53
                       mol_type = other DNA
                       organism = synthetic construct
SEQUENCE: 48
cggccggaag agaatgctgg cctctgccaa ggtgctgcag aagggaaacg aac         53

SEQ ID NO: 49          moltype = DNA  length = 20
FEATURE                Location/Qualifiers
source                 1..20
                       mol_type = other DNA
                       organism = synthetic construct
SEQUENCE: 49
ggcagaggcc agcattctct                                              20

SEQ ID NO: 50          moltype = DNA  length = 33
FEATURE                Location/Qualifiers
source                 1..33
                       mol_type = other DNA
                       organism = synthetic construct
SEQUENCE: 50
cagcaccaaa gaggtgctgg acgccaccct gat                               33

SEQ ID NO: 51          moltype = DNA  length = 56
FEATURE                Location/Qualifiers
source                 1..56
                       mol_type = other DNA
                       organism = synthetic construct
SEQUENCE: 51
acactctttc cctacacgac gctcttccga tctcttgaaa aagtggcacc gagtcg      56

SEQ ID NO: 52          moltype = DNA  length = 57
FEATURE                Location/Qualifiers
source                 1..57
                       mol_type = other DNA
                       organism = synthetic construct
SEQUENCE: 52
acactctttc cctacacgac gctcttccga tcttcttgaa aaagtggcac cgagtcg     57

SEQ ID NO: 53          moltype = DNA  length = 58
FEATURE                Location/Qualifiers
source                 1..58
                       mol_type = other DNA
                       organism = synthetic construct
SEQUENCE: 53
acactctttc cctacacgac gctcttccga tctcgcttga aaaagtggca ccgagtcg    58

SEQ ID NO: 54          moltype = DNA  length = 61
FEATURE                Location/Qualifiers
source                 1..61
                       mol_type = other DNA
                       organism = synthetic construct
SEQUENCE: 54
gtgactggag ttcagacgtg tgctcttccg atctttaagt cgagtaagct gaccgctgaa  60
g                                                                  61

SEQ ID NO: 55          moltype = DNA  length = 62
FEATURE                Location/Qualifiers
source                 1..62
                       mol_type = other DNA
                       organism = synthetic construct
SEQUENCE: 55
```

```
gtgactggag ttcagacgtg tgctcttccg atctattaag tcgagtaagc tgaccgctga  60
ag                                                                 62

SEQ ID NO: 56          moltype = DNA  length = 63
FEATURE                Location/Qualifiers
source                 1..63
                       mol_type = other DNA
                       organism = synthetic construct
SEQUENCE: 56
gtgactggag ttcagacgtg tgctcttccg atcttattaa gtcgagtaag ctgaccgctg  60
aag                                                                63

SEQ ID NO: 57          moltype = RNA  length = 19
FEATURE                Location/Qualifiers
source                 1..19
                       mol_type = other RNA
                       organism = synthetic construct
SEQUENCE: 57
gtgatgaagg agatgggag                                               19

SEQ ID NO: 58          moltype = RNA  length = 19
FEATURE                Location/Qualifiers
source                 1..19
                       mol_type = other RNA
                       organism = synthetic construct
SEQUENCE: 58
gtgatgaagg agatgggag                                               19

SEQ ID NO: 59          moltype = RNA  length = 19
FEATURE                Location/Qualifiers
source                 1..19
                       mol_type = other RNA
                       organism = synthetic construct
SEQUENCE: 59
tggattacat caaagcact                                               19

SEQ ID NO: 60          moltype = RNA  length = 19
FEATURE                Location/Qualifiers
source                 1..19
                       mol_type = other RNA
                       organism = synthetic construct
SEQUENCE: 60
tgggaggcca tcacattgt                                               19

SEQ ID NO: 61          moltype = RNA  length = 19
FEATURE                Location/Qualifiers
source                 1..19
                       mol_type = other RNA
                       organism = synthetic construct
SEQUENCE: 61
atcacattgt agccctctg                                               19

SEQ ID NO: 62          moltype = RNA  length = 19
FEATURE                Location/Qualifiers
source                 1..19
                       mol_type = other RNA
                       organism = synthetic construct
SEQUENCE: 62
ggggctataa attctttgc                                               19

SEQ ID NO: 63          moltype = RNA  length = 19
FEATURE                Location/Qualifiers
source                 1..19
                       mol_type = other RNA
                       organism = synthetic construct
SEQUENCE: 63
gaaatagtga tagatccat                                               19

SEQ ID NO: 64          moltype = RNA  length = 19
FEATURE                Location/Qualifiers
source                 1..19
                       mol_type = other RNA
                       organism = synthetic construct
SEQUENCE: 64
tcaagggggg ctataaatt                                               19

SEQ ID NO: 65          moltype = RNA  length = 19
FEATURE                Location/Qualifiers
source                 1..19
```

```
                         mol_type = other RNA
                         organism = synthetic construct
SEQUENCE: 65
gtgtgctcaa ggggggcta                                                  19

SEQ ID NO: 66            moltype = RNA  length = 19
FEATURE                  Location/Qualifiers
source                   1..19
                         mol_type = other RNA
                         organism = synthetic construct
SEQUENCE: 66
cctctgtgtg ctcaagggg                                                  19

SEQ ID NO: 67            moltype = RNA  length = 19
FEATURE                  Location/Qualifiers
source                   1..19
                         mol_type = other RNA
                         organism = synthetic construct
SEQUENCE: 67
caaagcactg aatagaaat                                                  19

SEQ ID NO: 68            moltype = RNA  length = 19
FEATURE                  Location/Qualifiers
source                   1..19
                         mol_type = other RNA
                         organism = synthetic construct
SEQUENCE: 68
ttacatcaaa gcactgaat                                                  19

SEQ ID NO: 69            moltype = AA  length = 16
FEATURE                  Location/Qualifiers
source                   1..16
                         mol_type = protein
                         organism = synthetic construct
SEQUENCE: 69
KRPAATKKAG QAKKKK                                                     16

SEQ ID NO: 70            moltype = AA  length = 9
FEATURE                  Location/Qualifiers
source                   1..9
                         mol_type = protein
                         organism = synthetic construct
SEQUENCE: 70
PAAKRVKLD                                                             9

SEQ ID NO: 71            moltype = AA  length = 11
FEATURE                  Location/Qualifiers
source                   1..11
                         mol_type = protein
                         organism = synthetic construct
SEQUENCE: 71
RQRRNELKRS P                                                          11

SEQ ID NO: 72            moltype = AA  length = 38
FEATURE                  Location/Qualifiers
source                   1..38
                         mol_type = protein
                         organism = synthetic construct
SEQUENCE: 72
NQSSNFGPMK GGNFGGRSSG PYGGGGQYFA KPRNQGGY                             38

SEQ ID NO: 73            moltype = AA  length = 42
FEATURE                  Location/Qualifiers
source                   1..42
                         mol_type = protein
                         organism = synthetic construct
SEQUENCE: 73
RMRIZFKNKG KDTAELRRRR VEVSVELRKA KKDEQILKRR NV                        42

SEQ ID NO: 74            moltype = AA  length = 8
FEATURE                  Location/Qualifiers
source                   1..8
                         mol_type = protein
                         organism = synthetic construct
SEQUENCE: 74
VSRKRPRP                                                              8

SEQ ID NO: 75            moltype = AA  length = 8
FEATURE                  Location/Qualifiers
```

-continued

```
source                 1..8
                       mol_type = protein
                       organism = synthetic construct
SEQUENCE: 75
PPKKARED                                                     8

SEQ ID NO: 76          moltype = AA  length = 8
FEATURE                Location/Qualifiers
source                 1..8
                       mol_type = protein
                       organism = synthetic construct
SEQUENCE: 76
PQPKKKPL                                                     8

SEQ ID NO: 77          moltype = AA  length = 12
FEATURE                Location/Qualifiers
source                 1..12
                       mol_type = protein
                       organism = synthetic construct
SEQUENCE: 77
SALIKKKKKM AP                                                12

SEQ ID NO: 78          moltype = AA  length = 5
FEATURE                Location/Qualifiers
source                 1..5
                       mol_type = protein
                       organism = synthetic construct
SEQUENCE: 78
DRLRR                                                        5

SEQ ID NO: 79          moltype = AA  length = 7
FEATURE                Location/Qualifiers
source                 1..7
                       mol_type = protein
                       organism = synthetic construct
SEQUENCE: 79
PKQKKRK                                                      7

SEQ ID NO: 80          moltype = AA  length = 10
FEATURE                Location/Qualifiers
source                 1..10
                       mol_type = protein
                       organism = synthetic construct
SEQUENCE: 80
RKLKKKIKKL                                                   10

SEQ ID NO: 81          moltype = AA  length = 10
FEATURE                Location/Qualifiers
source                 1..10
                       mol_type = protein
                       organism = synthetic construct
SEQUENCE: 81
REKKKFLKRR                                                   10

SEQ ID NO: 82          moltype = AA  length = 20
FEATURE                Location/Qualifiers
source                 1..20
                       mol_type = protein
                       organism = synthetic construct
SEQUENCE: 82
KRKGDEVDGV DEVAKKKSKK                                        20

SEQ ID NO: 83          moltype = AA  length = 17
FEATURE                Location/Qualifiers
source                 1..17
                       mol_type = protein
                       organism = synthetic construct
SEQUENCE: 83
RKCLQAGMNL EARKTKK                                           17
```

*STREPTOCOCCUS PYOGENES*-DERIVED CAS9 VARIANT

CROSS-REFERENCE TO RELATED APPLICATIONS

This application is a national phase application of PCT Application No. PCT/KR2023/001033, filed on Jan. 20, 2023, which claims the benefit and priority to Korean Patent Application Nos. 10-2022-0010253, filed on Jan. 24, 2022. The entire disclosures of the applications identified in this paragraph are incorporated herein by references.

SEQUENCE LISTING

This application contains references to amino acid sequences and/or nucleic acid sequences which have been submitted concurrently herewith as the sequence listing XML file entitled “000094usnp_SequenceListing.XML”, file size 85,590 bytes, created on 27 Jun. 2024. The aforementioned sequence listing is hereby incorporated by reference in its entirety pursuant to 37 C.F.R. § 1.52 (e) (5).

TECHNICAL FIELD

The present disclosure discloses a technology related to a CRISPR/Cas9 system, particularly Cas9 protein variants. The CRISPR/Cas system is a type of immune system found in prokaryotic organisms and includes a Cas protein and guide RNA. The detailed configuration of the Cas protein, or guide RNA, is described in detail in a published document WO2018/231018 (International Publication Number).

BACKGROUND ART

A *Streptococcus pyogenes*-derived Cas9 protein is also referred to as a SpCas9 protein, and is one of the orthologs of the Cas9 protein. The SpCas9 protein is known to exhibit double-stranded DNA cleavage activity in cells. However, gene editing using the SpCas9 protein is limited to the vicinity of the PAM sequence of 5'-NGG-3', but research has been conducted to expand the PAM range.

If the SpCas9 protein could be used in methods for gene editing with various types of PAM sequences or regardless of the PAM sequence, gene editing at various sites would be possible. Accordingly, there may be an advantage in that the most efficient gene editing site can be selected from a wider range of sites even in the same gene.

Examples of SpCas9 proteins which have been developed to recognize various PAM sequences include known SpCas9 proteins such as Nureki-NG Cas9 capable of recognizing the PAM sequence of 5'-NGN-3', and SpRY Cas9 that is close to PAMless.

The present disclosure discloses a SpCas9 variant capable of recognizing PAM sequences other than 5'-NGG-3'.

DISCLOSURE

Technical Problem

The present disclosure discloses a SpCas9 variant capable of recognizing PAM sequences other than 5'-NGG-3'.

The present disclosure discloses a CRISPR/Cas9 composition including the SpCas9 variant.

The present disclosure discloses a method for gene editing using the CRISPR/Cas9 composition.

The present disclosure discloses a method for screening the SpCas9 variant.

Technical Solution

One aspect of the present disclosure provides a *Streptococcus pyogenes* SpCas9 variant, represented by an amino acid sequence with six or more amino acid residue differences compared to SEQ ID NO: 1 which is an amino acid sequence of wild-type SpCas9 protein.

The SpCas9 variant may include one selected from the following mutations compared to the wild-type SpCas9 protein:

L1111R/D1135V/G1218K/E1219V/A1322R/R1335Q mutation;

L1111R/D1135V/G1218Q/E1219Q/A1322R/R1333P/T1337L mutation;

L1111R/D1135V/G1218R/E1219F/A1322R/R1333G/R1335H/T1337C mutation; and

L1111R/D1135V/G1218M/E1219T/A1322R/R1333P/R1335Y/T1337L mutation.

The SpCas9 variant including the L1111R/D1135V/G1218K/E1219V/A1322R/R1335Q mutation may include a sequence having at least 80% identity to an amino acid sequence of SEQ ID NO: 3 or a sequence having 100% identity to the amino acid sequence of SEQ ID NO: 3. In this case, the SpCas9 variant may recognize PAM sequence which is 5'-NGN-3'.

The SpCas9 variant including the L1111R/D1135V/G1218Q/E1219Q/A1322R/R1333P/T1337L mutation may include a sequence having at least 80% to 100% sequence identity or sequence similarity with an amino acid sequence of SEQ ID NO: 4. In this case, the SpCas9 variant may recognize PAM sequence which is 5'-NNG-3'.

The SpCas9 variant including the L1111R/D1135V/G1218R/E1219F/A1322R/R1333G/R1335H/T1337C mutation may include a sequence having at least 80% to 100% sequence identity or sequence similarity with an amino acid sequence of SEQ ID NO: 5. In this case, the SpCas9 variant may be PAMless.

The SpCas9 variant including the L1111R/D1135V/G1218M/E1219T/A1322R/R1333P/R1335Y/T1337L mutation may include a sequence having at least 80% to 100% sequence identity or sequence similarity with the amino acid sequence of SEQ ID NO: 6. In this case, the SpCas9 variant may be PAMless.

The present disclosure provides a CRISPR/Cas9 composition.

The CRISPR/Cas9 composition may include the SpCas9 variant, or a nucleic acid encoding the SpCas9 variant; and a guide RNA or a nucleic acid encoding the guide RNA. The guide RNA may include crRNA and tracrRNA. The guide RNA may form a complex by interacting with the SpCas9 variant. The guide RNA may bind to a target sequence of a target gene.

The SpCas9 variant may include L1111R/D1135V/G1218K/E1219V/A1322R/R1335Q mutation.

The SpCas9 variant may include L1111R/D1135V/G1218Q/E1219Q/A1322R/R1333P/T1337L mutation.

The SpCas9 variant may include L1111R/D1135V/G1218R/E1219F/A1322R/R1333G/R1335H/T1337C mutation.

The SpCas9 variant may include L1111R/D1135V/G1218M/E1219T/A1322R/R1333P/R1335Y/T1337L mutation.

The crRNA may include a guide domain and a direct repeat. The sequence of the direct repeat may be a sequence including at least 90% identical to SEQ ID NO: 7. The sequence of the tracrRNA may include at least 90% identical to SEQ ID NO: 8.

The CRISPR/Cas9 composition includes the SpCas9 variant and the guide RNA, and the SpCas9 variant and the guide RNA may be in the form of ribonucleoprotein (RNP).

The CRISPR/Cas9 composition may include vector which includes a nucleic acid encoding the SpCas9 variant and/or a nucleic acid encoding the guide RNA.

The present disclosure provides a method for gene editing, including introducing a CRISPR/Cas9 composition into a target subject for gene editing.

The target subject for gene editing may be a plant, animal, plant tissue, animal tissue, prokaryotic cell, or eukaryotic cell.

The introduction may be performed via an injection, transfusion, implantation, or transplantation.

The introduction may be performed via electroporation, gene gun, sonoporation, magnetofection, temporary cell squeezing, cationic liposome method, lithium acetate-DMSO, lipid-mediated transfection, calcium phosphate precipitation, PEI (polyethyleneimine)-mediated transfection, DEAE-dextran-mediated transfection, or nanoparticle-mediated nucleic acid delivery.

The introduction may be performed via route selected from subretinal, subcutaneously, intradermally, intraocularly, intravitreally, intratumorally, intranodally, intramedullary, intramuscularly, intravenous, intralymphatic, and intraperitoneally.

Advantageous Effects

The SpCas9 variant provided in the present disclosure can recognize a PAM sequence different from that of a wild-type SpCas9 protein, thereby enabling cleavage of target sequences adjacent to the PAM sequence other than 5'-NGG-3'.

BRIEF DESCRIPTION OF DRAWINGS

FIG. 14 shows the analysis results of a general PCR method carried out by assuming shuffling. In this case, the modifications in the 1218/1219 part and the modifications in the 1333/1335/1337 part, which show high results for the PAM sequence of TT or CC, are described separately in order from top to bottom.

FIG. 16 shows the results of confirming a PAM sequence recognized by a SpCas9 variant including L1111R/D1135V/G1218K/E1219V/A1322R/R1335Q mutation.

FIG. 17 shows the results of confirming a PAM sequence recognized by a SpCas9 variant including L1111R/D1135V/G1218Q/E1219Q/A1322R/R1333P/T1337L mutation.

FIG. 18 shows the results of confirming a PAM sequence recognized by a SpCas9 variant including L1111R/D1135V/G1218R/E1219F/A1322R/R1333G/R1335H/T1337C mutation.

FIG. 19 shows the results of confirming a PAM sequence recognized by a SpCas9 variant including L1111R/D1135V/G1218M/E1219T/A1322R/R1333P/R1335Y/T1337L mutation.

FIG. 20 shows the results of confirming a PAM sequence recognized by a wild-type SpCas9 protein.

FIG. 21 shows the results of confirming a PAM sequence recognized by a Nureki-NG Cas9 protein.

FIG. 22 shows the results of confirming a PAM sequence recognized by a SpRY Cas9 protein.

FIG. 23 shows the results of confirming a PAM sequence recognized by a SpCas9 variant including L1111R/D1135V/G1218K/E1219V/A1322R/R1335Q mutation.

FIG. 24 shows the results of confirming a PAM sequence recognized by a SpCas9 variant including L1111R/D1135V/G1218Q/E1219Q/A1322R/R1333P/T1337L mutation.

FIG. 25 shows the results of confirming a PAM sequence recognized by a SpCas9 variant including L1111R/D1135V/G1218R/E1219F/A1322R/R1333G/R1335H/T1337C mutation.

MODES OF THE INVENTION

Figure 1:
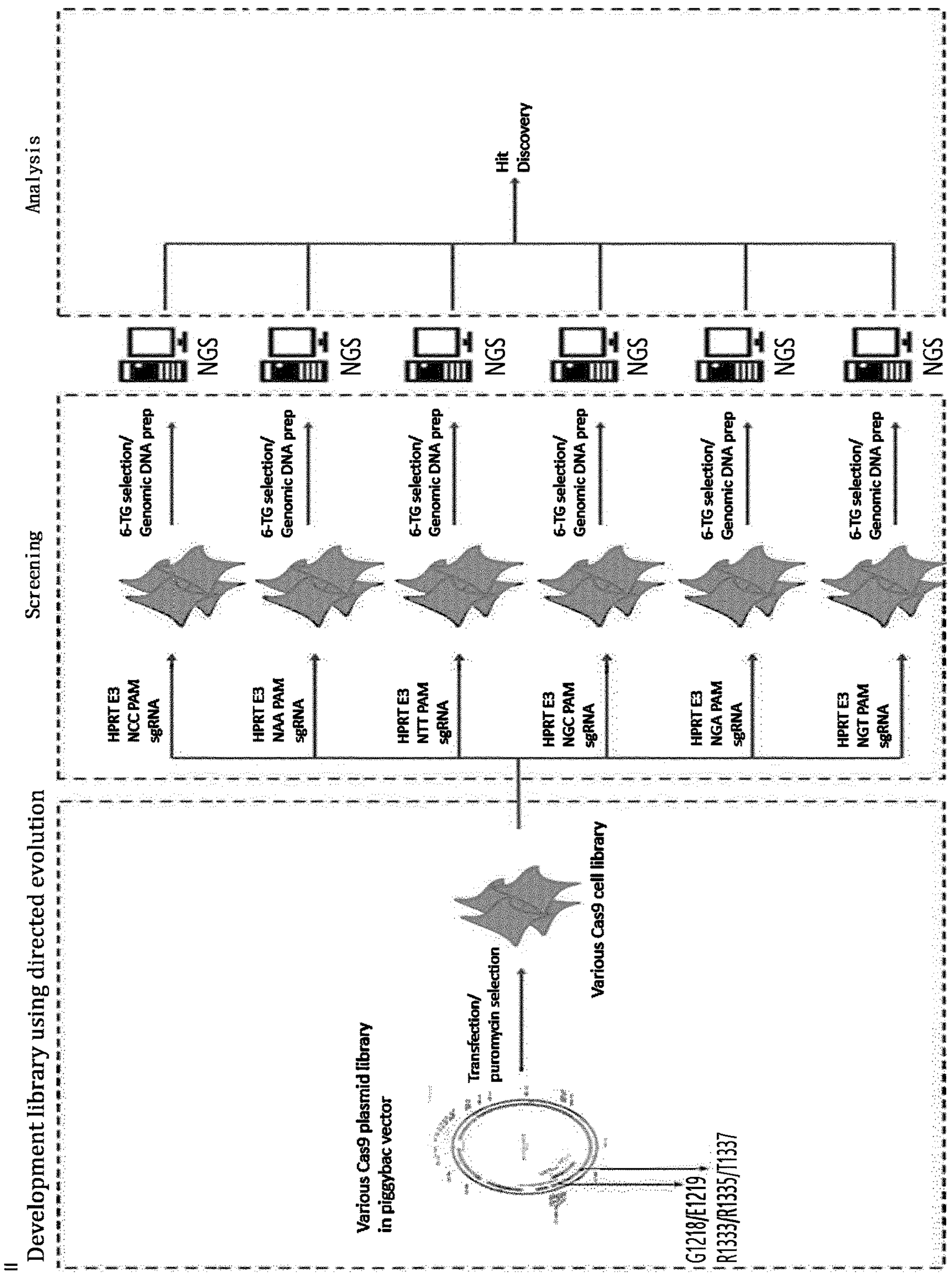
FIG. 1 describes an overall overview of a method for selecting a SpCas9 variant.

Hereinafter, the content of the disclosure will be described in more detail through specific exemplary embodiments and examples with reference to the accompanying drawings. It should be noted that the accompanying drawings include some exemplary embodiments of the disclosure, but not all exemplary embodiments. The content disclosed by the present disclosure can be implemented variously, and is not limited to specific exemplary embodiments described herein. These embodiments should be construed as being provided to satisfy the legal requirements applicable herein. A person with ordinary skill in the art to which the invention disclosed herein pertains will be able to conceive of many modifications and other exemplary embodiments of the content of the invention disclosed herein. Therefore, it should be understood that the content of the invention disclosed herein is not limited to the specific exemplary embodiments described herein, and modifications thereof and other exemplary embodiments are also within the scope of the claim.

Definitions of Terms

About

As used herein, the term "about" refers to an amount, a level, a value, a number, a frequency, a percentage, a dimension, a size, a quantity, a weight, or a length that varies to the degree of 30, 25, 20, 15, 10, 9, 8, 7, 6, 5, 4, 3, 2, or 1% with respect to a reference amount, level, value, number, frequency, percentage, dimension, size, quantity, weight, or length.

Amino Acid Sequence Notation

Unless otherwise stated, when describing the sequence of a peptide in the present specification, one-letter notation or three-letter notation of an amino acid is used, and it is described in the direction from the N-terminus to the C-terminus. For example, when expressed as RNVP, it refers to a peptide in which arginine, asparagine, valine, and proline are sequentially linked in the direction from the N-terminus to the C-terminus. As another example, when expressed as Thr-Leu-Lys, it refers to a peptide in which threonine, leucine, and lysine are sequentially linked in the direction from the N-terminus to the C-terminus. In the case of amino acids that cannot be represented by one-letter notation, other letters are used to describe these amino acids, and will be described via additional description.

The notation methods of each amino acid are as follows: Alanine (Ala, A); arginine (Arg, R); asparagine (Asn, N); aspartic acid (Asp, D); cysteine (Cys, C); glutamic acid (Glu, E); glutamine (Gln, Q); glycine (Gly, G); histidine (His, H); isoleucine (Ile, I); leucine (Leu, L); lysine (Lys K); methionine (Met, M); phenylalanine (Phe, F); proline (Pro, P); serine (Ser, S); threonine (Thr, T); tryptophan (Trp, W); tyrosine (Tyr, Y); and valine (Val, V).

Nucleic Acid Sequence Notation

The symbols A, T, C, G and U used in the present specification are to be interpreted as having the meanings understood by those skilled in the art. Depending on the context and technology, it may be interpreted as a base, nucleoside or nucleotide in DNA or RNA as appropriate. For example, when meaning a base, each may be interpreted as adenine (A), thymine (T), cytosine (C), guanine (G), or uracil (U) itself, when meaning a nucleoside, each may be interpreted as adenosine (A), thymidine (T), cytidine (C), guanosine (G), or uridine (U), and when meaning a nucleotide in a sequence, it should be construed as meaning a nucleotide including each of the above nucleosides.

In the present specification, the symbol N may be appropriately interpreted as a base, nucleoside, or nucleotide in DNA or RNA, depending on context and technology. For example, when meaning a base, each may be interpreted as any one of adenine (A), thymine (T), cytosine (C), guanine (G), and uracil (U), when meaning a nucleoside, each may be interpreted as any one of adenosine (A), thymidine (T), cytidine (C), guanosine (G), and uridine (U), and when meaning a nucleotide in a sequence, it should be construed as meaning a nucleotide including each of the above nucleosides.

Operably Linked

As used herein, the term "operably linked" refers to being linked such that in the gene expression technique, a particular configuration is linked to another configuration to allow the particular configuration to function in an intended manner. For example, the case where a promoter sequence is operably linked to a coding sequence means that the promoter is linked so as to affect the intracellular transcription and/or expression of the coding sequence. Further, the term includes all meanings that can be recognized by those skilled in the art, and may be appropriately interpreted according to the context.

Target Gene or Target Nucleic Acid

As used herein, "target gene" or "target nucleic acid" basically refers to an intracellular gene or nucleic acid that is the target of gene editing. "Target gene" and "target nucleic acid" may be used interchangeably, and may refer to the same subject. "Target gene" or "target nucleic acid" may refer to an endogenous gene or nucleic acid possessed by a target cell, or an exogenous gene or nucleic acid unless otherwise described, and is not particularly limited as long as it may be the target of gene editing. The target gene or target nucleic acid may be single-stranded DNA, double-stranded DNA, and/or RNA. Further, the term includes all meanings that can be recognized by those skilled in the art, and may be appropriately interpreted according to the context.

Target Strand and Non-Target Strand

As used herein, the terms "target strand" and "non-target strand" are used to specify each strand when describing that a CRISPR/Cas9 complex acts on a double-stranded nucleic acid as a target nucleic acid. Basically, "target strand" and "non-target strand" refer to each strand of a double-stranded nucleic acid, and have complementary sequences to each other. Here, "non-target strand" refers to a strand in which a protospacer adjacent motif (PAM) recognized by the Cas9 protein is located, and "target strand" refers to a strand to which a guide RNA binds complementarily. In other words, when the CRISPR/Cas9 complex cleaves a target nucleic acid, 1) the Cas9 protein recognizes a PAM sequence present in a non-target strand, and 2) a portion of the guide RNA that is designed to target a target sequence (a so-called guide domain) forms a duplex by complementarily binding to the target strand, thereby activating the nucleic acid cleavage function of the CRISPR/Cas9 complex.

Further, the term includes all meanings that can be recognized by those skilled in the art, and may be appropriately interpreted according to the context.

Target Sequence and Non-Target Sequence

As used herein, "target sequence" refers to a particular sequence that a CRISPR/Cas complex recognizes to cleave a target gene or target nucleic acid. The target sequence may be appropriately selected according to the purpose thereof. Specifically, a "target sequence" is a sequence included in a target gene or target nucleic acid sequence, and the term refers to a sequence that is complementary to a guide domain sequence included in a guide RNA or an engineered guide RNA provided in the present specification. In general, the guide domain sequence is determined in consideration of a target gene or target nucleic acid sequence and a PAM sequence recognized by an effector protein of a CRISPR/Cas system. "Target sequence" refers to a sequence included in the target strand which complementarily binds to the guide RNA of the CRISPR/Cas complex.

As used herein, "non-target sequence" refers to a sequence having complementarity to the target sequence. The non-target sequence is a sequence included in the non-target strand, and when present as a double strand, it is generally bound to the target sequence. In addition, the non-target sequence is adjacent to the PAM sequence.

The term includes all meanings that can be recognized by those skilled in the art, and may be appropriately interpreted according to the context.

Vector

As used herein, "vector" collectively refers to all materials capable of carrying a genetic material into a cell, unless otherwise specified. For example, a vector may be a DNA molecule including a genetic material of interest, for example, a nucleic acid encoding a Cas protein of the CRISPR/Cas system, and/or a nucleic acid encoding a guide RNA, but is not limited thereto. The term includes all meanings that can be recognized by those skilled in the art, and may be appropriately interpreted according to the context.

Non-Homologous End Joining (NHEJ)

As used herein, "non-homologous end joining (NHEJ)" refers to a method of restoring or repairing a double-stranded break in DNA by joining together both ends of a cleaved double or single strand, and generally, the broken double strand is recovered when two compatible ends formed by a double-stranded break (for example, cleavage) repeatedly come into frequent contact to fully join the two ends. NHEJ is a restoring method that can occur at any stage of the cell cycle, and occurs primarily when there is no homologous gene used as a template in the cell, such as in the G1 phase. The process of repairing damaged genes or nucleic acids using NHEJ may result in the insertion and/or deletion of a partial nucleic acid sequence (indel) at an NHEJ repair site. The term includes all meanings that can be recognized by those skilled in the art, and may be appropriately interpreted according to the context.

Homology Directed Repairing (HDR)

As used herein, "homology directed repairing (HDR)" refers to a method through which a damaged gene or nucleic acid can be corrected without error using a homologous sequence as a template to repair or restore the damaged gene or nucleic acid, and generally, to repair or restore damaged DNA, that is, to restore the original information that the cell possesses, the damaged DNA is repaired or restored using the information of an unaltered complementary base sequence or the information of sister chromatids. The most common form of HDR is homologous recombination (HR). HDR is a repair or restoration method that typically occurs primarily during the S or G2/M phase of actively dividing cells.

To repair or restore damaged DNA using HDR, instead of using complementary base sequences or sister chromatids which cells originally possess, an artificially synthesized DNA template may be used using complementary or homologous base sequence information. That is, the damaged DNA may be repaired or restored by providing a nucleic acid template including a complementary or homologous base sequence to cells. In this case, when damaged DNA is repaired or restored by additionally including a nucleic acid sequence or nucleic acid fragment in the nucleic acid template, the additionally included nucleic acid sequence or nucleic acid fragment may be knocked-in into the damaged DNA. The term includes all meanings that can be recognized by those skilled in the art, and may be appropriately interpreted according to the context.

Protospacer Adjacent Motif (PAM)

The CRISPR/Cas9 system has target-specific nucleic acid cleavage activity, but two conditions are required to exhibit such target-specific nucleic acid cleavage activity. First, there must be a base sequence having a certain length, which the Cas9 protein is capable of recognizing in a nucleic acid.

Second, there must be a sequence capable of complementarily binding to a guide domain included in a guide RNA around the base sequence having the certain length. When these two conditions are satisfied to allow 1) the Cas9 protein to recognize the base sequence having a certain length and 2) the guide domain to complementarily bind to the sequence part around the base sequence having a certain length, the nucleic acid cleavage activity is exhibited. In this case, the base sequence having the certain length recognized by the Cas9 protein is called a protospacer adjacent motif (PAM) sequence.

The PAM sequence is a unique sequence determined by the Cas9 protein. When the PAM sequence of the Cas9 protein is known, the PAM sequence may be used to design a CRISPR/Cas9 system which targets nucleic acids of predetermined target sequences surrounding the PAM sequence.

Nuclear Localization Sequence (NLS)

As used herein, "NLS" refers to a peptide having a certain length, which serves as a type of "tag" by being attached to a protein to be transported, or a sequence thereof, when a material outside the cell nucleus is transported into the nucleus by a nuclear transport action. Specifically, the NLS may be an NLS of SV40 virus large T-antigen having an amino acid sequence PKKKRKV (SEQ ID NO: 10); an NLS from a nucleoplasmin (for example, a nucleoplasmin bipartite NLS having a sequence KRPAATKKAGQAKKKK (SEQ ID NO: 69)); a c-myc NLS having an amino acid sequence PAAKRVKLD (SEQ ID NO: 70) or RQRRNELKRSP (SEQ ID NO: 71); an hRNPA1 M9 NLS having a sequence NQSSNFGPMKGGNFGGRSSGPYGGGGQYFAKPRNQGGY (SEQ ID NO: 72); a sequence RMRIZFKNKGKDTAELRRRRVEVSVELRKAKKDEQILKRRNV (SEQ ID NO: 73) of an IBB domain from importin-alpha; sequences VSRKRPRP (SEQ ID NO: 74) and PPKKARED (SEQ ID NO: 75) of a myoma T protein; a sequence PQPKKKPL (SEQ ID NO: 76) of human p53; a sequence SALIKKKKKMAP (SEQ ID NO: 77) of mouse c-abl IV; sequences DRLRR (SEQ ID NO: 78) and PKQKKRK (SEQ ID NO: 79) of an influenza virus NS1; a sequence RKLKKKIKKL (SEQ ID NO: 80) of a hepatitis virus delta antigen; a sequence REKKKFLKRR (SEQ ID NO: 81) of a mouse Mx1 protein; a sequence KRKGDEVDGVDEVAKKKSKK (SEQ ID NO: 82) of a human poly (ADP-ribose) polymerase; or an NLS sequence derived from a sequence RKCLQAGMNLEARKTKK (SEQ ID NO: 83) of a steroid hormone receptor (human) glucocorticoid, but is not limited thereto. As used herein, the term "tag" includes all meanings that can be recognized by those skilled in the art, and may be appropriately interpreted according to the context.

Amino Acid Residue

As used herein, "amino acid residue" refers to a collective term for amino acid moieties other than —H and —OH which are removed when a peptide bond is formed through a condensation reaction as a structural unit of a polypeptide. That is, "amino acid residue" refers to a group other than an atomic group removed during bonding. For example, when a protein consists of a total of 1368 amino acids from the N-terminus to the C-terminus, the protein may be expressed as consisting of 1368 amino acid residues. Specifically, the wild-type SpCas9 protein consists of 1,368 amino acid residues.

For convenience of explanation, amino acid residues (amino acid moieties other than —H and —OH) may be described using general amino acid sequence notation. For example, in the wild-type SpCas9 protein, the 1218th amino acid residue in the direction from the N-terminus to the C-terminus may be expressed as glycine (Gly, G).

Amino Acid Residue and Mutation Notations

In the present disclosure, when describing what a specific amino acid residue in the SpCas9 protein is, the amino acid may be described using the position of the specific amino acid residue and the one-letter amino acid notation. For example, when the order of amino acid residues in the direction from the N-terminus to the C-terminus of a protein is expressed with numbers, if the 1218th amino acid residue is glycine (Gly; G), the protein can be said to include the amino acid residue "G1218."

In the present disclosure, when describing a mutation in a SpCas9 variant related to a wild-type SpCas9 protein, the mutation may be described using the amino acid residue at which the mutation occurs and the amino acid which is substituted for the corresponding position. For example, when a wild-type SpCas9 protein includes a G1218 amino acid residue and the 1218th amino acid in a SpCas9 variant includes lysine (Lys, K), the SpCas9 variant may be described as including a G1218K mutation. That is, a variant in which the 1218th amino acid, glycine, in the amino acid sequence constituting the wild-type SpCas9 protein is substituted with lysine is represented by "G1218K."

Furthermore, when a SpCas9 variant simultaneously includes G1218K, E1219V, and R1335Q mutations, the SpCas9 variant may be expressed as including "G1218K/E1219V/R1335Q" mutation.

Further, the term includes all meanings that can be recognized by those skilled in the art, and may be appropriately interpreted according to the context.

CRISPR/Cas System

Overview of CRISPR/Cas System

The CRISPR/Cas system is a type of immune system found in prokaryotic organisms and includes a Cas protein and guide RNA. The detailed configuration of the Cas protein, or guide RNA, is described in detail in a published document WO2018/231018 (International Publication Number). As used herein, the term "Cas protein" is a general term for a nuclease which may be interpreted as being used in the CRISPR/Cas system. Hereinafter, the DNA cleavage process of the most commonly used CRISPR/Cas9 system will be briefly described.

Cas9 Protein

In the CRISPR/Cas9 complex, a protein with nuclease activity that cleaves nucleic acids is called a Cas9 protein. The Cas9 protein corresponds to Class 2, Type II in the CRISPR/Cas system classification, and examples thereof include Cas9 proteins derived from *Streptococcus pyogenes*, *Streptococcus thermophilus*, *Streptococcus* sp., *Streptomyces* pristinaespiralis, *Streptomyces viridochromogenes*, *Streptomyces viridochromogenes*, *Streptosporangium roseum*, and *Streptosporangium roseum*, and the like. The present disclosure discloses a variant of a *Streptococcus pyogenes*-derived Cas9 protein.

Guide RNA

In the CRISPR/Cas9 complex, an RNA having a function of guiding the CRISPR/Cas9 complex to recognize a specific sequence included in a target nucleic acid is referred to as a guide RNA. The guide RNA may be generally described in the art as consisting of crRNA and tracrRNA.

In addition, the component of the guide RNA may be broadly divided functionally into 1) a scaffold component and 2) a guide domain component. Generally, the scaffold component includes tracrRNA and direct repeat, and the guide domain component and a portion of the direct repeat are included in the crRNA. The scaffold component is a part which interacts with the Cas9 protein, and is a part which can interact with the Cas9 protein to form a complex. The scaffold component is determined by the type of microorganism from which the Cas9 protein is derived. The guide domain component is a part capable of complementarily binding to a nucleotide sequence part with a certain length in a target nucleic acid, and may have a length of about 15 to 30 nt. The guide domain component is an artificially variable sequence, and is determined by a target nucleotide sequence of interest.

Process in which CRISPR/Cas9 Complex Cleaves Target Nucleic Acid

When the CRISPR/Cas9 complex comes into contact with the target nucleic acid, the Cas9 protein recognizes a nucleotide sequence with a certain length (PAM sequence), and a portion of the guide RNA (the guide domain component) complementarily binds to a target sequence (a part of the double strand of the target nucleic acid, which complementarily binds to a non-target sequence, which is a part adjacent to the PAM sequence), and the target nucleic acid is cleaved by the CRISPR/Cas9 complex. In this case, the nucleotide sequence with a certain length, which the Cas9 protein recognizes, is referred to as a protospacer-adjacent motif (PAM) sequence, which is determined by the type and origin of the Cas9 protein. For example, the *Streptococcus pyogenes*-derived Cas9 protein may recognize the 5'-NGG-3' sequence in the target nucleic acid. In this case, N is one of adenosine (A), thymidine (T), cytidine (C), and guanosine (G). In order for the CRISPR/Cas9 complex to cleave the target nucleic acid, the guide domain component of the guide RNA must complementarily bind to the target sequence (a part which complementarily binds to the non-target sequence which is a part adjacent to the PAM sequence in the double strand of the target nucleic acid). Therefore, the guide domain component is designed and used according to the sequence of the target nucleic acid, specifically, the sequence adjacent to the PAM sequence. When the CRISPR/Cas9 complex cleaves the target nucleic acid, any position in a double-stranded region including the PAM sequence part of the target nucleic acid and/or a sequence which complementarily binds to the guide domain is cleaved.

*Streptococcus pyogenes*-Derived Cas9 Protein

A *Streptococcus pyogenes*-derived Cas9 protein is also referred to as SpCas9, and is one of the orthologs of the Cas9 protein. The wild-type SpCas9 protein may recognize the 5'-NGG-3' sequence in the target nucleic acid as a PAM sequence. The amino acid sequence of the wild-type SpCas9 protein is as follows:

```
                                    (SEQ ID NO: 1)
RKMIAKSEQEIGKATAKYFFYSNIMNFFKTEITLANGEIRKRPLIETNG

ETGEIVWDKGRDFATVRKVLSMPQVNIVKKTEVQTGGFSKESILPKRNS

DKLIARKKDWDPKKYGGFDSPTVAYSVLVVAKVEKGKSKKLKSVKELLG

ITIMERSSFEKNPIDFLEAKGYKEVKKDLIIKLPKYSLFELENGRKRML

ASAGELQKGNELALPSKYVNFLYLASHYEKLKGSPEDNEQKQLFVEQHK

HYLDEIIEQISEFSKRVILADANLDKVLSAYNKHRDKPIREQAENIIHL

FTLTNLGAPAAFKYFDTTIDRKRYTSTKEVLDATLIHQSITGLYETRID

LSQLGGD-3'.
```

Limitations of Wild-Type SpCas9 Protein

The wild-type SpCas9 protein has an advantage of having higher gene editing efficiency than other types of Cas9 proteins. However, since a PAM sequence that wild-type SpCas9 is capable of recognizing is limited to 5'-NGG-3', nucleic acid sequences cannot be edited at positions which do not have a 5'-NGG-3' PAM sequence nearby. That is, there is a problem in that the locations where gene editing can be performed using wild-type SpCas9 are limited. To overcome these problems, various attempts have been made in the art to produce a SpCas9 protein capable of recognizing a PAM sequence other than 5'-NGG-3', and new mutants have been discovered accordingly. The present disclosure discloses a new SpCas9 variant.

SpCas9 Variant

Overview—SpCas9 Variant

The present disclosure discloses a SpCas9 variant. The SpCas9 variant has an amino acid sequence that differs partially from that of the wild-type SpCas9 protein. As a specific example, when the amino acid sequences of the SpCas9 variant and the wild-type SpCas9 protein are compared, the SpCas9 variant and the wild-type SpCas9 protein differ in 6, 7, or 8 amino acid residues.

The SpCas9 variant may recognize a PAM sequence different from that of the wild-type SpCas9 protein. As a specific example, the SpCas9 variant may recognize a 5'-NGG-3' sequence.

As an example, the SpCas9 variant may cleave a target sequence adjacent to a 5'-NGN-3' sequence. As another example, the SpCas9 variant may cleave a target sequence adjacent to a 5'-NNG-3' sequence. As another example, the SpCas9 variant may be PAMless.

Mutation Region I: Mutations at G1218, E1219, R1333, R1335, and T1337 Amino Acid Residues The SpCas9 variant differs in at least one amino acid residue of the G1218, E1219, R1333, R1335, and T1337 amino acid residues when compared to the wild-type SpCas9 protein. The G1218, E1219, R1333, R1335, and T1337 amino acid residues are amino acid residues which are involved in the recognition of the SpCas9 protein to the PAM sequence.

The SpCas9 variant differs in at least one amino acid residue of the G1218 and E1219 amino acid residues when compared to the wild-type SpCas9 protein. The G1218 and E1219 amino acid residues are amino acid residues related to the capability of hydrophobic interactions with a portion of the ribose of the PAM sequence located in the genome.

Furthermore, the SpCas9 variant differs in at least one amino acid residue of the R1333, R1335, and T1337 amino acid residues when compared to the wild-type SpCas9 protein. The R1333, R1335, and T1337 amino acid residues are amino acid residues involved in the capability to directly recognize and bind to the PAM sequence.

Mutation Region II: Mutations at L1111, D1135, and A1322 Amino Acid Residues

Further, the SpCas9 variant differs in L1111, D1135, and A1322 amino acid residues when compared to the wild-type SpCas9 protein. The SpCas9 variant includes the L1111R/D1135V/A1322R mutation when compared to the wild-type SpCas9 protein.

The L1111R/D1135V/A1322R mutation is a mutated portion common with a known mutant Nureki-NG Cas9 protein. The amino acid sequence of the Nureki-NG Cas9 protein is as follows:

```
                                       (SEQ ID NO: 2)
RKMIAKSEQEIGKATAKYFFYSNIMNFFKTEITLANGEIRKRPLIETNG

ETGEIVWDKGRDFATVRKVLSMPQVNIVKKTEVQTGGFSKESIRPKRNS

DKLIARKKDWDPKKYGGFVSPTVAYSVLVVAKVEKGKSKKLKSVKELLG

ITIMERSSFEKNPIDFLEAKGYKEVKKDLIIKLPKYSLFELENGRKRML

ASARFLQKGNELALPSKYVNFLYLASHYEKLKGSPEDNEQKQLFVEQHK

HYLDEIIEQISEFSKRVILADANLDKVLSAYNKHRDKPIREQAENIIHL

FTLTNLGAPRAFKYFDTTIDRKVYRSTKEVLDATLIHQSITGLYETRID

LSQLGGD-3'.
```

Hereinafter, specific examples of the spCas9 variants will be described in detail.

Example 1 of SpCas9 Variant-L1111R/D1135V/G1218K/E1219V/A1322R/R1335Q

As an embodiment, the SpCas9 variant may include, when compared to the wild-type SpCas9 protein, L1111R, D1135V, and A1322R mutations, and may include mutations in which the G1218, E1219, and R1335 amino acid residues are substituted with other amino acids. As a specific example, the SpCas9 variant may include L1111R/D1135V/G1218K/E1219V/A1322R/R1335Q mutation.

As a specific example, the SpCas9 variant includes the following substitutions compared to the wild type SpCas9 protein:

- a substitution of the 1111th amino acid residue from leucine (Leu, L) to arginine (Arg, R);
- a substitution of the 1135th amino acid residue from aspartic acid (Asp, D) to valine (Val, V);
- a substitution of the 1218th amino acid residue from glycine (Gly, G) to lysine (Lys, K);
- a substitution of the 1219th amino acid residue from glutamic acid (Glu, E) to valine (Val, V);
- a substitution of the 1322nd amino acid residue from alanine (Ala, A) to arginine (Arg, R); and
- a substitution of the 1335th amino acid residue from arginine (Arg, R) to glutamine (Gln, Q) in a direction from the N-terminus to the C-terminus of the wild type SpCas9 protein.

The SpCas9 variant including the L1111R/D1135V/G1218K/E1219V/A1322R/R1335Q mutation may recognize PAM sequence which is 5'-NGN-3'. As a specific example, the SpCas9 variant including the L1111R/D1135V/G1218K/E1219V/A1322R/R1335Q mutation may cleave a non-target sequence and/or a target sequence adjacent to PAM sequence which is 5'-NGN-3'.

As a specific example, the amino acid sequence of the SpCas9 variant including the L1111R/D1135V/G1218K/E1219V/A1322R/R1335Q mutation may be as follows: 5'-

```
                                       (SEQ ID NO: 3)
IAKSEQEIGKATAKYFFYSNIMNFFKTEITLANGEIRKRPLIETNGETG

EIVWDKGRDFATVRKVLSMPQVNIVKKTEVQTGGFSKESIRPKRNSDKL

IARKKDWDPKKYGGFVSPTVAYSVLVVAKVEKGKSKKLKSVKELLGITI

MERSSFEKNPIDFLEAKGYKEVKKDLIIKLPKYSLFELENGRKRMLASA

KVLQKGNELALPSKYVNFLYLASHYEKLKGSPEDNEQKQLFVEQHKHYL

DEIIEQISEFSKRVILADANLDKVLSAYNKHRDKPIREQAENIIHLFTL

TNLGAPRAFKYFDTTIDRKQYTSTKEVLDATLIHQSITGLYETRIDLSQ

LGGD-3'.
```

As another specific example, the SpCas9 variant including the L1111R/D1135V/G1218K/E1219V/A1322R/R1335Q mutation may comprise an amino acid sequence having at least 80%, for example, 80% to 85%, 85% to 90%, 90% to 95%, or 95% to 100%, identity to an amino acid sequence of SEQ ID NO: 3.

Example 2 of SpCas9 Variant-L1111R/D1135V/G1218Q/E1219Q/A1322R/R1333P/T1337L As an embodiment, the SpCas9 variant may include, when compared to the wild-type SpCas9 protein, L1111R, D1135V, and A1322R mutations, and may include mutations in which the G1218, E1219, R1333, and T1337 amino acid residues are substituted with other amino acids. As a specific example, the SpCas9 variant may include L1111R/D1135V/G1218Q/E1219Q/A1322R/R1333P/T1337L mutation.

As a specific example, the SpCas9 variant includes the following substitutions compared to the wild type SpCas9 protein:

- a substitution of the 1111th amino acid residue from leucine (Leu, L) to arginine (Arg, R);
- a substitution of the 1135th amino acid residue from aspartic acid (Asp, D) to valine (Val, V);
- a substitution of the 1218th amino acid residue from glycine (Gly, G) to glutamine (Gln, Q);
- a substitution of the 1219th amino acid residue from glutamic acid (Glu, E) to glutamine (Gln, Q);
- a substitution of the 1322nd amino acid residue from alanine (Ala, A) to arginine (Arg, R);
- a substitution of the 1333rd amino acid residue from arginine (Arg, R) to proline (Pro, P); and
- a substitution of the 1337th amino acid residue from threonine (Thr, T) to leucine (Leu, L) in a direction from the N-terminus to the C-terminus of the wild type SpCas9 protein.

The SpCas9 variant including the L1111R/D1135V/G1218Q/E1219Q/A1322R/R1333P/T1337L mutation may recognize a PAM sequence which is 5'-NNG-3'. As a specific example, the SpCas9 variant including the L1111R/D1135V/G1218Q/E1219Q/A1322R/R1333P/T1337L mutation may cleave a non-target sequence and/or a target sequence adjacent to a PAM sequence which is 5'-NNG-3'.

As a specific example, the amino acid sequence of the SpCas9 variant including the L1111R/D1135V/G1218Q/E1219Q/A1322R/R1333P/T1337L mutation may be as follows:

```
                                        (SEQ ID NO: 4)
5'-IAKSEQEIGKATAKYFFYSNIMNFFKTEITLANGEIRKRPLIETNG

ETGEIVWDKGRDFATVRKVLSMPQVNIVKKTEVQTGGFSKESIRPKRNS

DKLIARKKDWDPKKYGGFVSPTVAYSVLVVAKVEKGKSKKLKSVKELLG

ITIMERSSFEKNPIDFLEAKGYKEVKKDLIIKLPKYSLFELENGRKRML

ASAQQLQKGNELALPSKYVNFLYLASHYEKLKGSPEDNEQKQLFVEQHK

HYLDEIIEQISEFSKRVILADANLDKVLSAYNKHRDKPIREQAENIIHL

FTLTNLGAPRAFKYFDTTIDPKRYLSTKEVLDATLIHQSITGLYETRID

LSQLGGD-3'.
```

As another specific example, the SpCas9 variant including the L1111R/D1135V/G1218Q/E1219Q/A1322R/R1333P/T1337L mutation may comprise an amino acid sequence having at least 80%, for example, 80% to 85%, 85% to 90%, 90% to 95%, or 95% to 100%, sequence identity or sequence similarity with an amino acid sequence of SEQ ID NO: 4.

Example 3 of SpCas9 Variant-L1111R/D1135V/G1218R/E1219F/A1322R/R1333G/R1335H/T1337C As an embodiment, the SpCas9 variant may include, when compared to the wild-type SpCas9 protein, L1111R, D1135V, and A1322R mutations, and may include mutations in which the G1218, E1219, R1333, R1335, and T1337 amino acid residues are substituted with other amino acids. As a specific example, the SpCas9 variant may include L1111R/D1135V/G1218R/E1219F/A1322R/R1333G/R1335H/T1337C mutation.

As a specific example, the SpCas9 variant includes the following substitutions compared to the wild type SpCas9 protein:

- a substitution of the 1111th amino acid residue from leucine (Leu, L) to arginine (Arg, R);
- a substitution of the 1135th amino acid residue from aspartic acid (Asp, D) to valine (Val, V);
- a substitution of the 1218th amino acid residue from glycine (Gly, G) to arginine (Arg, R);
- a substitution of the 1219th amino acid residue from glutamic acid (Glu, E) to phenylalanine (Phe, F);
- a substitution of the 1322nd amino acid residue from alanine (Ala, A) to arginine (Arg, R);
- a substitution of the 1333rd amino acid residue from arginine (Arg, R) to glycine (Gly, G); and
- a substitution of the 1337th amino acid residue from threonine (Thr, T) to cysteine (Cys, C) in a direction from the N-terminus to the C-terminus of the wild type SpCas9 protein.

The SpCas9 variant including the L1111R/D1135V/G1218R/E1219F/A1322R/R1333G/R1335H/T1337C mutation may be PAMless. As a specific example, the SpCas9 variant including the L1111R/D1135V/G1218R/E1219F/A1322R/R1333G/R1335H/T1337C mutation may target and cleave a desired target sequence regardless of the specific PAM sequence.

As a specific example, the amino acid sequence of the SpCas9 variant including the L1111R/D1135V/G1218R/E1219F/A1322R/R1333G/R1335H/T1337C mutation may be as follows:

```
                                        (SEQ ID NO: 5)
5'-IAKSEQEIGKATAKYFFYSNIMNFFKTEITLANGEIRKRPLIETNG

ETGEIVWDKGRDFATVRKVLSMPQVNIVKKTEVQTGGFSKESIRPKRNS

DKLIARKKDWDPKKYGGFVSPTVAYSVLVVAKVEKGKSKKLKSVKELLG

ITIMERSSFEKNPIDFLEAKGYKEVKKDLIIKLPKYSLFELENGRKRML

ASARFLQKGNELALPSKYVNFLYLASHYEKLKGSPEDNEQKQLFVEQHK

HYLDEIIEQISEFSKRVILADANLDKVLSAYNKHRDKPIREQAENIIHL

FTLTNLGAPRAFKYFDTTIDRKQYTSTKEVLDATLIHQSITGLYETRID

LSQLGGD-3'.
```

As another specific example, the SpCas9 variant including the L1111R/D1135V/G1218R/E1219F/A1322R/R1333G/R1335H/T1337C mutation may comprise an amino acid sequence having at least 80%, for example, 80% to 85%, 85% to 90%, 90% to 95%, or 95% to 100%, sequence identity or sequence similarity with an amino acid sequence of SEQ ID NO: 5.

Example 4 of SpCas9 Variant-L1111R/D1135V/G1218M/E1219T/A1322R/R1333P/R1335Y/T1337L As an embodiment, the SpCas9 variant may include, when compared to the wild-type SpCas9 protein, L1111R, D1135V, and A1322R mutations, and may include mutations in which the G1218, E1219, R1333, R1335, and T1337 amino acid residues are substituted with other amino acids.

As a specific example, the SpCas9 variant may include L1111R/D1135V/G1218M/E1219T/A1322R/R1333P/R1335Y/T1337L mutation.

As a specific example, the SpCas9 variant include the following substitutions compared to the wild type SpCas9 protein:

- a substitution of the 1111th amino acid residue from leucine (Leu, L) to arginine (Arg, R);
- a substitution of the 1135th amino acid residue from aspartic acid (Asp, D) to valine (Val, V);
- a substitution of the 1218th amino acid residue from glycine (Gly, G) to methionine (Met, M);
- a substitution of the 1219th amino acid residue from glutamic acid (Glu, E) to threonine (Thr, T);
- a substitution of the 1322nd amino acid residue from alanine (Ala, A) to arginine (Arg, R);
- a substitution of the 1333rd amino acid residue from arginine (Arg, R) to proline (Pro, P);
- a substitution of the 1335th amino acid residue from arginine (Arg, R) to tyrosine (Tyr, Y); and
- a substitution of the 1337th amino acid residue from threonine (Thr, T) to leucine (Leu, L) in a direction from the N-terminus to the C-terminus of the wild type SpCas9 protein.

The SpCas9 variant including the L1111R/D1135V/G1218M/E1219T/A1322R/R1333P/R1335Y/T1337L mutation may be PAMless. As a specific example, the SpCas9 variant including the L1111R/D1135V/G1218M/E1219T/A1322R/R1333P/R1335Y/T1337L mutation may target and cleave a desired target sequence regardless of the specific PAM sequence.

As a specific example, the amino acid sequence of the SpCas9 variant including the L1111R/D1135V/G1218M/E1219T/A1322R/R1333P/R1335Y/T1337L mutation may be as follows:

```
                                              (SEQ ID NO: 6)
5'-IAKSEQEIGKATAKYFFYSNIMNFFKTEITLANGEIRKRPLIETNG
ETGEIVWDKGRDFATVRKVLSMPQVNIVKKTEVQTGGFSKESIRPKRNS
DKLIARKKDWDPKKYGGFVSPTVAYSVLVVAKVEKGKSKKLKSVKELLG
ITIMERSSFEKNPIDFLEAKGYKEVKKDLIIKLPKYSLFELENGRKRML
ASAMTLQKGNELALPSKYVNFLYLASHYEKLKGSPEDNEQKQLFVEQHK
HYLDEIIEQISEFSKRVILADANLDKVLSAYNKHRDKPIREQAENIIHL
FTLTNLGAPRAFKYFDTTIDPKYYLSTKEVLDATLIHQSITGLYETRID
LSQLGGD-3'.
```

As another specific example, the SpCas9 variant including the L1111R/D1135V/G1218M/E1219T/A1322R/R1333P/R1335Y/T1337L mutation may comprise an amino acid sequence having at least 80%, for example, 80% to 85%, 85% to 90%, 90% to 95%, or 95% to 100%, sequence identity or sequence similarity with an amino acid sequence of SEQ ID NO: 6.

Example of SpCas9 Variant-Fusion with NLS

As an exemplary embodiment, the SpCas9 variant may further include a nuclear localization sequence (NLS).

As a specific example, an NLS may be fused to the N-terminus of the SpCas9 variant. As another specific example, an NLS may be fused to the C-terminus of the SpCas9 variant. As still another specific example, an NLS may be fused to the N-terminus and C-terminus of the SpCas9 variant. As yet another specific example, the amino acid sequence of the SpCas9 variant may comprise the sequence of the NLS.

In this case, the NLS refers to a peptide having a certain length, which serves as a type of "tag" by being attached to a protein to be transported, or a sequence thereof, when a material outside the cell nucleus is transported into the nucleus by a nuclear transport action. Accordingly, as a specific example, the SpCas9 variant to which the NLS is fused is more likely to be transported from the outside to the inside of the cell nucleus than the SpCas9 variant to which the NLS is not fused.

The NLS may be any one of those exemplified in the NLS paragraph in <<Definitions of terms>>. As a specific example, the amino acid sequence of the NLS may be PKKKRKV (SEQ ID NO: 10).

CRISPR/Cas9 Composition Including SpCas9 Variant

Overview

The present disclosure discloses a CRISPR/Cas9 composition. The CRISPR/Cas9 composition includes 1) the SpCas9 variant or a nucleic acid encoding the same and 2) a guide RNA or a nucleic acid encoding the same. In this case, the CRISPR/Cas9 composition may be used in a method for editing genes. As a specific example, the CRISPR/Cas9 composition may be used when genes are edited by targeting a sequence adjacent to PAM sequence other than 5'-NGG-3'.

Guide RNA

The guide RNA may include crRNA and tracrRNA.

The crRNA may include a guide domain and a direct repeat. The guide domain and the direct repeat may be sequentially linked from 5' to 3' of the crRNA.

The guide domain is a part capable of complementarily binding to a nucleotide sequence part with a certain length in a target nucleic acid. The guide domain is an artificially variable sequence, and is determined by a target nucleotide sequence of interest.

The tracrRNA may form a CRISPR/Cas9 complex by interacting with the SpCas9 variant together with the direct repeat of crRNA.

As a specific example, the sequence of the direct repeat may include the following sequence: 5'-GUUUUAGAGCUA-3' (SEQ ID NO: 7). As a specific example, the direct repeat may include a nucleic acid sequence having at least 80%, for example, 80% to 85%, 85% to 90%, 90% to 95%, or 95% to 100%, sequence identity or sequence similarity with a sequence of SEQ ID NO: 7.

As a specific example, the tracrRNA may include the following sequence: 5'-UAGCAAGUUAAAAUAAGGCUAGUCCGUUAUCAACUUGAAAAAGUGGCACCGAGUCGGUGC-3' (SEQ ID NO: 8). As a specific example, the tracrRNA may include a nucleic acid sequence having at least 80%, for example, 80% to 85%, 85% to 90%, 90% to 95%, or 95% to 100%, sequence identity or sequence similarity with a sequence of SEQ ID NO: 8.

As a specific example, the guide RNA may include the following sequence: 5'-GUUUUAGAGCUAGAAAUAGCAAGUUAAAAUAAGGCUAGUCCGUUAUCAACUU GAAAAAGUGGCACCGAGUCGGUGCUUUUUU-3' (SEQ ID NO: 9). As a specific example, the guide RNA may include a nucleic acid sequence having at least 80%, for example, 80% to 85%, 85% to 90%, 90% to 95%, or 95% to 100%, sequence identity or sequence similarity with a sequence of SEQ ID NO: 9.

As a specific example, the guide RNA may be in the form of single guide RNA (sgRNA). In this case, the single guide RNA may be a single guide RNA in which a crRNA and a tracrRNA are linked to each other via a linker (for example, a linker of a 5'-GAAA-3' or 5'-GA-3' sequence).

As another specific example, the guide RNA may be one in which the crRNA and the tracrRNA are not linked to each other.

Configurational Form 1 of Composition—Vector

As a specific example, the CRISPR/Cas9 composition may include a vector including a nucleic acid encoding the SpCas9 variant and/or a nucleic acid encoding the guide RNA. The vector is described in detail in the following <<Configurational Form of CRISPR/Cas9 Composition-Vector>> paragraph.

Configurational Form 2 of Composition—RNP

As a specific example, the CRISPR/Cas9 composition may include a ribonucleoprotein (RNP) formed by the binding of a SpCas9 mutant protein and a guide RNA. This may mean a form of a CRISPR/Cas9 complex formed by allowing the direct repeat of the guide RNA and tracrRNA to interact with the SpCas9 variant.

Configurational Form 3 of Composition—Other

As a specific example, the CRISPR/Cas9 composition may include any one or more of the following configurations 1) to 4): 1) a SpCas9 variant and a guide RNA; 2) a nucleic acid encoding the SpCas9 variant and a guide RNA; 3) a nucleic acid encoding the SpCas9 variant and a nucleic acid encoding the guide RNA; and 4) the SpCas9 variant and a nucleic acid encoding the guide RNA.

Component Example 1 of Composition-L1111R/D1135V/G1218K/E1219V/A1322R/R1335Q

As an embodiment, the CRISPR/Cas9 composition may include a SpCas9 variant described in the paragraph <<Example 1 of SpCas9 variant-L1111R/D1135V/G1218K/E1219V/A1322R/R1335Q>> or a nucleic acid encoding the same. The CRISPR/Cas9 composition may include a guide RNA which targets a target sequence which complementarily binds to a non-target sequence adjacent to a PAM sequence which is 5'-NGN-3' or a nucleic acid encoding the guide RNA.

As a specific example, the guide domain of the guide RNA may include a sequence complementary to a target sequence which complementarily binds to a non-target sequence adjacent to a PAM sequence which is 5'-NGN-3'. As a specific example, the guide domain may complementarily bind to a target sequence which complementarily binds to a non-target sequence adjacent to a PAM sequence which is 5'-NGN-3'.

As a specific example, the guide domain may have a length of 11nt, 12nt, 13nt, 14nt, 15nt, 16nt, 17nt, 18nt, 19nt, 20nt, 21nt, 22nt, 23nt, 24nt, 25nt, 27nt, 28nt, 29nt, or 30nt. As an exemplary embodiment, the guide domain may have a length within a range between any two numbers selected from the immediately preceding sentence. For example, the guide domain may have a length of 18nt to 22nt.

As a specific example, the amino acid sequence of the SpCas9 variant may be a sequence of SEQ ID NO: 3.

As another specific example, the SpCas9 variant may have an amino acid sequence comprising at least 80%, for example, 80% to 85%, 85% to 90%, 90% to 95%, or 95% to 100%, sequence identity or sequence similarity with an amino acid sequence of SEQ ID NO: 3.

Component Example 2 of Composition-L1111R/D1135V/G1218Q/E1219Q/A1322R/R1333P/T1337L As an embodiment, the CRISPR/Cas9 composition may include a SpCas9 variant described in the paragraph <<Example 2 of SpCas9 variant-L1111R/D1135V/G1218Q/E1219Q/A1322R/R1333P/T1337L>> or a nucleic acid encoding the same. The CRISPR/Cas9 composition may include a guide RNA which targets a target sequence which complementarily binds to a non-target sequence adjacent to PAM sequence which is 5'-NNG-3' or a nucleic acid encoding the guide RNA.

As a specific example, the guide domain of the guide RNA may include a sequence complementary to a target sequence which complementarily binds to a non-target sequence adjacent to a PAM sequence which is 5'-NNG-3'. As a specific example, the guide domain may complementarily bind to a target sequence which complementarily binds to a non-target sequence adjacent to a PAM sequence which is 5'-NNG-3'.

As a specific example, the guide domain may have a length of 11nt, 12nt, 13nt, 14nt, 15nt, 16nt, 17nt, 18nt, 19nt, 20nt, 21nt, 22nt, 23nt, 24nt, 25nt, 27nt, 28nt, 29nt, or 30nt. As an exemplary embodiment, the guide domain may have a length within a range between any two numbers selected from the immediately preceding sentence. For example, the guide domain may have a length of 18nt to 22nt.

As a specific example, the amino acid sequence of the SpCas9 variant may be a sequence of SEQ ID NO: 4.

As another specific example, the SpCas9 variant may have an amino acid sequence comprising at least 80%, for example, 80% to 85%, 85% to 90%, 90% to 95%, or 95% to 100%, sequence identity or sequence similarity with an amino acid sequence of SEQ ID NO: 4.

Component Example 3 of Composition-L1111R/D1135V/G1218R/E1219F/A1322R/R1333G/R1335H/T1337C As an embodiment, the CRISPR/Cas9 composition may include a SpCas9 variant described in the paragraph <<Example 3 of SpCas9 variant-L1111R/D1135V/G1218R/E1219F/A1322R/R1333G/R1335H/T1337C>> or a nucleic acid encoding the same. The CRISPR/Cas9 composition may include a guide RNA which targets a target sequence which complementarily binds to a non-target sequence adjacent to PAM sequence which is 5'-NNN-3' or a nucleic acid encoding the guide RNA.

As a specific example, the guide domain of the guide RNA may include a sequence complementary to a target sequence which complementarily binds to a non-target sequence adjacent to PAM sequence which is 5'-NNN-3'. As a specific example, the guide domain may complementarily bind to a target sequence which complementarily binds to a non-target sequence adjacent to PAM sequence which is 5'-NNN-3'.

As a specific example, the guide domain may have a length of 11nt, 12nt, 13nt, 14nt, 15nt, 16nt, 17nt, 18nt, 19nt, 20nt, 21nt, 22nt, 23nt, 24nt, 25nt, 27nt, 28nt, 29nt, or 30nt. As an exemplary embodiment, the guide domain may have a length within a range between any two numbers selected from the immediately preceding sentence. For example, the guide domain may have a length of 18nt to 22nt.

As a specific example, the amino acid sequence of the SpCas9 variant may be a sequence of SEQ ID NO: 5.

As another specific example, the SpCas9 variant may have an amino acid sequence comprising at least 80%, for example, 80% to 85%, 85% to 90%, 90% to 95%, or 95% to 100%, sequence identity or sequence similarity with an amino acid sequence of SEQ ID NO: 5.

Component Example 4 of Composition-L1111R/D1135V/G1218M/E1219T/A1322R/R1333P/R1335Y/T1337L As an embodiment, the CRISPR/Cas9 composition may include a SpCas9 variant described in the paragraph <<Example 4 of SpCas9 variant-L1111R/D1135V/G1218M/E1219T/A1322R/R1333P/R1335Y/T1337L>> or a nucleic acid encoding the same. The CRISPR/Cas9 composition may include a guide RNA which complementarily binds to a non-target sequence adjacent to PAM sequence which is 5'-NNN-3' or a nucleic acid encoding the guide RNA which targets a target sequence.

As a specific example, the guide domain of the guide RNA may include a sequence complementary to a target sequence which complementarily binds to a non-target sequence adjacent to PAM sequence which is 5'-NNN-3'. As a specific example, the guide domain may complementarily bind to a target sequence which complementarily binds to a non-target sequence adjacent to PAM sequence which is 5'-NNN-3'.

As a specific example, the guide domain may have a length of 11nt, 12nt, 13nt, 14nt, 15nt, 16nt, 17nt, 18nt, 19nt, 20nt, 21nt, 22nt, 23nt, 24nt, 25nt, 27nt, 28nt, 29nt, or 30nt. As an exemplary embodiment, the guide domain may have a length within a range between any two numbers selected from the immediately preceding sentence. For example, the guide domain may have a length of 18nt to 22nt.

As a specific example, the amino acid sequence of the SpCas9 variant may be a sequence of SEQ ID NO: 6.

As another specific example, the SpCas9 variant may have an amino acid sequence comprising at least 80%, for example, 80% to 85%, 85% to 90%, 90% to 95%, or 95% to 100%, sequence identity or sequence similarity with an amino acid sequence of SEQ ID NO: 6.

Configurational Form of CRISPR/Cas9 Composition—Vector

The CRISPR/Cas9 composition may include vectors in various forms. The configurations and forms of the vectors which may be included in the CRISPR/Cas9 composition will be described below.

Main Configuration for Gene Editing

As an exemplary embodiment, the vector may include a nucleic acid encoding the SpCas9 variant and/or a nucleic acid encoding the guide RNA.

As a specific example, the SpCas9 and the guide RNA may be a SpCas9 variant and a guide RNA described in the paragraph <<Component Example 1 of composition-L1111R/D1135V/G1218K/E1219V/A1322R/R1335Q>>. As a specific example, the SpCas9 variant and the guide RNA may be a SpCas9 variant and a guide RNA described in the paragraph <<Example 2 of SpCas9 variant-L1111R/D1135V/G1218Q/E1219Q/A1322R/R1333P/T1337L>>. As a specific example, the SpCas9 variant and the guide RNA may be a SpCas9 variant and a guide RNA described in the paragraph <<Example 3 of SpCas9 variant-L1111R/D1135V/G1218R/E1219F/A1322R/R1333G/R1335H/T1337C>. As a specific example, the SpCas9 variant and the guide RNA may be a SpCas9 variant and a guide RNA described in the paragraph <<Example 4 of SpCas9 variant-L1111R/D1135V/G1218M/E1219T/A1322R/R1333P/R1335Y/T1337L>>.

Component for Knock-In

As an exemplary embodiment, the vector may include a component for knock-in. In this case, the vector may include a donor. The donor may refer to a nucleic acid sequence that helps restoring a target gene damaged by a gene editing process or a target nucleic acid damaged by a gene editing process through homology-directed repair (HDR) according to a gene editing process. In this case, the donor may include a nucleic acid sequence for insertion into the target gene or nucleic acid.

As a specific example, the donor may include a nucleic acid sequence (homology arm) having homology to a partial base sequence in the 5' direction (upstream) and/or 3' direction (downstream) at a position where the nucleic acid sequence is to be inserted, for example, at the cleavage site of the damaged target nucleic acid. In this case, the nucleic acid sequence to be inserted may be located between a nucleic acid sequence having homology to a base sequence in the 5' direction and a nucleic acid sequence having homology to a base sequence in the 3' direction, centered on the cleaved site of the target. In this case, a nucleic acid sequence having homology may have at least 50%, 55%, 60%, 65%, 70%, 75%, 80%, 85%, 90% or 95% or more homology or may have complete homology to a base sequence(s) in the 5' direction (upstream) and/or 3' direction (downstream) of the target nucleic acid. In this case, the size of each homology arm may be designed to any length determined to be appropriate by those skilled in the art.

Additional Components for Vector Expression

As a specific example, the vector may additionally include other components required to express the SpCas9 variant and/or guide RNA in cells.

For example, the other additional configurations may include expression control elements, selection elements, and the like.

Examples of the expression control element include a promoter, an enhancer, a polyadenylation signal, a Kozak consensus sequence, an inverted terminal repeat (ITR), a long terminal repeat (LTR), a terminator, an internal ribosome entry site (IRES), a 2A self-cleaving peptide, a replication origin, or the like.

Here, the promoter sequence may be designed differently depending on the corresponding RNA transcription factor or expression environment, and is not limited as long as the promoter sequence can appropriately express the element of the CRISPR/Cas system in the cell. For example, the promoter may be one of an SV40 initial promoter, a mouse mammary tumor virus long terminal repeat (LTR) promoter, an adenovirus major late promoter (Ad MLP), a herpes simplex virus (HSV) promoter, a cytomegalovirus (CMV) promoter such as a CMV immediate early promoter region (CMVIE), a Rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31 (17)), a human H1 promoter (H1), and 7SK. As a specific example, the vector may include a CMV promoter. In this case, the sequence of the CMV promoter may be
5'-CGATGTACGGGCCAGATATACGCGTTGACATTGA-
TTATTGACTAGTTATTAATAG TAATCAATTACGGG-
GTCATTAGTTCATAGCCCATATATGGAGTTCCGCGT-
TACAT AACTTACGGTAAATGGCCCGCCTGGCTGAC-
CGCCCAACGACCCCCGCCCATTG ACGTCAATAAT-
GACGTATGTTCCCATAGTAACGCCAATAGGGACT-
TTCCATTGAC GTCAATGGGTGGACTATTTACGGTA-
AACTGCCCACTTGGCAGTACATCAAGTGT ATCA-
TATGCCAAGTACGCCCCCTATTGACGTCAATGA-
CGGTAAATGGCCCGCCT GGCATTATGCCCAGTA-
CATGACCTTATGGGACTTTCCTACTTGGCAGTA-
CATCTA CGTATTAGTCATCGCTATTACCATGGTGA-
TGCGGTTTTGGCAGTACATCAATGG GCGTGGA-
TAGCGGTTTGACTCACGGGGATTTCCAAGTCTC- CACCCCATTGACGT CAATGGGAGTTTGTTTTGGC-ACCAAAATCAACGGGACTTTCCAAAATGTCGTA-ACAACTCCGCCCCATTGACGCAAATGGGCGGTA-GGCGTGTACGGTGGGAGGTCTA TATAAGCAG-AGCTCTCTGGCTAACTAGAGAACCCACTGCT-TACTGGCTTATCGA AATT-3' (SEQ ID NO: 11). As a specific example, the sequence of the CMV promoter may have a nucleic acid sequence having at least 80%, for example, 80% to 85%, 85% to 90%, 90% to 95%, or 95% to 100%, sequence identity or sequence similarity with a nucleic acid sequence of SEQ ID NO: 11.

For example, the 2A self-cleaving peptide may be T2A, P2A, E2A, F2A, or the like. The 2A self-cleaving peptide may be located between two or more different proteins to be expressed in the vector.

Further, the replication origin may be an f1 replication origin, an SV40 replication origin, a pMB1 replication origin, an adeno replication origin, an AAV replication origin, and/or a BBV replication origin, but is not limited thereto.

The selection element may be a fluorescent protein gene, a tag, a reporter gene, an antibiotic resistance gene, or the like.

For example, the fluorescent protein gene may be a GFP gene, a YFP gene, an RFP gene, an mCherry gene, or the like.

For example, the tag may be a histidine (His) tag, a V5 tag, a FLAG tag, an influenza hemagglutinin (HA) tag, a Myc tag, a VSV-G tag, a thioredoxin (Trx) tag, or the like.

For example, the reporter gene may be glutathione-S-transferase (GST), horseradish peroxidase (HRP), chloramphenicol acetyltransferase (CAT), beta-galactosidase, beta-glucuronidase, or the like.

For example, the antibiotic resistance gene may be a hygromycin resistant gene, a neomycin resistant gene, a kanamycin resistant gene, a blasticidin resistant gene, a zeocin resistant gene, and the like.

Form of Vector

As an exemplary embodiment, the vector may be a viral vector. As a specific example, the viral vector may be one or more selected from the group consisting of a retrovirus, a lentivirus, an adenovirus, an adeno-associated virus (AAV), a vaccinia virus, a poxvirus and a herpes simplex virus. As an exemplary embodiment, the viral vector may be an AAV.

As an exemplary embodiment, the vector may be a non-viral vector. As a specific example, the non-viral vector may be one or more selected from the group consisting of a plasmid, a phage, naked DNA, a DNA complex, and mRNA. As an exemplary embodiment, the plasmid may be selected from the group consisting of the pcDNA series, pS456, p326, pACYC177, ColE1, pKT230, pME290, pBR322, pUC8/9, pUC6, pBD9, pHC79, pIJ61, pLAFR1, pHV14, the pGEX series, the pET series, and pUC19. As an exemplary embodiment, the phage may be selected from the group consisting of λgt4AB, λ-Charon, λΔz1, and M13. As an exemplary embodiment, the encoding nucleic acid may be a PCR amplicon.

Method for Gene Editing Using SpCas9 Variant

Overview of Method for Gene Editing

The present disclosure discloses a method for gene editing using a CRISPR/Cas9 composition. The method for gene editing includes delivering, injecting, and/or introducing (administering) a CRISPR/Cas9 composition to a target subject for gene editing.

Target Subject for Gene Editing 1—Target Individual or Target Tissue

The target subject for gene editing may be an individual or a tissue, and may be referred to as a target individual or a target tissue. As an exemplary embodiment, the target individual may be a plant, animal, non-human animal, and/or human. Specifically, the target individual may be a mammal. As an exemplary embodiment, the target tissue may be a non-human animal tissue and/or a human tissue.

Target Subject for Gene Editing 2—Target Cell

The target subject for gene editing may refer to a cell, and may be referred to as a target cell. As an exemplary embodiment, the target cell may be a prokaryotic cell. As another exemplary embodiment, the target cell may be a eukaryotic cell. Specifically, the eukaryotic cell may be a plant cell, animal cell, non-human animal cell and/or human cell.

Method of Delivering, Injecting, and/or Introducing Composition

The delivery, injection, and/or introduction method is not particularly limited as long as it can deliver the SpCas9 variant or a nucleic acid encoding the same, and the guide RNA or a nucleic acid encoding the same as any one of the configurational forms of the compositions to a cell. Those skilled in the art can perform the method by appropriately selecting a known technique.

As a specific example, the delivery, injection, and/or introduction method may be performed by injection, transfusion, implantation, or transplantation.

As a specific example, the delivery, injection, and/or introduction method may be performed via route selected from subretinal, subcutaneously, intradermally, intraocularly, intravitreally, intratumorally, intranodally, intramedullary, intramuscular, intravenous, intralymphatic, or intraperitoneally.

As a specific example, the delivery, injection, and/or introduction method may be electroporation, a gene gun, sonoporation, magnetofection, and/or temporary cell compression or squeezing.

As an exemplary embodiment, the delivery, injection, and/or introduction method may be delivering a SpCas9 variant or a nucleic acid encoding the SpCas9 variant and/or a guide RNA or a nucleic acid encoding the guide RNA using nanoparticles. In this case, the delivery method may be a cationic liposome method, a lithium acetate-DMSO method, lipid-mediated transfection, a calcium phosphate precipitation method, polyethyleneimine (PEI)-mediated transfection, DEAE-dextran-mediated transfection, and/or nanoparticle-mediated nucleic acid delivery (see Panyam et., al Adv Drug Deliv Rev. 2012 Sep. 13.pii: S0169-409X (12) 00283-9. doi: 10.1016/j.addr.2012.09.023), but is not limited thereto.

As a specific example, the lipid-mediated transfection may be based on lipid nanoparticles (LNPs) and/or PEG. As a specific example, the LNPs may include protonated ionization lipids and/or ionization lipids exhibiting neutrality. As a specific example, the LNPs may further include a phospholipid, cholesterol, or a PEG-linked lipid. In this case, the LNP is a particulate drug delivery vehicle that uses phospholipids, cholesterol, and the like, which are substances present in the body, and therefore has high bioavailability and affinity, enables drug release and control, and is highly stable against degradation by enzymes.

Gene Editing Process

The CRISPR/Cas9 complex derived from the composition introduced into the subject comes into contact with the target nucleic acid, so that the SpCas9 variant recognizes the PAM sequence and the guide domain complementarily binds to a target sequence (a part of the double strand of the target nucleic acid, which complementarily binds to a non-target sequence, which is a part adjacent to the PAM sequence). Moreover, the target nucleic acid is cleaved by the SpCas9 variant of the CRISPR/Cas9 complex.

When the CRISPR/Cas9 complex cleaves the target nucleic acid, any position in the PAM sequence part of the target nucleic acid and/or the sequence part that complementarily binds to the guide domain is cleaved. The CRISPR/Cas9 complex may cause a double-strand break (DSB) part in the target nucleic acid to be repaired through mechanisms such as homology directed repair (HDR) or non-homologous end joining (NHEJ). In this case, when the part is repaired by HDR, the insertion of the donor may occur. In this case, when the part is repaired by NHEJ, this may result in the substitution, insertion or deletion of a short gene fragment, and the knock-out of the corresponding gene may occur.

Gene Editing Result 1—Indel

The method for gene editing may cause an indel to be generated in a target gene or target nucleic acid. In this case, the indel may occur inside and/or outside a target sequence portion. The indel refers to a mutation in the nucleotide sequence of a nucleic acid before gene editing, where some nucleotides are deleted, an arbitrary nucleotide is inserted, and/or a combination of insertion and deletion occurs.

In general, the occurrence of an indel in the target gene or target nucleic acid sequence inactivates the corresponding gene or nucleic acid. In such a case, a protein encoded by the gene may not be expressed or may be expressed as a damaged protein, making it functionally deficient. Such an effect may be referred to as a "gene knock-out."

Gene Editing Result 2—Base Editing

As a result of performing the method for gene editing, base editing may occur in the target gene or target nucleic acid. This means that, unlike an indel, in which any nucleotide in the target gene or target nucleic acid is deleted or added, one or more specific nucleotides in the nucleic acid are changed as intended. In other words, base editing causes a predetermined point mutation at a specific position in the target gene or nucleic acid. As an exemplary embodiment, as a result of performing the method for gene editing, one or more nucleotides in the target gene or target nucleic acid may be substituted with other nucleotides.

Gene Editing Result 3—Insertion

As a result of performing the method for gene editing, knock-in may occur in the target gene or target nucleic acid. The knock-in means inserting an additional nucleic acid sequence into the target gene or target nucleic acid sequence. In addition to the CRISPR/Cas9 complex, a donor including the additional nucleic acid sequence is further required for the knock-in to occur. In this case, the donor may be included in the vector described in the <<Vector for knock-in>> table of contents. When the CRISPR/Cas9 complex cleaves a target gene or target nucleic acid in the cell, repair of the cleaved target gene or target nucleic acid will occur due to homology directed repairing (HDR). In this case, the donor is involved in the repair process, so that the additional nucleic acid sequence may be inserted into the target gene or target nucleic acid. For example, the donor includes an exogeneous DNA sequence for insertion into a cellular genome, and the donor may induce insertion of the exogeneous DNA sequence into the target gene or the target nucleic acid.

Gene Editing Result 4—Large Deletion

As a result of performing the method for gene editing, all or part of the target gene or target nucleic acid sequence may be deleted. The deletion refers to the removal of a partial base sequence (nucleotide sequence) with a certain length or more from the target gene or the target nucleic acid (large deletion). The deletion, compared to the above-described indel effect, may allow the total removal of a specific region of a gene, for example, a first exon region.

Example 1 of Gene Editing-L1111R/D1135V/G1218K/E1219V/A1322R/R1335Q

As an exemplary embodiment, the method for gene editing may include delivering, injecting, and/or introducing a CRISPR/Cas9 composition described in "Component example 1 of composition-L1111R/D1135V/G1218K/E1219V/A1322R/R1335Q" to a target subject for gene editing. As a specific example, after the CRISPR/Cas9 composition is delivered to the target subject for gene editing, the CRISPR/Cas9 complex comes into contact with the target nucleic acid, so that the SpCas9 variant recognizes a PAM sequence which is 5'-NGN-3', and the guide domain complementarily binds to the target sequence (a part of the double strand of the target nucleic acid, which complementarily binds to a non-target sequence, which is a part adjacent to the PAM sequence), allowing the target nucleic acid to be cleaved by the CRISPR/Cas9 complex. As a specific example, when the CRISPR/Cas9 complex cleaves the target nucleic acid, any position in the PAM sequence part which is 5'-NGN-3' of the target nucleic acid and/or the sequence part that complementarily binds to the guide domain may be cleaved. As a specific example, as a result of performing the method for gene editing, indels, base editing, insertions, and/or deletions may occur in the target gene and/or target nucleic acid. As a specific example, as a result of performing the method for gene editing, knock-in and/or knock-out may occur in the target gene and/or target nucleic acid.

Example 2 of Gene Editing-L1111R/D1135V/G1218Q/E1219Q/A1322R/R1333P/T1337L

As an exemplary embodiment, the method for gene editing may include delivering, injecting, and/or introducing a CRISPR/Cas9 composition described in "Component example 2 of composition-L1111R/D1135V/G1218Q/E1219Q/A1322R/R1333P/T1337L" to a target subject for gene editing. As a specific example, after the CRISPR/Cas9 composition is delivered to the target subject for gene editing, the CRISPR/Cas9 complex comes into contact with the target nucleic acid, so that the SpCas9 variant recognizes PAM sequence which is 5'-NNG-3', and the guide domain complementarily binds to the target sequence (a part of the double strand of the target nucleic acid, which complementarily binds to a non-target sequence, which is a part adjacent to the PAM sequence), allowing the target nucleic acid to be cleaved by the CRISPR/Cas9 complex. As a specific example, when the CRISPR/Cas9 complex cleaves the target nucleic acid, any position in the PAM sequence part which is 5'-NNG-3' of the target nucleic acid and/or the sequence part that complementarily binds to the guide domain may be cleaved. As a specific example, as a result of performing the method for gene editing, indels, base editing, insertions, and/or deletions may occur in the target gene and/or target nucleic acid. As a specific example, as a result of performing the method for gene editing, knock-in and/or knock-out may occur in the target gene and/or target nucleic acid.

Example 3 of Gene Editing-L1111R/D1135V/G1218R/E1219F/A1322R/R1333G/R1335H/T1337C As an exemplary embodiment, the method for gene editing may include delivering, injecting, and/or introducing a CRISPR/Cas9 composition described in "Component example 3 of composition-L1111R/D1135V/G1218R/E1219F/A1322R/R1333G/R1335H/T1337C" to a target subject for gene editing. As a specific example, after the CRISPR/Cas9 composition is delivered to the target subject for gene editing, the CRISPR/Cas9 complex comes into contact with the target nucleic acid, so that the SpCas9 variant recognizes PAM sequence which is 5'-NNN-3', and the guide domain complementarily binds to the target sequence (a part of the double strand of the target nucleic acid, which complementarily binds to a non-target sequence, which is a part adjacent to the PAM sequence), allowing the target nucleic acid to be cleaved by the CRISPR/Cas9 complex. As a specific example, when the CRISPR/Cas9 complex cleaves the target nucleic acid, any position in the PAM sequence part which is 5'-NNN-3' of the target nucleic acid and/or the sequence part that complementarily binds to the guide domain may be cleaved. As a specific example, as a result of performing the method for gene editing, indels, base editing, insertions, and/or deletions may occur in the target gene and/or target nucleic acid. As a specific example, as a result of performing the method for gene editing, knock-in and/or knock-out may occur in the target gene and/or target nucleic acid.

Example 4 of Gene Editing-L1111R/D1135V/G1218M/E1219T/A1322R/R1333P/R1335Y/T1337L As an exemplary embodiment, the method for gene editing may include delivering, injecting, and/or introducing a CRISPR/Cas9 composition described in "Component example 4 of composition-L1111R/D1135V/G1218M/E1219T/A1322R/R1333P/R1335Y/T1337L" to a target subject for gene editing. As a specific example, after the CRISPR/Cas9 composition is delivered to the target subject for gene editing, the CRISPR/Cas9 complex comes into contact with the target nucleic acid, so that the SpCas9 variant recognizes PAM sequence which is 5'-NNN-3', and the guide domain complementarily binds to the target sequence (a part of the double strand of the target nucleic acid, which complementarily binds to a non-target sequence, which is a part adjacent to the PAM sequence), allowing the target nucleic acid to be cleaved by the CRISPR/Cas9 complex. As a specific example, when the CRISPR/Cas9 complex cleaves the target nucleic acid, any position in the PAM sequence part which is 5'-NNN-3' of the target nucleic acid and/or the sequence part that complementarily binds to the guide domain may be cleaved. As a specific example, as a result of performing the method for gene editing, indels, base editing, insertions, and/or deletions may occur in the target gene and/or target nucleic acid. As a specific example, as a result of performing the method for gene editing, knock-in and/or knock-out may occur in the target gene and/or target nucleic acid.

Method for Screening SpCas9 Variant

Overview of Screening Method

The present disclosure discloses a method for screening a SpCas9 variant. In this case, the SpCas9 variant is characterized by the ability to recognize a PAM sequence other than 5'-NGG-3'. As a specific example, the method may include 1) a Cas9 cell library production step and/or 2) a mutant protein selection step. In this case, the mutant protein selection step may include a primary selection step and/or a secondary selection step.

Cas9 Cell Library Production Stage

As a specific example, the Cas9 cell library production step may include a PiggyBac using step and/or a transposase using step.

The PiggyBac using step is a step of producing a library by substituting n (specifically, n may be 1, 2, 3, 4, 5, 6, 7, 8, 9, 10, 11, 12, 13, 14, 15, 16, 17, 18, 19, or 20) amino acid residues with another amino acid (any one of about 20 types) to clone a nucleic acid encoding an SpCas9 protein having $20^n$ diversity in a PiggyBac-based vector.

The transposase using step is a step of producing a cell library having $20^n$ diversity by transfecting cells with the library produced in the PiggyBac using step together with a transposase vector to induce integration into the genomic DNA of each cell.

As a specific example, the SpCas9 protein having $20^n$ diversity may include the L1111R/D1135V/A1322R mutation compared to the wild-type SpCas9 protein.

As a specific example, the residue in which the amino acid is substituted may include at least one of the G1218 and E1219 amino acid residues of the wild-type SpCas9 protein. As a specific example, the residue in which the amino acid is substituted may include at least one of the R1333, R1335, and T1337 amino acid residues of the wild-type SpCas9 protein.

Primary Selection Step

The primary selection step involves transfecting the produced cell library with various types of sgRNAs targeting the HPRT gene, and then treating the cells with 6-thioguanine (6TG) to allow only cells with mutations in the HPRT gene to survive. In this case, the surviving cells are those in which the SpCas9 protein reacts with sgRNA to generate an indel in the HPRT gene, and the SpCas9 transfected into the surviving cells recognizes a PAM sequence other than 5'-NGG-3'.

As a specific example, the sgRNA targets a target sequence adjacent to a PAM sequence other than 5'-NGG-3'. As a specific example, the PAM sequence other than 5'-NGG-3' may include at least one sequence of 5'-CC-3', 5'-TT-3', 5'-AA-3', 5'-GC-3', 5'-GT-3', and 5'-GA-3'.

Secondary Selection Step

The secondary selection step involves transfecting a pool of cells of the same type as the surviving cells (cells which are the same as transfected SpCas9 protein, but without mutations in the HPRT gene) in the primary selection step with various types of sgRNAs targeting the HPRT gene, and then treating the cells with 6-thioguanine (6TG) to allow only cells with mutations in the HPRT gene to survive. In this case, the surviving cells are those in which the SpCas9 protein reacts with sgRNA to generate an indel in the HPRT gene, and the SpCas9 transfected into the surviving cells recognizes a PAM sequence other than 5'-NGG-3'.

As a specific example, the sgRNA targets a target sequence adjacent to a PAM sequence other than 5'-NGG-3'. As a specific example, the PAM sequence other than 5'-NGG-3' may include at least one sequence of 5'-CC-3', 5'-TT-3', 5'-AA-3', 5'-GC-3', 5'-GT-3', and 5'-GA-3'. As a specific example, when the sgRNA used in the secondary selection step is compared to the sgRNA used in the primary selection step, the PAM sequences adjacent to the sequences targeted by the sgRNAs may be the same, but the sequences targeted by the sgRNAs are different sequences.

POSSIBLE EXAMPLES OF INVENTION

Hereinafter, possible examples of the disclosure are listed. The following examples provided in this paragraph merely correspond to examples of the disclosure. Therefore, the disclosure should not be construed as being limited to the following examples. The brief description described with the example numbers is also for the convenience of dividing the examples, and cannot be construed as a limitation on the disclosure.

Four SpCas9 Variants

Example 1. SpCas9 Variant

A *Streptococcus pyogenes* Cas9 (SpCas9) variant, represented by an amino acid sequence with six or more amino acid residue differences compared to SEQ ID NO:1 which is an amino acid sequence of wild-type SpCas9 protein.

Example 2. Variant 1

The SpCas9 variant of Example 1, wherein the SpCas9 variant includes L1111R/D1135V/A1322R mutation compared to the wild-type SpCas9 protein.

Example 3. G1218 and E1219

The SpCas9 variant of Examples 1 and 2, wherein the SpCas9 variant includes a mutation in which any one or more of the G1218 and E1219 amino acid residues of the wild-type SpCas9 protein are substituted with other amino acids.

Example 4. R1333, R1335, and T1337

The SpCas9 variant of Examples 1 to 3, wherein the SpCas9 variant includes a mutation in which any one or more of the R1333, R1335, and T1337 amino acid residues of the wild-type SpCas9 protein are substituted with other amino acids.

Example 5. G1218K/E1219V/R1335Q

The SpCas9 variant of Examples 1 to 4, wherein the SpCas9 variant includes L1111R/D1135V/G1218K/E1219V/A1322R/R1335Q mutation.

Example 6. SEQ ID NO: 3

The SpCas9 variant of Example 5, wherein the SpCas9 variant includes a sequence having at least 80% identity to an amino acid sequence of SEQ ID NO: 3 or a sequence having 100% identity to the amino acid sequence of SEQ ID NO: 3.

Example 7. NGN PAM

The SpCas9 variant of Examples 5 and 6, wherein the SpCas9 variant is capable of recognizing PAM sequence which is 5'-NGN-3'.

Example 8. G1218Q/E1219Q/R1333P/T1337L

The SpCas9 variant of Examples 1 to 4, wherein the SpCas9 variant includes L1111R/D1135V/G1218Q/E1219Q/A1322R/R1333P/T1337L mutation.

Example 9. SEQ ID NO: 4

The SpCas9 variant of Example 8, wherein the SpCas9 variant includes a sequence having at least 80% identical to an amino acid sequence of SEQ ID NO: 4 or a sequence having 100% identical with the amino acid sequence of SEQ ID NO: 4.

Example 10. NNG PAM

The SpCas9 variant of Examples 8 and 9, wherein the SpCas9 variant is capable of recognizing PAM sequence which is 5'-NNG-3'.

Example 11. G1218R/E1219F/R1333G/R1335H/T1337C

The SpCas9 variant of Examples 1 to 4, wherein the SpCas9 variant includes L1111R/D1135V/G1218R/E1219F/A1322R/R1333G/R1335H/T1337C mutation.

Example 12. SEQ ID NO: 5

The SpCas9 variant of Example 11, wherein the SpCas9 variant includes a sequence having at least 80% identical to an amino acid sequence of SEQ ID NO: 5 or a sequence having 100% identical with the amino acid sequence of SEQ ID NO: 5.

Example 13. PAMless

The SpCas9 variant of Examples 11 and 12, wherein the SpCas9 variant is PAMless.

Example 14. G1218M/E1219T/R1333P/R1335Y/T1337L

The SpCas9 variant of Examples 1 to 4, wherein the SpCas9 variant includes L1111R/D1135V/G1218M/E1219T/A1322R/R1333P/R1335Y/T1337L mutation.

Example 15. SEQ ID NO: 6

The SpCas9 variant of Example 14, wherein the SpCas9 variant includes a sequence having at least 80% identical to an amino acid sequence of SEQ ID NO: 6 or a sequence having 100% identical with the amino acid sequence of SEQ ID NO: 6.

Example 16. PAMless

The SpCas9 variant of Examples 14 and 15, wherein the SpCas9 variant is PAMless.

Example 17. Capable of Binding to Guide RNA

The SpCas9 variant of Examples 1 to 16, wherein the SpCas9 variant is capable of forming a CRISPR/Cas9 complex by interacting with the guide RNA.

Example 18, Guide RNA Configuration

The SpCas9 variant of Example 17,
- wherein the guide RNA includes a crRNA and a tracrRNA,
- wherein the crRNA includes a guide domain and a direct repeat,
- wherein the direct repeat and the tracrRNA are capable of forming a CRISPR/Cas9 complex by interacting with the SpCas9 variant.

Example 19, Direct Repeat Sequence

The SpCas9 variant of Example 18, wherein the direct repeat includes a nucleic acid sequence having at least 80%, for example, 80% to 85%, 85% to 90%, 90% to 95%, or 95% to 100%, sequence identity or sequence similarity with a sequence of SEQ ID NO: 7.

Example 20, TracrRNA Sequence

The SpCas9 variant of Examples 18 and 19, wherein the tracrRNA includes a nucleic acid sequence having at least 80%, for example, 80% to 85%, 85% to 90%, 90% to 95%, or 95% to 100%, sequence identity or sequence similarity with a sequence of SEQ ID NO: 8.

Composition Including the SpCas9 Variant

Example 21, Composition

A CRISPR/Cas9 composition including the SpCas9 variant of any one of Examples 1 to 20 or a nucleic acid encoding the SpCa9 variant.

Example 22, Including Guide RNA

The CRISPR/Cas9 composition of Example 21, wherein the CRISPR/Cas9 composition further includes a guide RNA or a nucleic acid encoding the guide RNA.

Example 23, Guide RNA Configuration

The SpCas9 variant of Example 22,
- wherein the guide RNA includes a crRNA and a tracrRNA,
- wherein the crRNA includes a guide domain and a direct repeat,
- wherein the direct repeat and the tracrRNA are capable of forming a CRISPR/Cas9 complex by interacting with the SpCas9 variant,
- wherein the target gene includes a target strand and a non-target strand,
- wherein the target strand includes a target sequence,
- wherein the non-target strand includes a non-target sequence,
- wherein the target sequence and the non-target sequence are capable of complementarily binding to each other,
- wherein the guide domain is capable of binding to the target sequence of the target strand.

Example 24, Direct Repeat Sequence

The CRISPR/Cas9 composition of Example 23, wherein the direct repeat includes a nucleic acid sequence having at least 80%, for example, 80% to 85%, 85% to 90%, 90% to 95%, or 95% to 100%, sequence identity or sequence similarity with a sequence of SEQ ID NO: 7.

Example 25, TracrRNA Sequence

The CRISPR/Cas9 composition of Example 19, wherein the tracrRNA includes a nucleic acid sequence having at least 80%, for example, 80% to 85%, 85% to 90%, 90% to 95%, or 95% to 100%, sequence identity or sequence similarity with a sequence of SEQ ID NO: 8.

Example 26, CRISPR/Cas9 Complex

The CRISPR/Cas9 composition of any one of Examples 22 to 25, wherein the SpCas9 variant and the guide RNA are capable of forming a CRISPR/Cas9 composition by interacting with each other.

Example 27, RNP

The CRISPR/Cas9 composition of any one of Examples 21 to 26, wherein the SpCas9 variant and the guide RNA are in the form of ribonucleoprotein (RNP).

Example 28, Vector

The CRISPR/Cas9 composition of any one of Examples 21 to 26,
- wherein the CRISPR/Cas9 composition includes a vector,
- wherein a nucleic acid encoding the SpCas9 variant and/or a nucleic acid encoding the guide RNA are included in the vector.

Example 29, Including Donor

The CRISPR/Cas9 composition of any one of Examples 21 to 28, wherein the CRISPR/Cas9 composition includes a donor.

Example 30, Limited to Donor

The CRISPR/Cas9 composition of Example 29, wherein the donor includes a gene for insertion into the target sequence.

Example 31, Vector Form of Donor

The CRISPR/Cas9 composition of Example 30, wherein the donor is in the form of a vector.

Example 32, Other Configurations of Vector

The CRISPR/Cas9 composition of any one of Examples 28 to 31, wherein the vector includes one or more of a promoter, an enhancer, an artificial intron, a polyadenylation signal, a Kozak consensus sequence, an internal ribosome entry site (IRES), a splice acceptor, a 2A sequence, and a replication origin.

Example 33, Promoter

The CRISPR/Cas9 composition of Example 32, wherein the promoter is one of an SV40 initial promoter, a mouse mammary tumor virus long terminal repeat (LTR) promoter, an adenovirus major late promoter (Ad MLP), a herpes simplex virus (HSV) promoter, a cytomegalovirus (CMV) promoter such as a CMV immediate early promoter region (CMVIE), a Rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31 (17)), a human H1 promoter (H1), and 7SK.

Example 34, Form of Vector

The CRISPR/Cas9 composition of any one of Examples 28 to 33, wherein the vector is a viral vector.

Example 35, Type of Viral Vector

The CRISPR/Cas9 composition of Example 34, wherein the viral vector is one selected from the group consisting of a retrovirus, a lentivirus, an adenovirus, an adeno-associated virus (AAV), a vaccinia virus, a poxvirus, and a herpes simplex virus.

Example 36, Form of Vector

The CRISPR/Cas9 composition of any one of Examples 28 to 33, wherein the vector is a non-viral vector.

Example 37, Type of Non-Viral Vector

In Example 36, the non-viral vector may be one or more selected from the group consisting of a plasmid, a phage, naked DNA, a DNA complex, and mRNA. As an exemplary embodiment, the CRISPR/Cas9 wherein the plasmid is one selected from the group consisting of the pcDNA series, pS456, p326, pACYC177, ColE1, pKT230, pME290, pBR322, pUC8/9, pUC6, pBD9, pHC79, plJ61, pLAFR1, pHV14, the pGEX series, the pET series, and pUC19.

Method for Gene Editing Using Composition

Example 38, Injection of Composition

A method for gene editing, wherein the method includes delivering, injecting, and/or introducing (administering) the CRISPR/Cas9 composition of any one of Examples 21 to 37 to a target subject for gene editing.

Example 39, Target Subject for Gene Editing-Target Individual, Tissue, and Cell

The method of Example 38, wherein the target subject for gene editing is a target individual, a target tissue, or a target cell.

Example 40, Target Individual

The method of Example 39, wherein the target individual is a plant, animal, non-human animal, or human.

Example 41, Target Tissue

The method of Example 39, wherein the target tissue is a non-human animal tissue or human tissue.

Example 42, Target Cell

The method of Example 39, wherein the target cell is a eukaryotic cell or prokaryotic cell.

Example 43, Delivery, Injection, and/or Introduction (Administration) Method

The method of any one of Examples 38 to 42, wherein the delivery, injection, and/or introduction is performed by one or more of injection, transfusion, implantation, transplantation, electroporation, gene gun, sonoporation, magnetofection, temporary cell squeezing, a cationic liposome method, lithium acetate-DMSO, lipid-mediated transfection, a calcium phosphate precipitation method, lipofection, polyethyleneimine (PEI)-mediated transfection, DEAE-dextran-mediated transfection, and nanoparticle-mediated nucleic acid delivery (see Panyam et., al Adv Drug Deliv Rev. 2012 Sep. 13.pii: S0169-409X (12) 00283-9. doi: 10.1016/j.addr.2012.09.023).

Example 44, Gene Editing Process

The method of any one of Examples 38 to 44, wherein, by delivering, injecting, and/or introducing (administering) the CRISPR/Cas9 composition to the target subject for gene editing, the CRISPR/Cas9 complex is capable of cleaving a portion of the target nucleic acid adjacent to PAM sequence other than 5'-NGG-3'.

Example 45, Gene Editing Results

The method of any one of Examples 38 to 44, wherein, by delivering, injecting, and/or introducing (administering) the CRISPR/Cas9 composition to the target subject for gene editing, indel, base editing, insertion, and/or deletion may occur at a target nucleic acid portion adjacent to PAM sequence other than 5'-NGG-3'.

Example 46, NGN PAM

The method of any one of Examples 44 and 45, wherein the SpCas9 variant includes G1218K/E1219V/R1335Q mutation, wherein the PAM sequence is 5'-NGN-3'.

Example 47, NNG PAM

The method of any one of Examples 44 and 45, wherein the SpCas9 variant includes G1218Q/E1219Q/R1333P/T1337L mutation, wherein the PAM sequence is 5'-NNG-3'.

Example 48, NNN PAM

The method of any one of Examples 44 and 45, wherein the SpCas9 variant includes G1218R/E1219F/R1333G/R1335H/T1337C mutation, wherein the PAM sequence is 5'-NNN-3'.

Example 49, NNN PAM

The method of any one of Examples 44 and 45, wherein the SpCas9 variant includes G1218M/E1219T/R1333P/R1335Y/T1337L mutation, wherein the PAM sequence is 5'-NNN-3'.

Method for Screening SpCas9 Variant

Example 50, Screening Method

A method for screening a SpCas9 variant, which is capable of recognizing a PAM sequence other than 5'-NGG-3'.

Example 51, Cas9 Cell Library Production Step

The method of Example 50, wherein the screening method includes a Cas9 cell library production step.

Example 52, PiggyBac Using Step

The method of Example 51, wherein the Cas9 cell library production step includes a PiggyBac using step, wherein the PiggyBac using step is a step of producing a library by cloning a nucleic acid encoding a SpCas9 protein in which 1 to 20 amino acid residues of the wild-type SpCas9 protein are substituted with other amino acids into a PiggyBac-based vector.

Example 53, Transposase Using Step

The method of any one of Examples 51 and 52, wherein the Cas9 cell library production step includes a transposase using step, wherein the transposase using step is a step of producing a cell library by transfecting a library, produced by cloning a nucleic acid encoding a SpCas9 protein in which 1 to 20 amino acid residues of the wild-type SpCas9 protein are substituted with other amino acids into a PiggyBac-based vector, together with a transposase vector to induce integration into the genomic DNA of each cell.

Example 54, Mutant Protein Selection Step

The method of any one of Examples 50 to 53, wherein the method includes a mutant protein selection step.

Example 55, Primary Selection Step

The method of Example 54, wherein the mutant protein selection step includes a primary selection step, wherein the primary selection step is a step of transfecting a cell library, produced by transfecting a library produced by cloning a nucleic acid encoding a SpCas9 protein in which 1 to 20 amino acid residues of the wild-type SpCas9 protein are substituted with other amino acids into a PiggyBac-based vector together with a transposase vector to induce integration into the genomic DNA of each cell, with sgRNA targeting an HPRT gene, and then treating the cells with 6-thioguanine (6TG).

Example 56, Secondary Selection Step

The method of Example 55, wherein the mutant protein selection step includes a secondary selection step, wherein the secondary selection step is a step of transfecting a pool of cells of the same type as the surviving cells (cells which are the same as transfected SpCas9 protein, but without mutations in the HPRT gene) in the primary selection step with sgRNA targeting the HPRT gene, and then treating the cells with 6-thioguanine (6TG).

EXPERIMENTAL EXAMPLES

Hereinafter, the disclosure may be described in more detail through Experimental Examples and Examples. These Examples are only for exemplifying the content disclosed by the present disclosure, and it will be obvious to those skilled in the art that the scope of the content disclosed by the present disclosure should not be interpreted as being limited by these Experimental Examples and Examples.

Experiment Overview

The configuration of the present disclosure was carried out using the following screening method.

In the sequence of the wild-type SpCas9 protein (SEQ ID NO: 1), a library was produced by substituting five representative amino acid residues (G1218, E1219, R1333, R1335, and T1337) which are known to interact with the PAM sequence with 20 other amino acids to clone a nucleic acid encoding a Cas9 variant with a total of 205 diversity into a PiggyBac-based vector. In this case, the Cas9 variant includes L1111R/D1135V/A1322R mutation compared to the wild-type SpCas9 protein.

A library with 205 diversity was produced by transfecting cells with the produced library together with a transposase vector to induce integration into the genomic DNA of each cell (FIG. 1, library development method).

The produced library was transfected with sgRNA targeting the HPRT gene. The transfected sgRNAs include sgRNA targeting a target sequence that complementarily binds to a non-target sequence adjacent to different PAM sequences. Thereafter, cells were treated with 6-thioguanine (6TG) to allow only cells with a mutation in the HPRT gene to survive. The surviving cells are in a state in which a nucleic acid encoding a Cas9 variant that successfully cleaves the target sequence adjacent to the PAM sequence associated with the transfected sgRNA is integrated into the corresponding cells (FIG. 1, screening method).

After five positions with amino acid mutations in the Cas9 variant associated with the nucleic acid integrated into the above surviving cells were amplified using PCR amplification, these positions were analyzed using NGS to obtain clones. The PAM sequence of the obtained Hit was later validated by additional experiments (FIG. 1, analysis method).

Specific Experimental Method Used in Experiment

Cas9 Variants Plasmid Library Production

PCR was performed using an oligo library pool (a product of Combinatorial Variant Library manufactured by Twist Bioscience was ordered) as a template for nucleic acids encoding SpCas9 variants in which five amino acid residues were site saturation mutated (SSM).

A pblc-based plasmid library in which a product obtained by the above PCR (a product obtained using the oligo library pool as a template) was inserted into a PBLC vector (purchased from Bioneer) by a cloning method using a Gibson assembly (performed at 50° C. overnight) was produced. In the corresponding experiment, primers of SEQ ID NOs: 25 to 27 were used.

PCR was performed using the produced pblc-based plasmid library as a template. A PiggyBac-based Cas9 variants plasmid library in which a product obtained by PCR (a product obtained using the pblc-based plasmid library as a template) was inserted into a PiggyBac vector (purchased from SBI) by a cloning method using a Gibson assembly (performed at 50° C. overnight) was produced.

Cas9 Variants Cell Library Production

HeLa cells were seeded onto 5 dishes (150 mm) at $2\times10^6$ cells/dish. 24 hours after cell seeding, Hela cells were co-transfected with the PiggyBac-based Cas9 variants plasmid library and a transposase expressed vector using Lipofectamine 2000 (PiggyBac-based Cas9 variants plasmid library: transposase=2 μg: 2 μg) for integration.

The PiggyBac-based Cas9 variants plasmid library includes a puromycin resistance gene. 24 hours after cotransfection, puromycin selection was performed using a medium containing 2 μg/ml puromycin. 96 hours after puromycin selection, subculture was carried out. One week after subculture, cells stock was performed to produce a primary Cas9 variants cell library.

qRT-PCR for Copy Number Confirmation

A PiggyBac copy number kit (purchased from SBI) was used. After genomic DNA was extracted from the produced piggyBac-based cas9 variants cell library (prep), qRT-PCR was performed using a primer provided in the kit. The obtained Ct value was substituted into a formula (ΔΔCt-2-(Pbcopy-UCR1), copy number=ΔΔCt/2) to calculate an integration copy number.

Primary Screening

A primary Cas9 variants cell library was seeded at $2\times10^6$ cells onto a 150 mm dish. 20 μg of pRG vectors (HPRT target: CC, TT, AA, GC, GT, GA pam sgRNA) capable of expressing sgRNA for primary screening, which targets (is bound by the guide domain of sgRNA) a sequence adjacent to the PAM sequence (5'-NCC-3', 5'-NTT-3', 5'-NAA-3', 5'-NGC-3', 5'-NGT-3', 5'-NGA-3') other than 5'-NGG-3' in the HPRT gene were transfected using Lipofectamine 2000. 3 days after transfection, subculture was performed. 7 days after transfection, 6-thioguanine (6TG) selection was started using a medium including 3 μM 6TG simultaneously with subculture. 14 days after the start of 6TG selection, subculture was performed. 17 days after the start of 6TG selection, cells were harvested, and genomic DNA was extracted (prep).

Secondary Screening

The cell pool obtained through 6TG selection in the primary screening was seeded at $2\times10^6$ cells onto a 150 mm dish. 20 μg of pRG vectors (HPRT target: CC, TT, AA, GC, GT, GA pam sgRNA) capable of expressing sgRNA for secondary screening, which targets (is bound by the guide domain of sgRNA) a sequence adjacent to the PAM sequence (5'-NCC-3', 5'-NTT-3', 5'-NAA-3', 5'-NGC-3', 5'-NGT-3', 5'-NGA-3') other than 5'-NGG-3' in the HPRT gene were transfected using Lipofectamine 2000. 3 days after transfection, subculture was performed. 7 days after transfection, 6-TG selection was started using a medium including 3 μM 6-thioguanine simultaneously with subculture. 14 days after the start of 6-TG selection, subculture was performed. 17 days after the start of 6-TG selection, cells were harvested, and genomic DNA was extracted (prep).

ddPCR for Hit Identification 50 ng of genomic DNA was used (conditions for inserting one genomic copy per drop), and ddPCR EvaGreen Supermix (Bio-Rad) was used for amplification. ddPCR Supermix amplification reactions were set up according to the manufacturer's protocol (Bio-Rad). Droplets were generated using DG8 cartridges, DG8 Gaskets, and a QX200™ Droplet generator (Bio-Rad). The generated droplets were transferred to a 96-well plate and heat-sealed using a PX1 PCR plate sealer (Bio-Rad). The PCR conditions were used by changing only the annealing temperature to 61° C. in the manufacturer's protocol for QX200 ddPCR EvaGreen Supermix. Droplets were individually scanned using a QX200™ Droplet Digital™ PCR system (BioRad). After PCR, 20 ul of water was added to break the droplets, the droplets were vortexed, the droplets were then frozen in liquid nitrogen and thawed at room temperature three times, and then the droplets were spun down to separate an aqueous layer and an oil layer. Purification was performed by collecting only the aqueous layer.

Circularization for NGS

Circularization for NGS was performed in the following order:

1. T4 PNK treatment (37° C. for 1 hour) followed by purification;
2. T4 DNA ligase treatment (16° C. for 16 hours) followed by purification;
3. Plasmid-safe ATP-dependent DNase treatment (37° C. for 1 hour, 70° C. for 30 minutes) followed by purification;
4. Pvull restriction enzyme treatment (37° C. for 2 hours) followed by purification; and
5. NGS adaptor+index PCR.

Primers of SEQ ID NOS: 28 to 41 were used to carry out the PCR.

Transfection of Selected Cas9 Variants into PAM Analysis Cell Libraries for PAM Analysis A cell library was seeded at $2\times10^6$ cells/dish onto 5 dishes (150 mm). For this purpose, 24 hours after cell seeding, 20 μg of lenti-based vector candidates were transfected using Lipofectamine 2000. In this case, lenti-based vector candidates are lenti-based vectors that are capable of expressing sgRNA which targets (is bound by the guide domain of sgRNA) a sequence adjacent to the PAM sequence (5'-NNN-3', where each N is any one of A, C, T, and G, and there are 256 different types of PAM sequences, for a total of 44 types) in the HPRT gene. In this case, primers of SEQ ID NOs: 42 to 50 were used to produce a cell library for verification.

24 hours after transfection, blasticidin selection was started using a medium including 20 μg/ml blasticidin. 120 hours after transfection, cells were harvested and genomic DNA was extracted (prep) ($1\times10^8$ cells genomic extraction).

Deep Sequencing

For the primary PCR, a template was used with a coverage of ×1000 for the library scale (assuming 10 μg of genomic DNA per $10^6$ cells). The primary PCR was carried out at 2.5 μg/reaction×48 reactions. In the experiments of the present specification, primers of SEQ ID NOS: 51 to 56 were used. All the primary PCR pools were collected and purified, and then barcoded PCR was performed. Finally, Illumina Hlseq was performed.

Experimental Example 1. Development of SpCas9 Protein Library

Experimental Example 1-1. Determining Mutation Site of SpCas9 Protein

The present inventors predicted that when amino acid residues affecting the recognition of PAM sequence by the Cas9 protein were modified, it would be possible to select a SpCas9 variant capable of recognizing PAM sequence other than 5'-NGG-3'.

Figure 2:
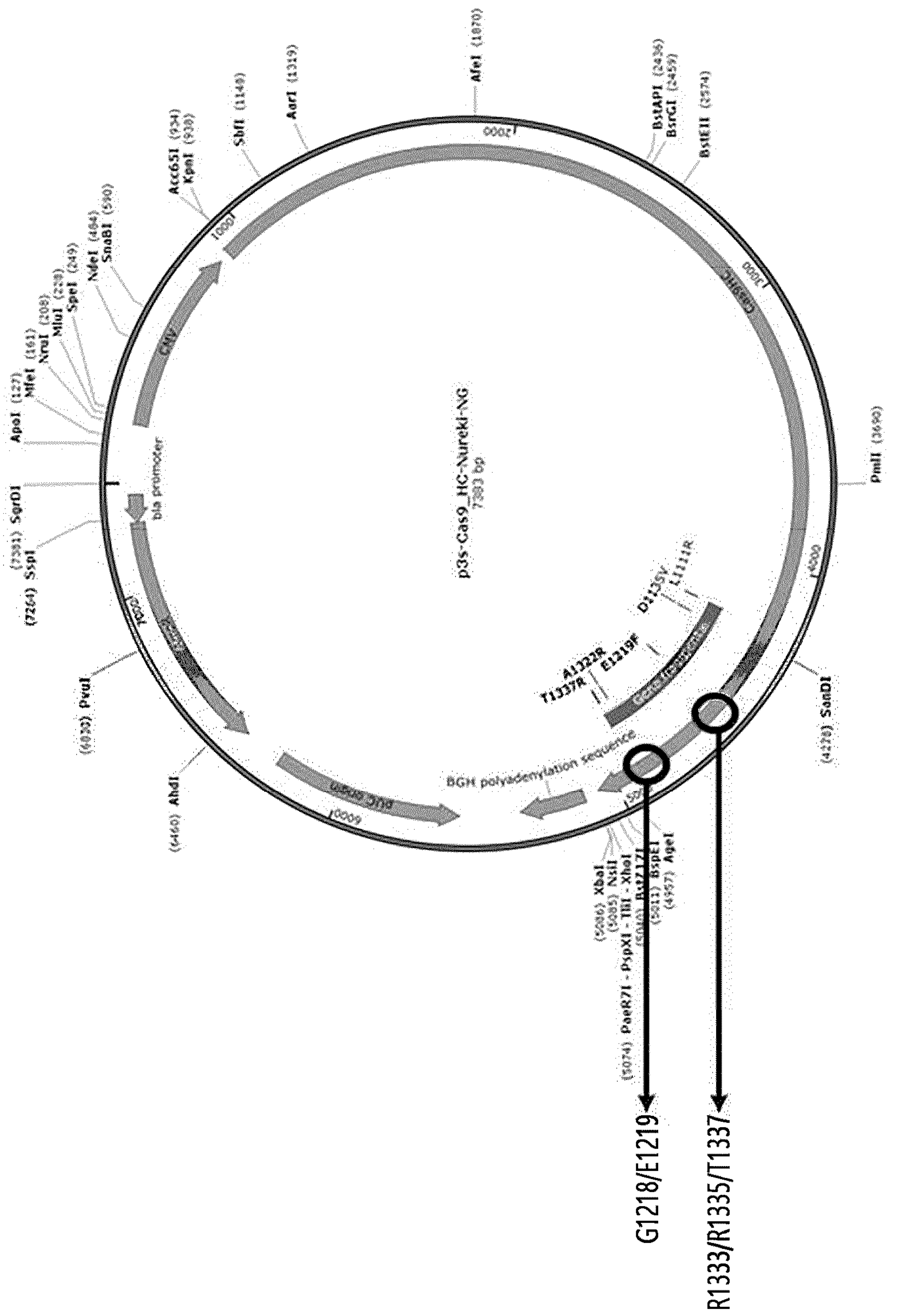
FIG. 2 is a schematic view of a Nureki-NG Cas9 expression vector, showing the mutated parts (G1218/E1219, R1333/R1335/T1337) of the SpCas9 variant of the present disclosure.

Therefore, in Nureki-NG Cas9 (Nureki-NG Cas9 is a Cas9 having L1111R/D1135V/G1218R/E1219F/A1322R/R1335V/T1337R mutation from the wild-type SpCas9 protein.), directed evolution was performed using site saturation mutations on a total of five amino acid residues: G1218 and E1219, which form hydrophobic interactions with a portion of the ribose in the PAM sequence, and R1333, R1335, and T1337, which directly recognize and bind to the PAM sequence (FIG. 2). In this case, directed evolution was performed using the above site saturation mutation while including the L1111R/D1135V/A1322R mutation among the mutations that the Nureki-NG Cas9 has.

Experimental Example 1-2. Production of SpCas9 Variant Library

Figure 3:
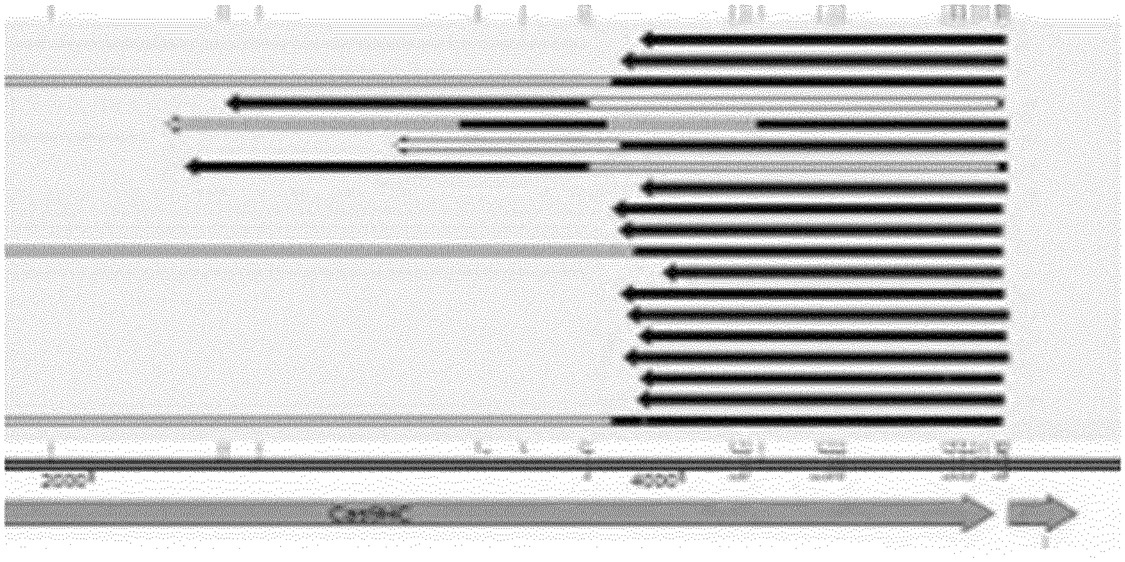
FIG. 3 relates to a pBLC vector used to produce a Cas library.
Figure 4:
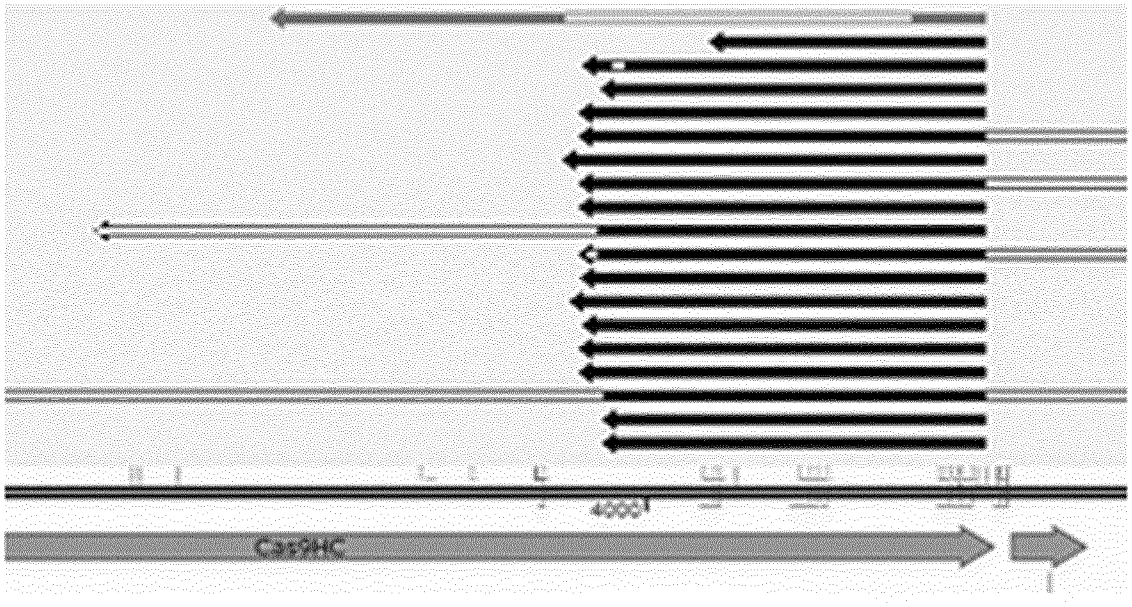
FIG. 4 relates to a piggyBac vector used to produce a Cas library.

A Cas9 variants plasmid library with a scale of over $10^6$ was produced by the Gibson assembly method using an oligo pool including a nucleic acid encoding a Cas9 variant with site saturation mutation applied to five amino acid residues. First, to improve transfection efficiency, a Cas9 variants plasmid library was produced in a small pBLC vector (2.8 kb) (quality-84%) (FIG. 3). Second, the Cas9 variants plasmid library was transferred to a piggyBac vector that can be integrated to produce a cell library (quality=89%) (FIG. 4).

Experimental Example 2. Selection of SpCas9 Variant with Novel PAM

A Cas9 variants cell library was produced using the PiggyBac-based Cas9 variants plasmid library produced above. In this case, a cell library consisting of cells, into which nucleic acids encoding Cas9 variants were integrated, was produced through puromycin selection.

After the produced cell library was transfected with a guide RNA, 6-TG selection was performed to allow only cells in which the Cas9 variant reacted with the guide RNA to edit the HPRT gene to survive. By analyzing the sequence of the Cas9 variant corresponding to the surviving cells, a candidate group of SpCas9 variants recognizing novel PAM was selected.

Experimental Example 2-1. Production of Cell Library of SpCas9 Variants Through Puromycin Selection Hela cells highly sensitive to 6-TG selection were used in the screening process. Hela cells were co-transfected with the piggyBac-based cas9 variants plasmid library produced in Experimental Example 2 and a transposase expression vector for integration. Thereafter, a cas9 variants cell library was produced by allowing only integrated cells to survive through puromycin selection because the piggyBac-based cas9 variants plasmid library includes a puromycin resistance gene. The integration copy number of the produced piggyBac-based cas9 variants cell library was measured using qRT-PCR (integration copy number=5.6).

Experimental Example 2-2. Selection of SpCas9 Variants by 6-TG Selection

Figure 5:
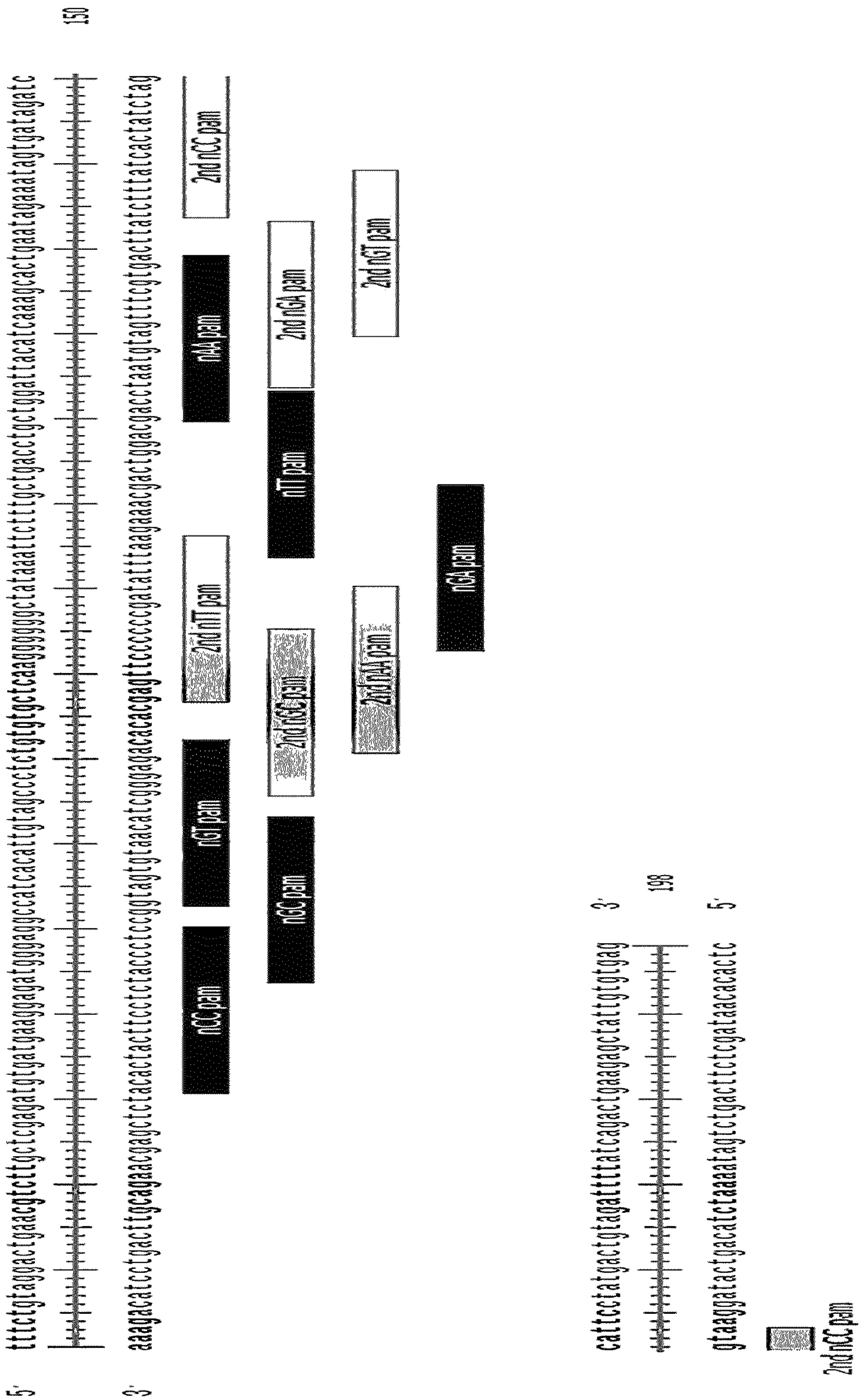
FIG. 5 relates to guide RNA used in the primary and secondary screening, showing the sequences of guide RNAs for different PAM sequences.
Figure 6:
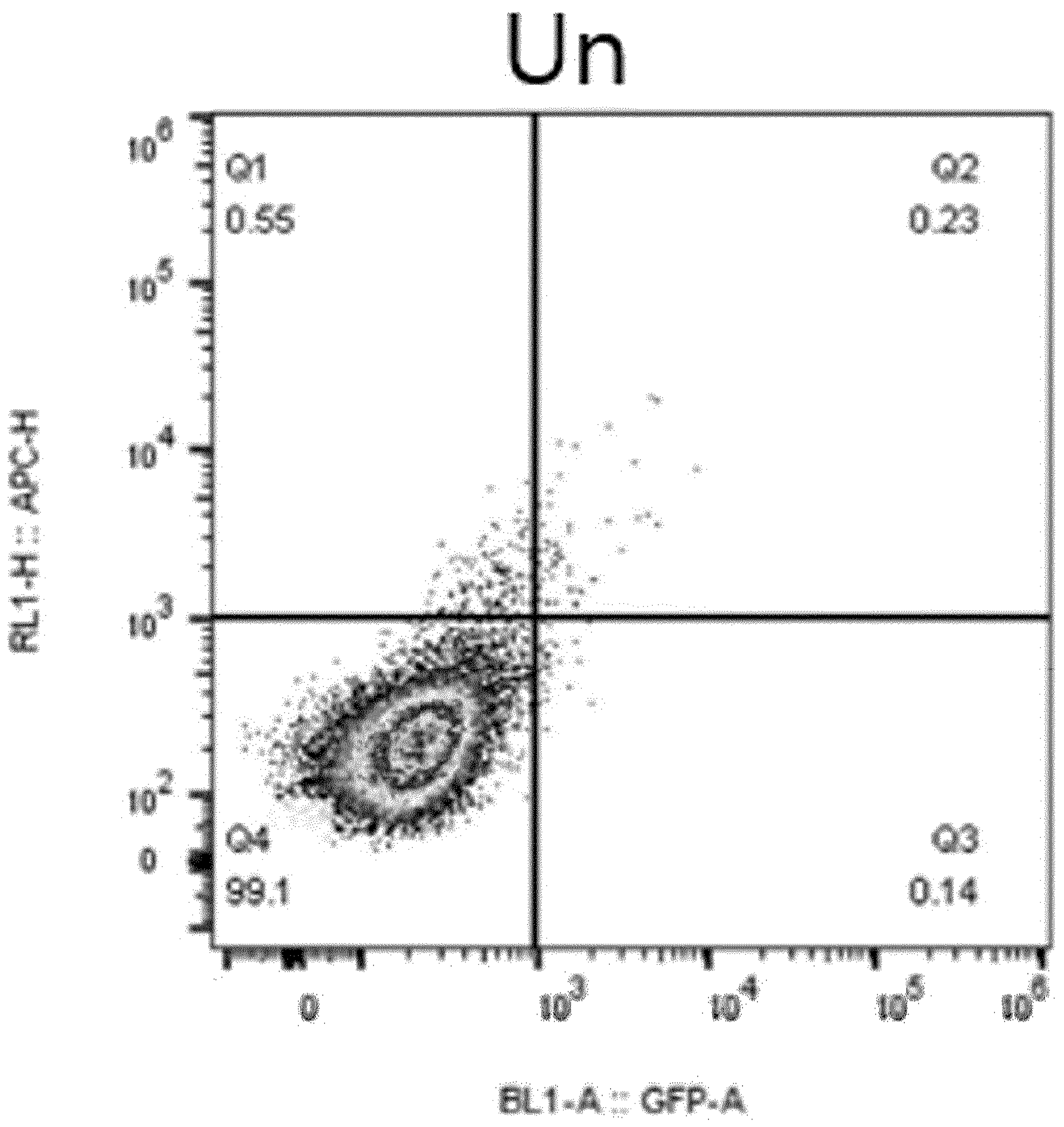
FIGS. 6 to 9 show the results analyzed by flow cytometry using a GFP expression vector.
Figure 7:
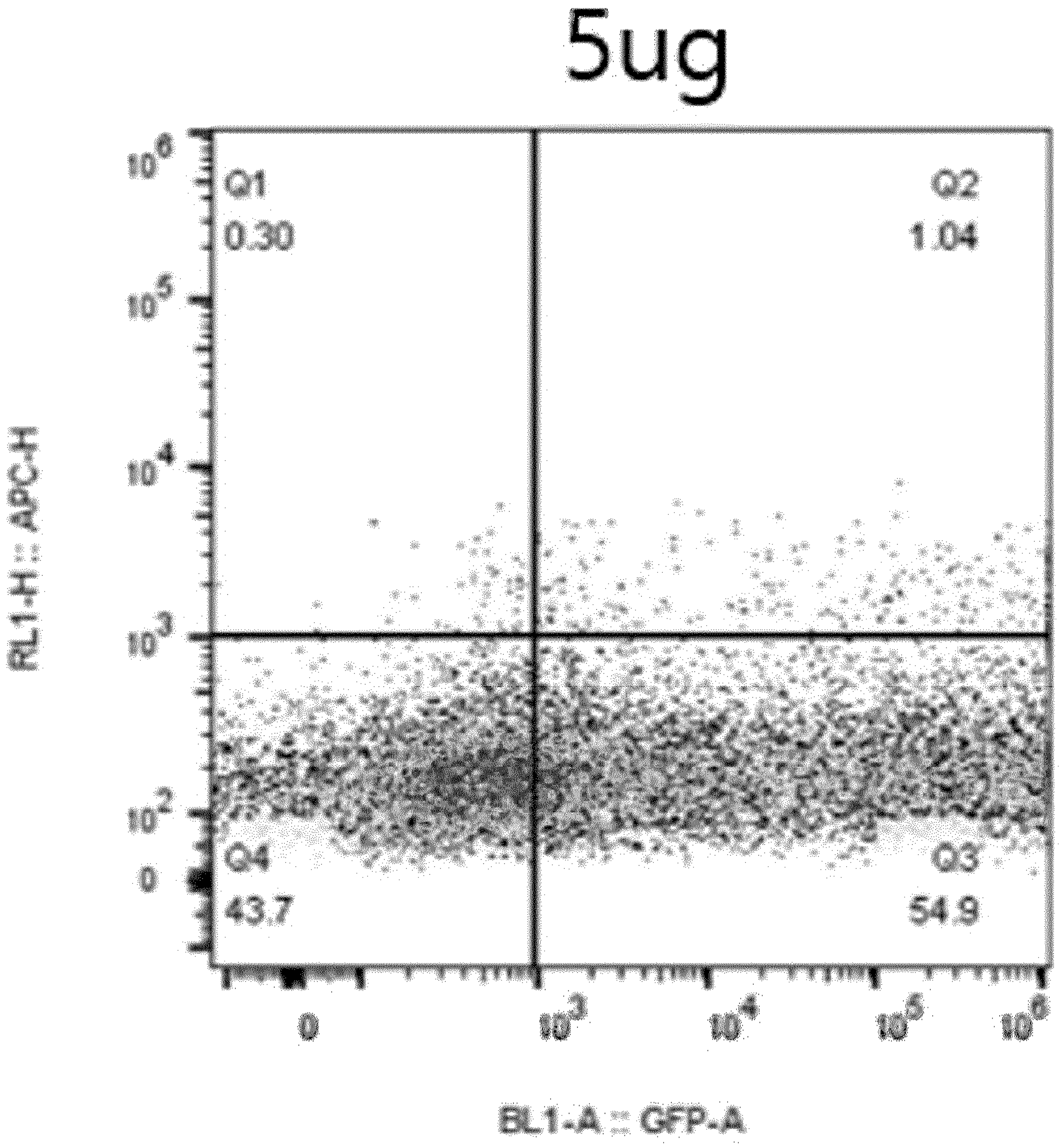
Figure 8:
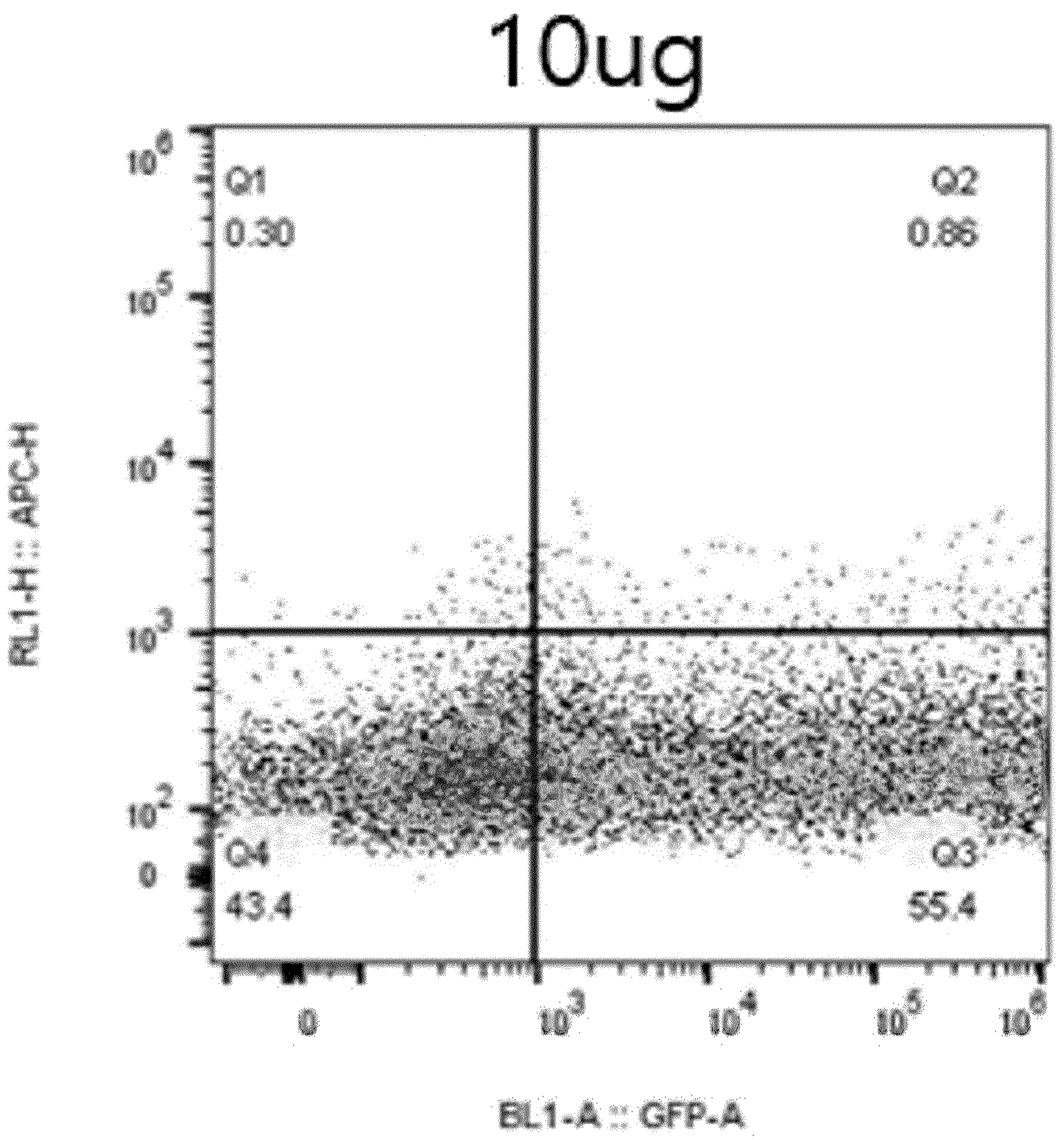
Figure 9:
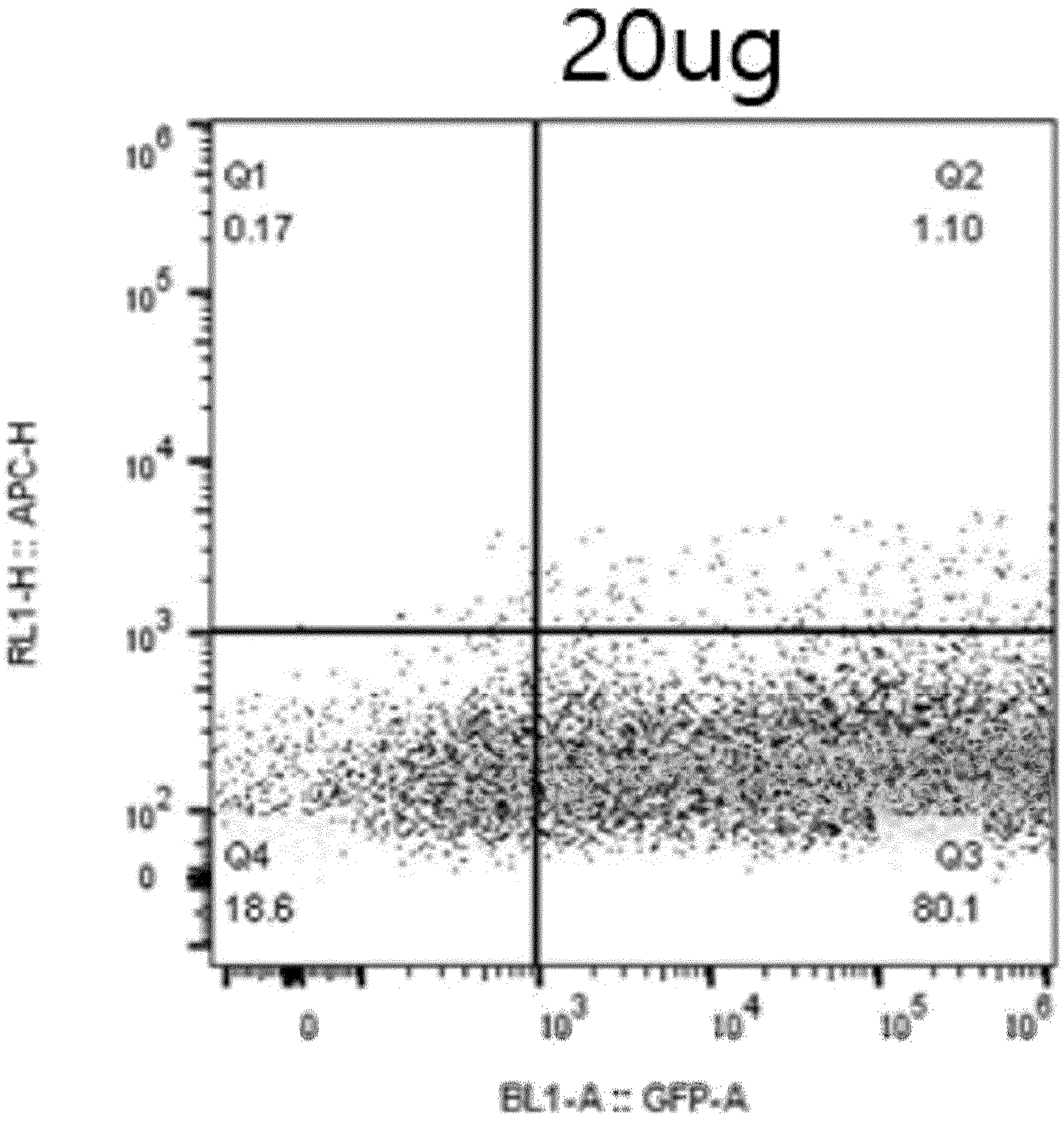

As a result of finding cells whose genes are edited by reacting with sgRNAs (nCC pam, nAA pam, nTT pam, nGC pam, nGA pam, and nGT pam5 in FIG. 5 and $1^{st}$ guide RNA in Table 1) targeting PAM sequences (5'-NCC-3', 5'-NTT-3', 5'-NAA-3', 5'-NGC-3', 5'-NGT-3', 5'-NGA-3') other than 5'-NGG-3' and screening Cas9 variants associated with the edited cells, it was assumed that the Cas9 variants commonly located at high ranks would be Cas9 variants that recognize PAM sequences other than 5'-NGG-3'.

To prove this, sgRNAs (nCC pam, nAA pam, nTT pam, nGC pam, nGA pam, and nGT pam in FIG. 5 and $2^{nd}$ guide RNA in Table 1) targeting a sequence adjacent to the PAM sequence (5'-NCC-3', 5'-NTT-3', 5'-NAA-3', 5'-NGC-3', 5'-NGT-3', 5'-NGA-3') other than 5'-NGG-3' in the HRPT gene were treated with the cas9 variants cell library produced in Experimental Example 3. The sgRNA was treated to induce knockout of the HPRT gene. In this case, 6-TG selection was performed to screen for cells associated with a Cas9 variant capable of recognizing PAM sequences other than 5'-NGG-3', ensuring that these cells survived.

In this case, before the screening was started, transfection was performed under each condition using a GFP expression vector to find the optimal transfection conditions in a 150-mm dish, and the results were analyzed by flow cytometry (80.1% transfection efficiency when 20 μg of Lipofectamine 2000 was used) (FIGS. 6, 7, 8, and 9).

TABLE 1

| Guide RNA type | Non-target sequence (5'-3')<br>Gide domain sequence (5'-3') | SEQ ID NO of non-target sequence<br>SEQ ID NO of guide domain sequence |
|---|---|---|
| $1^{st}$ guide RNA (nCC) | GTGATGAAGGAGATGGGAG<br>GUGAUGAAGGAGAUGGGAG | 13<br>57 |
| $1^{st}$ guide RNA (nTT) | GTGATGAAGGAGATGGGAG<br>GUGAUGAAGGAGAUGGGAG | 14<br>58 |
| $1^{st}$ guide RNA (nAA) | TGGATTACATCAAAGCACT<br>UGGAUUACAUCAAAGCACU | 15<br>59 |
| $1^{st}$ guide RNA (nGC) | TGGGAGGCCATCACATTGT<br>UGGGAGGCCAUCACAUUGU | 16<br>60 |
| $1^{st}$ guide RNA (nGT) | ATCACATTGTAGCCCTCTG<br>AUCACAUUGUAGCCCUCUG | 17<br>61 |
| $1^{st}$ guide RNA (nGA) | GGGGCTATAAATTCTTTGC<br>GGGGCUAUAAAUUCUUUGC | 18<br>62 |
| $2^{nd}$ guide RNA (nCC) | GAAATAGTGATAGATCCAT<br>GAAAUAGUGAUAGAUCCAU | 19<br>63 |
| $2^{nd}$ guide RNA (nTT) | TCAAGGGGGGCTATAAATT<br>UCAAGGGGGGCUAUAAAUU | 20<br>64 |
| $2^{nd}$ guide RNA (nAA) | GTGTGCTCAAGGGGGGCTA<br>GUGUGCUCAAGGGGGGCUA | 21<br>65 |

TABLE 1-continued

| Guide RNA type | Non-target sequence (5'-3') Gide domain sequence (5'-3') | SEQ ID NO of non-target sequence SEQ ID NO of guide domain sequence |
|---|---|---|
| $2^{nd}$ guide RNA (nGC) | CCTCTGTGTGCTCAAGGGG<br>CCUCUGUGUGCUCAAGGGG | 22<br>66 |
| $2^{nd}$ guide RNA (nGT) | CAAAGCACTGAATAGAAAT<br>CAAAGCACUGAAUAGAAAU | 23<br>67 |
| $2^{nd}$ guide RNA (nGA) | TTACATCAAAGCACTGAAT<br>UUACAUCAAAGCACUGAAU | 24<br>68 |

A secondary screening was performed to enrich positive hits from a cell pool subjected to primary screening through 6-TG selection. The cell pools screened for different PAM sequences were subjected to a secondary screening in the same manner as the primary screening using sgRNAs (2nd nCC pam, 2nd nAA pam, 2nd nTT pam, 2nd nGC pam, 2nd nGA pam, and 2nd nGT pam in FIG. 5) targeting different sequences adjacent to the same PAM sequence. Genomic DNA from the cell pools obtained from the primary screening and secondary screening was extracted (prep).

Experimental Example 2-3. Sequence Analysis of Selected SpCas9 Variants

Figure 10:
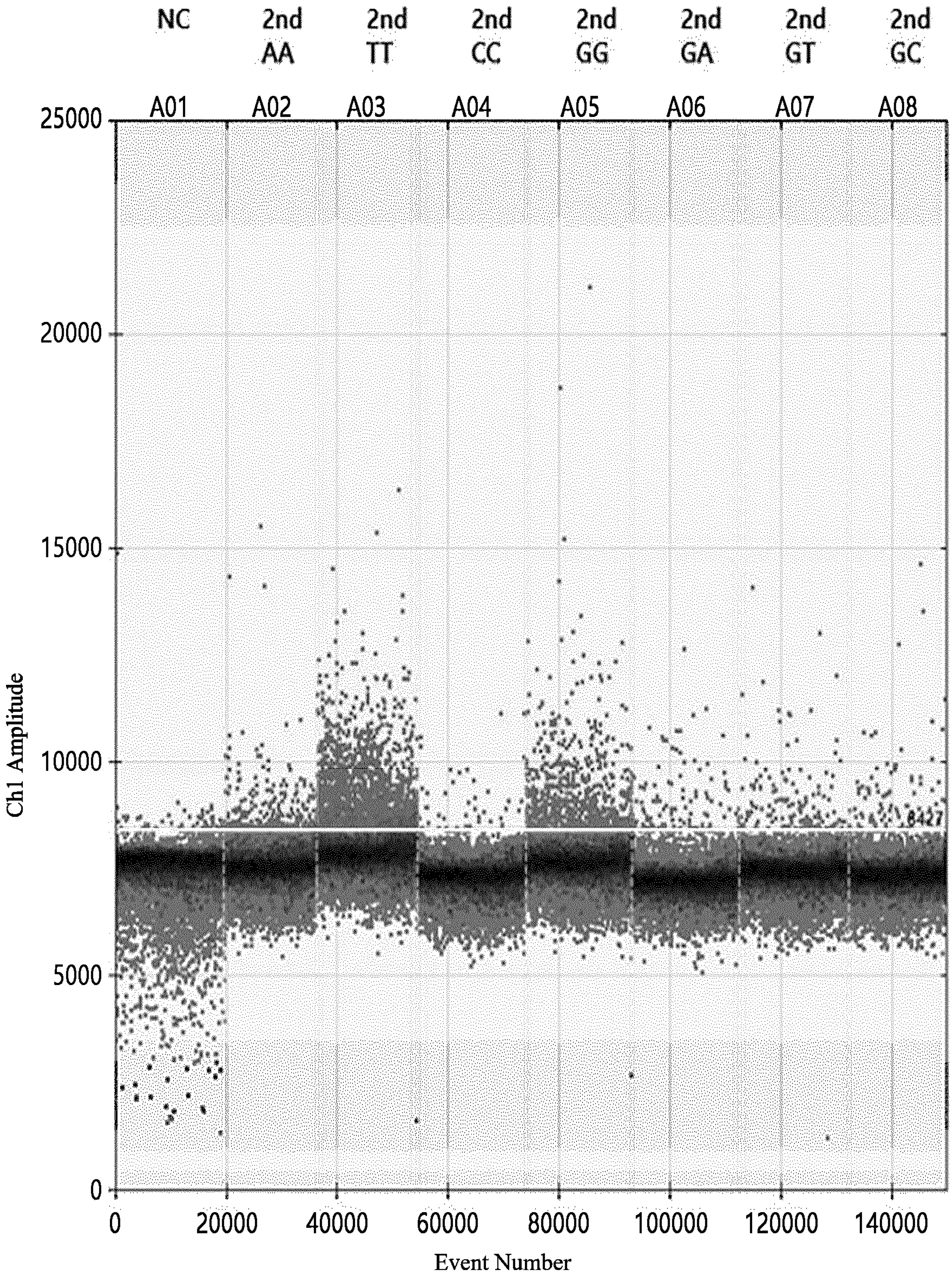
FIG. 10 shows the results of a 1st PCR performed by a ddPCR method.
Figure 11:
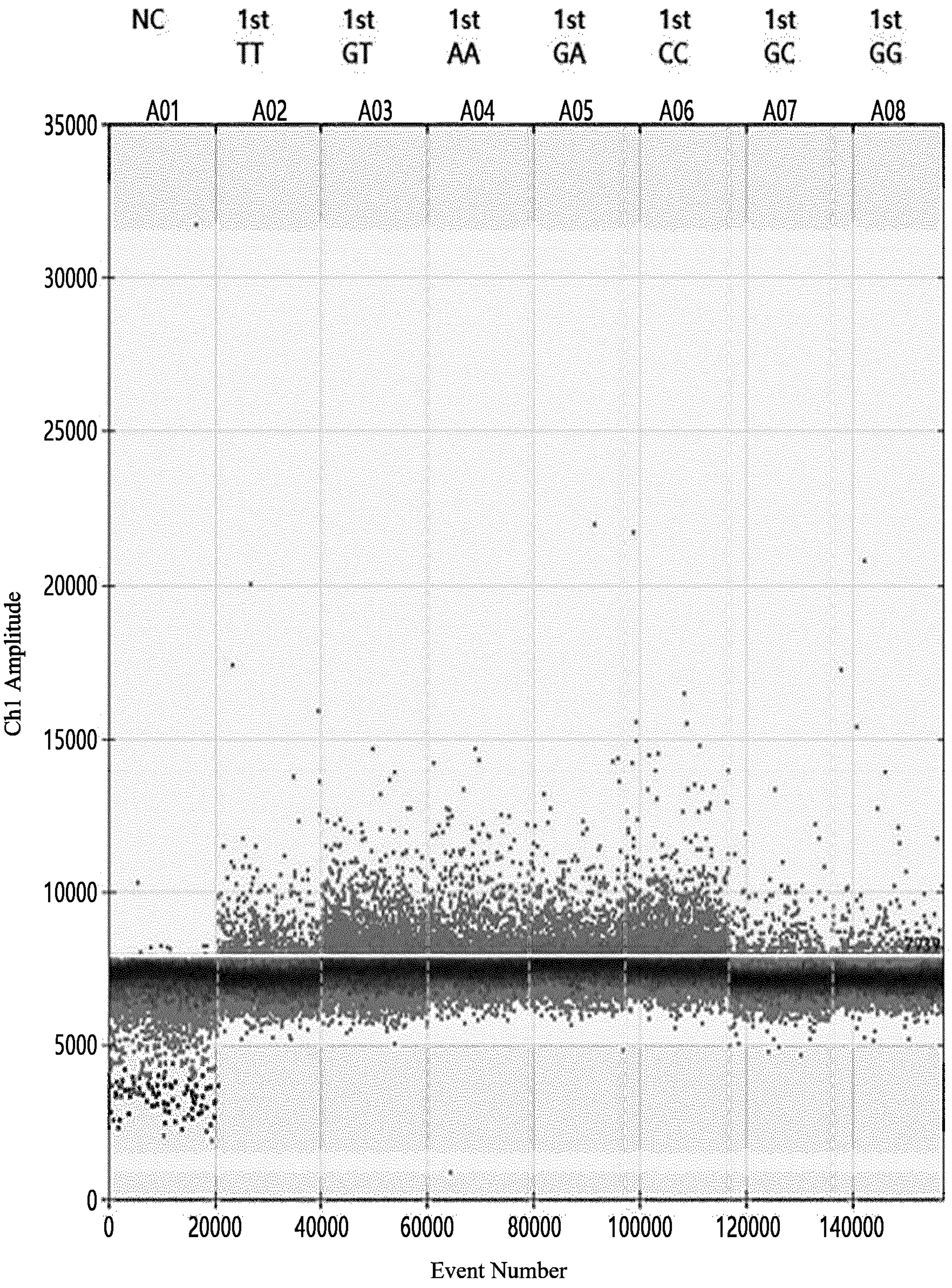
FIG. 11 shows the results of a 1st PCR performed by a general PCR method.

PCR was performed to search for hits from the obtained genomic DNA. In this case, due to the similar homology between the amplicons, the 1st PCR was performed in two forms: a ddPCR method (using 50 ng of genomic DNA=genomic 1 copy/drop) to prevent shuffling which may occur between hits of the two mutation loci, and a general PCR method which is not the ddPCR method (FIGS. 10 and 11).

Figure 12:
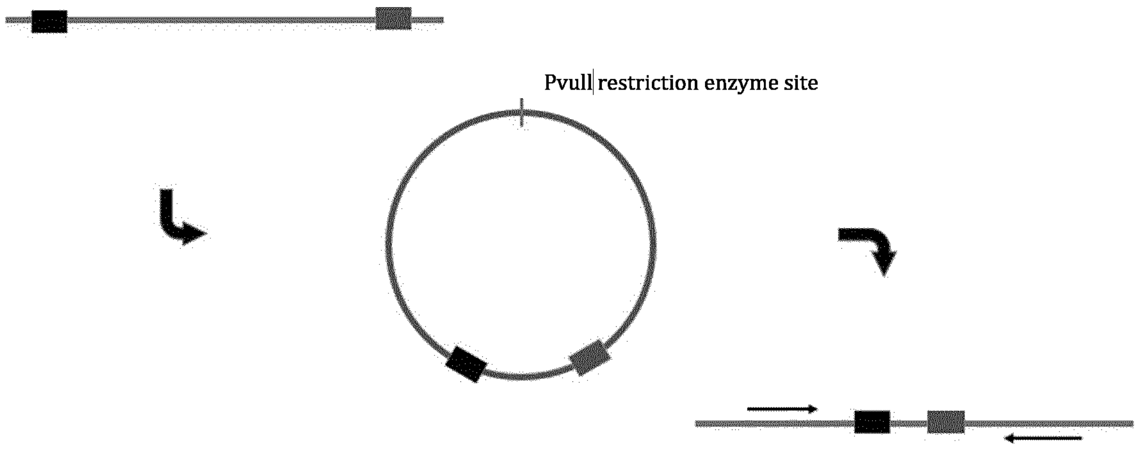
FIG. 12 shows a schematic view of a method of placing two mutation loci close to each other because Illumina sequencing cannot be performed due to a distance (350 bp) between the variation sites in the SpCas9 variant.

Since the distance between hits (350 bp) prevented illumina sequencing, two mutation loci were located close to each other (FIG. 12), a 1st PCR amplicon prepared in two forms, such that sequencing could be performed at once, was circularized, and then PCR for sequencing was performed.

Figure 13:
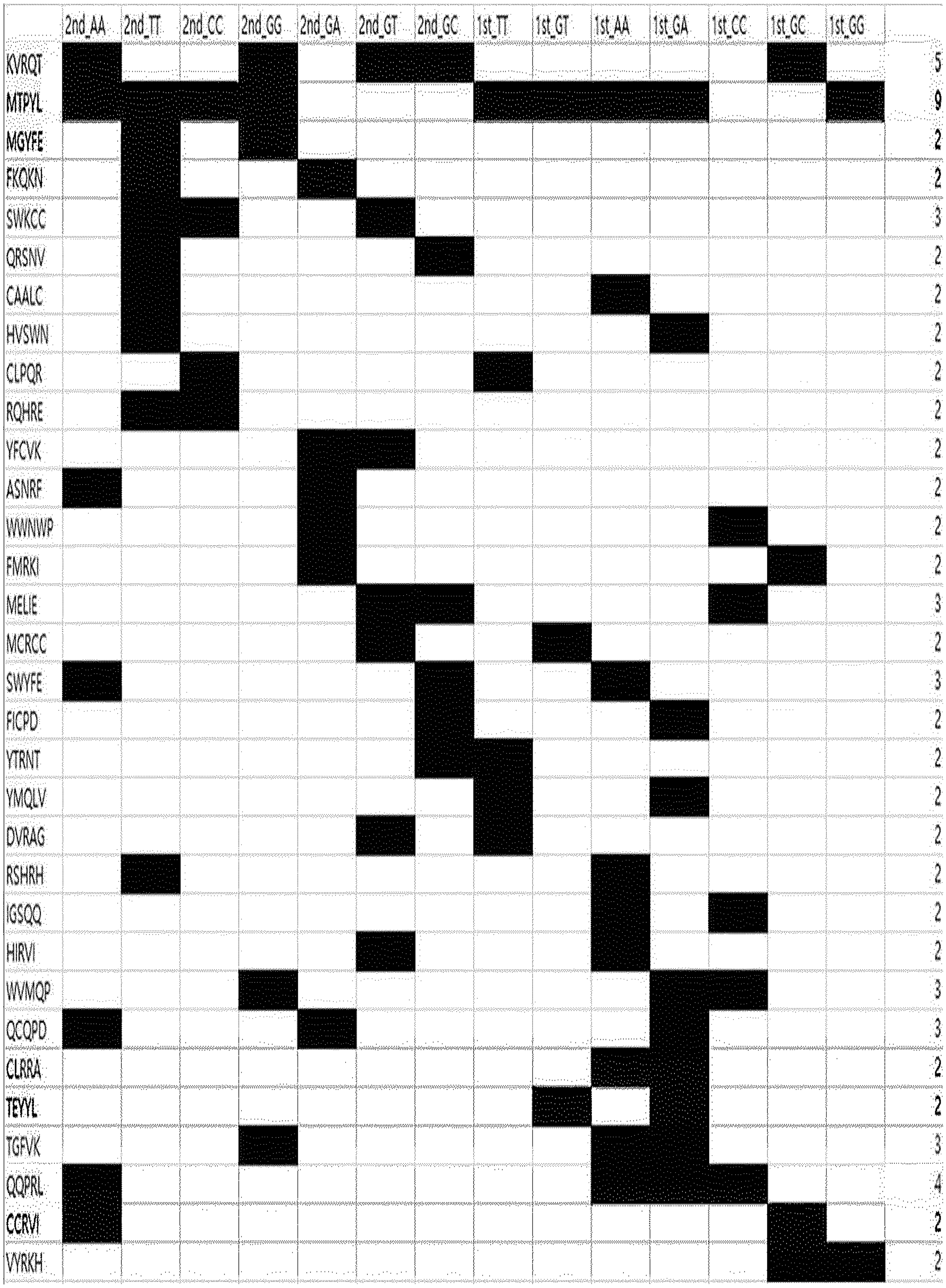
FIG. 13 shows the display of a PAM sequence recognized by each SpCas9 variant.

Experimental Example 2-4. Selection of Candidate Group of SpCas9 Variant with Novel PAM As a result of the NGS data analysis (FIG. 13), in the ddPCR method taking shuffling into consideration, 15 top rank hits obtained by screening in different PAMs were selected. Among these, those meeting the following three criteria were selected: 1) at least one amino acid residue is mutated at amino acid residues of G1218 and E1219; 2) at least one amino acid residue at amino acid residues of R1333, R1335, and T1337 is mutated; and 3) four or more mutations are found to overlap, except for sequences found in wild-type SpCas9 protein and Nureki-NG (except for WT-G1218/E1219, R1333/R1335/T1337, Nureki-NG-G1218R/E1219F, and R1333/R1335V/T1337R).

In this case, the selected mutations were G1218K/E1219V/R1335Q mutation, G1218Q/E1219Q/R1333P/T1337L mutation, and G1218M/E1219T/R1333P/R1335Y/T1337L mutation.

In the general PCR method performed by assuming shuffling, the 1218/1219 and 1333/1335/1337 parts were ranked separately and analyzed (FIG. 14). To search for PAMless Cas9, the NTT PAM, which had the lowest activity in WT-Cas9, and the G1218R/E1219F, R1333G/R1335H/T1337C mutation, which were analyzed as top-rankers in the NCC PAM, was selected.

Experimental Example 3. PAM Analysis of Selected Candidate Group

The present inventors attempted to confirm what the PAM sequences recognized by the four SpCas9 variants selected in experimental example 6 are. To confirm the PAM sequence, a transfection experiment was performed on a cell library for PAM analysis. Further, an additional experiment was performed in the same manner as in the above experiment to compare with a wild-type SpCas9 protein, Nureki-NG Cas9, and SPRY Cas9.

Experimental Example 3-1. PAM Analysis of Selected Candidate Group

Figure 15:
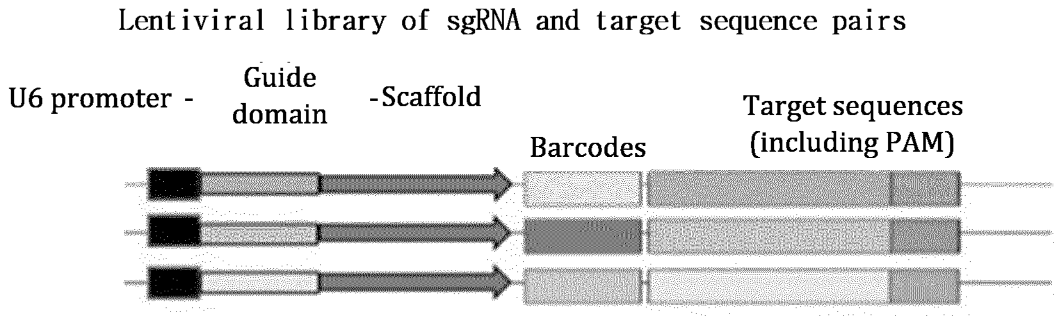
FIG. 15 is a schematic view of a guide RNA library used to confirm a PAM sequence recognized by a selected SpCas9 variant candidate group.

The selected candidates were individually cloned and transfected into a cell library for PAM analysis (as shown in FIG. 15, one guide RNA sequence corresponds to a total of 256 types of PAM sequences as 5'-NNNTA-3', and there are 30 types of guide RNA sequences), and then hi-seq was performed to analyze which PAM sequence the SpCas9 variant could recognize. In this case, the method described in the paragraph <<Transfection of selected Cas9 variants into PAM analysis cell libraries for PAM analysis>> was used.

As a result of the analysis, it was analyzed through FIG. 16 that the SpCas9 variant including the G1218K/E1219V/R1335Q mutation can recognize PAM sequence which is 5'-NGN-3'. Through FIG. 17, it was analyzed that the SpCas9 variant including the G1218Q/E1219Q/R1333P/T1337L mutation can recognize a PAM sequence which is 5'-NNG-3'. Through FIG. 18, it was analyzed that the SpCas9 variant including the G1218R/E1219F, R1333G/R1335H/T1337C mutation is PAMless. Through FIG. 19, it was analyzed that the SpCas9 variant including the G1218M/E1219T/R1333P/R1335Y/T1337L mutation is PAMless.

These results suggest that the method for screening the SpCas9 variant of the present specification may be used to find variants capable of recognizing PAM sequence other than 5'-NGG-3'.

FIGS. 16 to 25 show the activity according to the PAM sequence of the Cas9 protein, which is the subject of the experiment, with darker (or deeper) colors showing higher activity.

Experimental Example 3-2. Comparison of Activity According to a PAM Between Selected Candidate Group and Known SpCas9 Protein An additional analysis was performed in the same manner as in Experimental Example 7 on the wild-type SpCas9 protein of SEQ ID NO: 1 (FIG. 20), Nureki-NG Cas9 of SEQ ID NO: 2 (FIG. 21), SPRY Cas9 of SEQ ID NO: 12 (FIG. 22), G1218K/E1219V/R1335Q mutation of SEQ ID NO: 3 (FIG. 23), G1218Q/E1219Q/R1333P/T1337L mutation of SEQ ID NO: 3 (FIG. 24), and G1218R/E1219F, R1333G/R1335H/T1337C mutation of SEQ ID NO: 5 (FIG. 25). Analysis results in comparison with the known Cas9 protein show that the SpCas9 variant of the present disclosure recognizes PAM sequence which is each of 5'-NGN-3' and 5'-NNG-3', or is PAMless. That is, it is suggested that the methods of Experimental Examples 1 and 2 may be used to screen for SpCas9 variants capable of recognizing PAM sequences other than 5'-NGG-3'.

What is claimed is:

1. A *Streptococcus pyogenes* Cas9 (SpCas9) variant comprising the amino acid sequence selected from the group consisting of SEQ ID NOs: 3-6.

2. The SpCas9 variant of claim 1, wherein the amino acid sequence of the SpCas9 variant is SEQ ID NO: 3, and wherein the SpCas9 variant is capable of recognizing PAM sequence which is 5'-NGN-3'.

3. The SpCas9 variant of claim 1, wherein the amino acid sequence of the SpCas9 variant is SEQ ID NO: 4, and wherein the SpCas9 variant is capable of recognizing PAM sequence which is 5'-NNG-3'.

4. The SpCas9 variant of claim 1,
wherein the amino acid sequence of the SpCas9 variant is SEQ ID NO: 5, and
wherein the SpCas9 variant is PAMless.

5. The SpCas9 variant of claim 1,
wherein the amino acid sequence of the SpCas9 variant is SEQ ID NO: 6, and
wherein the SpCas9 variant is PAMless.

6. A composition, comprising:
the SpCas9 variant of claim 5 or a nucleic acid encoding the SpCas9 variant; and
a guide RNA or a nucleic acid encoding the guide RNA,
wherein the guide RNA comprises a crRNA and a tracrRNA,
wherein the guide RNA is capable of forming a complex by interacting with the SpCas9 variant,
wherein the guide RNA is capable of binding to a target sequence of a target gene.

7. The composition of claim 6, wherein the amino acid sequence of the SpCas9 variant is SEQ ID NO: 3, and
wherein the SpCas9 variant is capable of recognizing PAM sequence which is 5'-NGN-3'.

8. The composition of claim 6, wherein the amino acid sequence of the SpCas9 variant is SEQ ID NO: 4, and
wherein the SpCas9 variant is capable of recognizing PAM sequence which is 5'-NNG-3'.

9. The composition of claim 6, wherein the amino acid sequence of the SpCas9 variant is SEQ ID NO: 5, and
wherein the SpCas9 variant is PAMless.

10. The composition of claim 6, wherein the amino acid sequence of the SpCas9 variant is SEQ ID NO: 6, and
wherein the SpCas9 variant is PAMless.

11. The composition of claim 6, wherein the crRNA comprises a guide domain and a direct repeat, wherein a sequence of the direct repeat comprises a sequence having at least 90% sequence identity to SEQ ID NO: 7,
wherein a sequence of the tracrRNA comprises a sequence having at least 90% sequence identity to SEQ ID NO: 8.

12. The composition of claim 6, wherein the composition comprises the SpCas9 variant and the guide RNA,
wherein the SpCas9 variant and the guide RNA are in a form of ribonucleoprotein (RNP).

13. The composition of claim 6, wherein the composition comprises vector which comprises the nucleic acid encoding the SpCas9 variant and/or the nucleic acid encoding the guide RNA.

14. The composition of claim 6, wherein the composition further comprises a Nuclear Localization Sequence (NLS) or a nucleic acid encoding the NLS.

* * * * *